(12) United States Patent
Voelkel

(10) Patent No.: US 6,875,581 B1
(45) Date of Patent: Apr. 5, 2005

(54) METHOD FOR SCREENING OF MODULATORS OF CALCINEURIN ACTIVITY

(75) Inventor: Helge Voelkel, Ulm (DE)

(73) Assignee: Genopia Biomedical GmbH, Saarbrucken (DE)

( * ) Notice: Subject to any disclaimer, the term of this patent is extended or adjusted under 35 U.S.C. 154(b) by 0 days.

(21) Appl. No.: 09/744,016

(22) PCT Filed: Jul. 22, 1999

(86) PCT No.: PCT/EP99/05220

§ 371 (c)(1),
(2), (4) Date: May 7, 2001

(87) PCT Pub. No.: WO00/05363

PCT Pub. Date: Feb. 3, 2000

(30) Foreign Application Priority Data

Jul. 22, 1998 (EP) .............................................. 98113876

(51) Int. Cl.$^7$ ............................ C12N 9/16; C12N 9/04; C12N 5/16; C12N 1/20; C12Q 1/44; G01N 33/58; C07H 21/04

(52) U.S. Cl. .......................... 435/21; 435/19; 435/190; 435/7.9; 435/7.92; 435/7.72; 435/325; 435/252.33; 435/196; 536/23.2

(58) Field of Search ........................... 435/196, 19, 21, 435/190, 7.9, 7.92, 7.72, 325, 252.33, 212, 226, 23; 536/23.2

(56) References Cited

U.S. PATENT DOCUMENTS

| 5,723,436 A | 3/1998 | Huang et al. ................... 514/2 |
| 5,807,693 A | 9/1998 | Scott et al. ................. 435/7.21 |
| 5,978,740 A | 11/1999 | Armistead et al. ............ 702/19 |

FOREIGN PATENT DOCUMENTS

| EP | 0 750 193 A1 | 12/1996 | .......... G01N/33/15 |
| JP | 6 181778 | 7/1994 | ........... C12N/15/57 |

OTHER PUBLICATIONS

Boopathy et al Purification and characterization of sheep platelet cyclo–oxygenase. Acetylation by aspirin prevents haemin binding to the enzyme. Biochem J. Oct. 15, 1986;239(2):371–7.*

Brown MP, Royer C. Fluorescence spectroscopy as a tool to investigate protein interactions. Curr Opin Biotechnol. Feb. 1, 1997;8(1):45–9.*

Aramburu J, Garcia–Cozar F, Raghavan A, Okamura H, Rao A, Hogan PG. Selective inhibition of NFAT activation by a peptide spanning the calcineurin targeting site of NFAT. Mol Cell. Apr. 1998;1(5):627–37.*

Lau LF, Mammen A, Ehlers MD, Kindler S, Chung WJ, Garner CC, Huganir RL. Interaction of the N–methyl–D–aspartate receptor complex with a novel synapse–associated protein, SAP102. J Biol Chem. Aug. 30, 1996;271(35):21622–8.*

Woodrow M, Clipstone NA, Cantrell D. p21ras and calcineurin synergize to regulate the nuclear factor of activated T cells. J Exp Med. Nov. 1, 1993;178(5):1517–22.*

Robbins DJ, Zhen E, Owaki H, Vanderbilt CA, Ebert D, Geppert TD, Cobb MH. Regulation and properties of extracellular signal–regulated protein kinases 1 and 2 in vitro. J Biol Chem. Mar. 5, 1993;268(7):5097–106.*

Lee, J.–P., et al., "Calcineurin activity in PC12 cells expressing a human ALS–associated SOD–1 mutant." abstract No. 215.12, XP–000862971, (1997).

Wang, X., et al., "Superoxide dismutase protects calcineurin from inactivation", *Nature*, vol. 383, pp. 434–437, (Oct. 3, 1996).

Mondragon, A., et al., "Overexpression and Purification of Human Calcineurin α from *Escherichia coli* and Assessment of Catalytic Functions of Residues Surrounding the Binuclear Metal Center", *Biochemistry*, vol. 36, pp. 4934–4942, (1997).

Elroy–Stein, O., et al., "Overproduction of human Cu/Zn–superoxide dismutase in transfected cells: extenuation of paraquat–mediated cytotoxicity and enhancement of lipid peroxidation", *The EMBO Journal*, vol. 5, no. 3, pp. 615–622, (1986), XP–000862989.

Sehrsam, I., et al., "Fluorescent exzymatic assay of Calcineurin and other proteinphosphatases (Ppases)", Abstract No. 50.3, XP–000863027, (1998).

Lee, J.–P., et al., "The role of immunophilins in mutant superoxide dismutase–1–linked familial amyotrophic lateral sclerosis", *Proc. Natl. Acad. Sci.*, vol. 96, pp. 3251–3256, (Mar. 1999).

Database WPI, JP 06 181778 A, XP–002098865, abstract.

Guerini, D., and Klee, C.B., "Cloning of human calcineurin A: Evidence for two isozymes and identification of a polyproline structural domain", *Proc. Natl, Acad. Sci. USA*, vol. 86, pp. 9183–9287, (Dec. 1989).

(Continued)

*Primary Examiner*—Rebecca E. Prouty
*Assistant Examiner*—Sheridan L. Swope
(74) *Attorney, Agent, or Firm*—Nath & Associates PLLC; Gary M. Nath; Lee C. Heiman

(57) ABSTRACT

A method for screening of modulators of calcineurin is provided, which uses the interaction between calcineurin and superoxide dismutase. Modulators of calcineurin are potential candidates for drugs, e.g. for immunosuppressive drugs. The forming of a complex comprising calcineurin and superoxide dismutase is monitorable in the presence of potential activators or inhibitors of calcineurin. Complex formation is performed within the cell by the use of appropriate expression vectors or in vitro using isolated proteins. Preferably, complex formation is monitored by fluorescence detection, especially by laser fluctuation correlation spectroscopy.

22 Claims, No Drawings

OTHER PUBLICATIONS

Guerini, D., "Isolation and Sequence of a cDNA Clone for Human Calcineurin B, the $Ca^{2+}$-Binding Subunit of the $Ca^{2+}$/Calmodulin–Stimulated Protein Phosphatase", *DNA*, vol. 8, No. 9, (1989), XP–002062997.

Muramatsu, T. and Kincaid, R.L., "Molecular cloning and chromosomal mapping of the human gene for the testis–specific catalytic subunit of calmodulin–dependent protein phosphatase (Calcineurin A)", *Biochem. and Biophys. Res. Communications*, vol. 188, No. 1, pp. 265–271, (Oct. 15, 1992).

Gamonet, F. and Lauquin, G.J.–M., "The *Saccharomyces cerevisiae* LYS7 gene is involved in oxidative stress protection", *Eur. J. Biochem.*, vol. 251, pp. 716–723, (1998) XP–000857423.

Blumenthal, D.K., et al., "Dephosphorylation of cAMP–dependent Protein Kinase Regulatory Subunit (Type II) by Calmodulin–dependent Protein Phosphatase", *Journal of Biological Chemistry*, vol. 261, No. 18, pp. 8140–8145, (Jun. 25, 1986).

Stemmer, P.M. et al., "Factors responsible for the $Ca^{2+}$–dependent inactivation of calcineurin in brain", *FEBS Letters*, vol. 374, pp. 237–240, (1995).

Tatlock, J.H., et al., "Structure–based Design of Novel Calcineurin (PP2B) inhibitors", *Bioorganic & Medicinal Chemistry Letters*, vol. 7, No. 8, pp. 1007–1012, (1997).

Kincaid, R.L., et al., "Cloning and Characterization of Molecular Isoforms of the Catalytic Subunit of Calcinuerin using Nonisotopic Methods", *J. Biol. Chem*, vol. 265, No. 19, pp. 11312–11319, (Jul. 5, 1990) XP–002098864.

\* cited by examiner

METHOD FOR SCREENING OF MODULATORS OF CALCINEURIN ACTIVITY

This application claims the benefit to foreign priority under 35 U.S.C. §119 of European Patent Application No. 98113876.1, filed on Jul. 22, 1998, the contents of which are hereby incorporated by reference in their entirety.

The invention relates to a method for screening of modulators of calcineurin.

Calcineurin (E.C. 3.1.3.16) is a serine/threonine phospho-protein phosphatase and is composed of a catalytic (calcineurin A) and regulatory (calcineurin B) subunit (about 60 and about 18 kDa, respectively). In mammals, three distinct genes (A-alpha, A-beta, A-gamma) for the catalytic subunit have been characterized, each of which can undergo alternative splicing to yield additional variants. Although mRNA for all three genes appears to be expressed in most tissues, two isoforms (A-alpha and A-beta) are most predominant in brain.

Calcineurin has been cloned from various organisms including human (Guerini et al., 1989), (Guerini and Klee, 1989), (Kincaid et al., 1991), (Kuno et al., 1989), (Ito et al., 1989), (Muramatsu and Kincaid, 1993). The crystal structure has shown that calcineurin A contains a binuclear metal center with unknown enzymatic function (Griffith et al., 1995). Recombinant expression of rat calcineurin A subunit in bacteria or SF9-cells were not effective and yielded only poor enzymatic activities since calcineurin A is not stable in the absence of calcineurin B (Perrino et al., 1992), (Perrino et al., 1995), (Haddy and Rusnack, 1994). Coexpression of calcineurin A and calcium binding subunit calcineurin B yielded a more stable and active enzyme (Mondragon et al., 1997). Calcineurin has been implicated in various neuronal signaling pathways (Klee et al., 1988), (Yakel, 1997) but the neuronal function is only poorly understood (Guerini, 1997).

Calcineurin is the only protein phosphatase known to be under the control of $Ca^{2+}$ and calmodulin. Binding of $Ca^{2+}$ and calmodulin is necessary for enzymatic activity. Calmodulin is bound by the catalytic subunit whereas the regulatory subunit possesses four $Ca^{2+}$ binding sites.

Calcineurin is discussed in the context of immunosuppression. It has been shown that calcineurin acts via the transcription factor NFAT (nuclear factor of activated T cells) on the T cell response. The functions of NFAT proteins are directly controlled by calcineurin in a calcium- and calmodulin-dependent manner. Activation of NFAT by calcineurin is mediated by the cytosolic binding protein FKBP.

Substances which are able to block the calcineurin signal pathway are suitable agents in order to block the T cell activation and thereby suppressing the immune response. Suppression of immune response has important clinical relevance, for example in transplantation surgery for preventing rejection episodes. Therefore, calcineurin as pharmacological target is of great importance and several attemps were made to develop agents which block the calcineurin signal pathway. Examples of such immunosuppressive drugs are FK506 (Fujisawa) and cyclosporine (Novartis) (Liu et al, 1991). These antibiotics inhibit calcineurin phosphatase activity in the presence of immunophilin receptor proteins (FKBP, cyclophillin) and thereby suppress immune response by preventing the activation of the T cell transcription factor NFAT (Liu et al., 1992), (Nelson et al., 1993). FK50G (tacrolimus) binds to the binding protein FKBP and thereby prevents calcineurin from binding to FKBP. Accordingly the signal pathway is interrupted. No activation of the transcription factor NFAT is achieved and the T cell activation is disturbed.

Nevertheless, there are several severe disadvantages and side-effect of said drugs. In clinical trials with liver and renal transplant recipients it has been shown that FK506-based therapy was associated with increased toxicities in comparison to conventional therapy. Furthermore FK506 has negative effects on the bone mineral physiology.

Besides the role of the calcineurin signal pathway in immune response it has been shown that calcineurin is involved in apoptosis induction by glutamate excitotoxicity in neuronal cells (Ankarcrona et al., 1996) Low enzymatic levels of calcineurin have been associated with Alzheimers disease (Ladner et al., 1996), (Kayyali et al., 1997). Calcineurin inhibitors (FK506, Cyclosporin) prevented epileptogenesis in model organisms (Moriwaki et al., 1996). In the heart or in the brain calcineurin also plays a key role in the stress response after hypoxia or ischemia (Butcher et al., 1997), (Hashimoto et al., 1998), (Molkentin et al., 1998).

In summary, calcineurin is a crucial target to develop new substances suitable as drugs, especially as immunosuppressive drugs. Former screening systems using purified calcineurin and conventional assays like radioactive or HPLC assays (Klee, 1991), (Enz et al., 1994) did not lead to appropriate new substances. Therefore, the invention has the object to provide a new screening system for modulators of calcineurin taking advantage of new insights into the signal pathway of calcineurin. By the use of this new screening system it is possible to develop new pharmaceuticals with respect to the field of transplantation surgery, cardiac infarction and apoplexy, chronic or acute neurodegeneration and inflammatory diseases, for example. This object is solved by a method as described herein. Preferred embodiments of the inventive method are further described herein. A kit, vectors, cells and a peptide suitable for performing the inventive method are also described herein. The wording of all claims is hereby incorporated in the specification by reference.

The inventive method is based on results showing that a physiological interaction between calcineurin and superoxide dismutase takes place which provides a suitable target for developing of a new screening system.

For a long time it was not understood why recombinant or even purified calcineurin exhibited only 1 to 2% of the specific activity estimated in crude brain extracts until it was detected that the binuclear metal center of the enzyme contains a redoxsensitive $Fe^{2+}$ (Yu et al., 1997). After calcium activation or during purification procedure the $Fe^{2+}$ is oxidized by oxygen species and turns the enzyme inactive (Stemmer et al., 1995), (Wang et al., 1996).

Recently it has been shown that copper/zinc superoxide dismutase (CuZnSOD, EC 1.15.1.1) protects calcineurin against oxidative inactivation (Wang et al., 1996). The phosphatase activity of calcineurin is strongly dependent on the presence of calcium and calmodulin. The addition of $Ca^{2+}$ in the presence of calmodulin leads to a drastic increase in activity. But during several minutes this activity is lost. By the addition of copper/zinc superoxide dismutase the activity can be maintained.

Superoxide dismutase (SOD) dismutates the hyperoxide anion (superoxide) into hydroperoxide and molecular oxygen. There are two forms of this enzyme: the mitochondrial form containing manganese and the cytosolic form containing copper and zinc. In general superoxide dismutase is considered to be a catcher of radicals and is discussed in the field of detoxification of reactive oxygen species. Therefore, the role of superoxide dismutase in the protection of the activity of calcineurin found by Wang et al. was considered to be the result of general redox function of superoxide dismutase. Now, surprising results of the inventor lead to the knowledge that a physiological interaction between calcineurin and superoxide dismutase takes place. Several mutants of copper/zinc superoxide dismutase lacking the enzymatic function showed the protective effect on the activity of calcineurin. That means that the effect of CuZnSOD is not due to the function of superoxide dismutase in redox regulation. These results teach that superoxide dismutase interacts physiologically with calcineurin and that CuZnSOD is one component of the calcineurin pathway which is important for the physiological functions of calcineurin.

These results are used to develop a new screening system for modulators of calcineurin in order to find inhibitors or activators of the calcineurin signal pathway. The inventive method is based on the complex formation between calcineurin and superoxide dismutase in the presence of potential modulators of this physiological interaction. If a potential modulator disturbs the complex formation, this substance is a good canditate for inhibiting the calcineurin signal pathway and could possibly be used as immunosuppressive drug, for example. On the other hand it could be favourable to identify a substance which promotes complex formation and thereby stimulates the calcineurin signal pathway, e.g. the T cell response in result. Such a substance could be used in order to strengthen immune response. By the term "modulator" is meant any substance which influences the complex formation relating to the inventive method. Additionally is meant any substance which influences the interaction between calcineurin and its substrates, e.g. the peptide RII. Furthermore is meant any substance which influences the superoxide dismutase and/or calcineurin on the transcriptional, the translational and/or the posttranslational level.

Calcineurin as used in the inventive method is build up by the regulatory subunit A and the catalytic subunit B. The presence of both subunits is essential for physiological activity of calcineurin. Nevertheless, it is possible to perform the inventive method using only one of the subunits. There are several isoforms of calcineurin consisting of subunit calcineurin B and one out of the group comprising subunit calcineurin A-alpha, A-beta and A-gamma. Each isoform represents a special cell and tissue specific distribution. Therefore, the choice of isoform could be crucial for cell and tissue specifity of the substance to be screened. With respect to clinical application of the substances to be screened preferably human forms of the proteins are used.

Furthermore it is preferred to perform the inventive method in the presence of calmodulin and calcium, because the activity of calcineurin is dependent on these factors. Preferably the cytosolic form of superoxide dismutase containing copper and zinc is used for complex formation, because interaction between the mitochondrial form of superoxide dismutase containing e.g. manganese normally does not occur under physiological conditions. The complex formation is performed in the presence of at least one potential modulator of calcineurin or the calcineurin signal pathway, respectively. The complex comprising calcineurin A, calcineurin B, superoxide dismutase and preferably calmodulin is the target for potential modulators which could stabilize or disturb the complex.

Advantageously, the complex formation is monitored during the whole process. It is possible to add the modulator before or after the complex formation has been performed. Preferably the modulator is added before complex formation because the effect of a weak modulator will possibly not be monitorable when complex formation has already finished.

In principle, there are two possibilities to monitor the complex formation. Firstly, the complex formation is directly monitored by the use of labeled components in the complex, preferably by fluorescence detection. Secondly, the complex formation is monitored by the activity of the complex, especially the enzymatic activity of calcineurin. This second method can be performed in addition to the firstly mentioned method or as an alternative. Clearly, the inventive method is not restricted by the method for detecting the influence of the modulator on complex formation.

In a preferred embodiment of the invention, a mixture of substances comprising at least one potential modulator is analyzed by the inventive method. By isolating the complex together with the possibly interacting modulator it is possible to separate the modulator out of the mixture and to identify it by common methods.

In one preferred embodiment of the invention the calcineurin and/or superoxide dismutase are labeled. Especially preferred is the use of fluorescent labels. Preferably, the labeled proteins are fusion proteins comprising a fluorescent protein, e.g. enhanced green fluorescent protein (EGFP). These fusion proteins are provided by genetic engineering methods. It is also possible to label said proteins by other methods known to experts in the art, e.g. by the use of radioactive isotopes which are incorporated into the proteins.

Advantageously the components of the complex, i.e. calcineurin and superoxide dismutase are expressed in the cell, especially in an eukaryotic cell, as fluorescent fusion proteins. By the use of laser fluctuation correlation spectroscopy the complex formation of labeled proteins is monitored directly within the cell. This embodiment of the invention is described in greater detail in the example. The invention comprises several vectors useful for the expression of calcineurin and/or superoxide dismutase in eukaryotic cells. These vectors encode the proteins, especially CuZnSOD and the different subunits of calcineurin, as fusion proteins in connection with the fluorescent protein EGFP (enhanced green fluorescent protein). EGFP is only one example of possible labels useful in respect of the inventive method. Furthermore, the invention comprises cells, especially eukaryotic cells, stably transfected with the above-mentioned vectors thereby expressing superoxide dismutase and/or calcineurin. Preferably, these proteins are coexpressed, i.e. expressed within the same cell.

In an especially preferred embodiment, the genetic information of fusion proteins is integrated in the cell by homologous recombination. That means that the gene encoding the recombinant protein, especially the fluorescent fusion protein, is incorporated in the genome of the cell in the place of the naturally occuring gene. This leads to a cell essentially lacking the natural protein. By the use of such cells it is possible to identify modulators by the inventive method which influence the transcriptional, translational or post-translation level of calcineurin and/or superoxide dismutase expression.

In another embodiment of the inventive method the components of the complex are isolated and preferably purified before complex formation is performed in vitro. Advantageously, the proteins are provided with a tag in order to facilitate purification, e.g. a histidine (his) tag consisting of several histidines in sequence which permits affinity purification by known procedures. Corresponding vectors encoding the tagged proteins are comprised by the invention. These vectors are especially useful as prokaryotic expression vectors. Furthermore, the invention comprises cells bearing said vectors.

Advantageously, following purification of the his-tagged proteins the tag is excised by appropriate enzymatic digestion, e.g. by the use of cathepsin-C of carboxypeptidase-A. Especially preferred is the purification of calcineurin by ferro-nitrilotricacetat-metal (Fe-NTA) affinity chromatography and the purification of superoxide dimutase by copper/zinc-nitrilotriacetat-metal (CuZn-NTA) affinity chromatography. Nevertheless, other purification procedures known to experts in the art are possible. Natural occuring protein could also be used in the inventive manner.

with fluorescein by incubating the peptide with fluroescein-phosphoamidit, thereby providing a labeled substrate (RII-Fluophos). RII interacts with the active center of calcineurin, but it is not converted by the phosphatase. Hereby it is possible to label calcineurin in the active state. Furthermore, it is possible to phosphorylate RII-Fluophos at the fluorescein moiety as depicted below at tyrosine residues. Due to the phosphorylation RII-Fluophos loses its fluorescence and thereby provides a phosphatase substrate which becomes fluorescent subsequent to dephosphorylation.

R1 = H

R2 = —P(=O)(OH)(OH)

R3 = —C(=O)C(CH3)(CH3)(CH3)

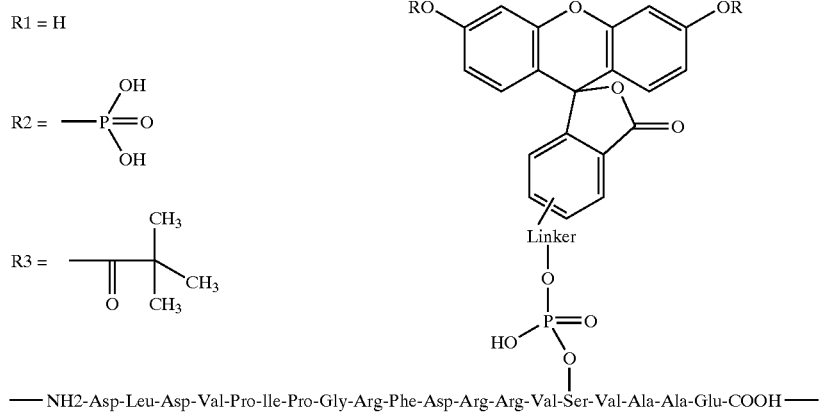

— NH2-Asp-Leu-Asp-Val-Pro-Ile-Pro-Gly-Arg-Phe-Asp-Arg-Arg-Val-Ser-Val-Ala-Ala-Glu-COOH —

Besides the use in purification of calcineurin and/or superoxide dismutase Ni (nickel)-NTA, Fe-NTA and/or Cu/Zn-NTA is used to immobilize the his-tagged calcineurin and/or superoxide dismutase in order to isolate naturally occuring ligands of these proteins using this inventive matrix. By the term "ligand" is meant any low- or highmolecular endogenous, exogenous or synthetic substance which interacts with said proteins. This could be a peptide, protein, carbohydrate, lipid, nucleic acid or a synthetic polymer, for example. These so-identified ligands are potential candidates for modulators of the calcineurin signal pathway.

When performing complex formation in vitro it could be preferred to add calmodulin and/or calcium to the reaction because these factors are necessary for enzymatic activity of calcineurin.

In another preferred embodiment of the invention the complex formation is monitored indirectly by analyzing the enzymatic activity of calcineurin. As outlined above the phoshatase activity of calcineurin is strictly dependent on the interaction with superoxide dismutase. Therefore, it is possible to monitor the complex formation indirectly by the measurement of phosphatase activity according to standard procedures. This is especially preferred if the laboratory equipment to perform fluorescent measurements as described above is not available. Furthermore, enzymatic analysis could be used in addition to fluorescence detection like laser fluctuation correlation spectroscopy, e.g. as control.

Preferably the enzymatic activity is analyzed by the use of a labeled substrate of calcineurin. The substrate is preferably labeled by fluorescence. One especially preferred substrate is the peptide RII characterized by the sequence, SEQ ID 35:

Asp-Leu-Asp-Val-Pro-Ile-Pro-Gly-Arg-Phe-Asp-Arg-Arg-Val-Ser-Val-Ala-Ala-Glu.

In a preferred embodiment this peptide carries a fluorescent label at serine in position 15. This amino acid is labeled This peptide could be provided synthetically or it is expressed by cells, especially eucaryotic cells, which have been transfected with appropriate vectors encoding said peptide or other peptides useful as phosphatase substrates. In one embodiment of the invention the fluorescent peptide is used as peptide label in fluorescence microscopy. This provides another method in order to analyze the active state of the calcineurin/superoxide complex.

The inventive method as outlined above is suitable for developing a high-throughput bioassay to identify inhibitors and/or activators of the calcineurin signal pathway. Details are described in the example.

The invention comprises the use of inhibitors of activators of the calcineurin signal pathway for the treatment of acute and/or chronic neurological and cardiovascular diseases like Alzheimer, Parkinson, epilepsy, ischemia and heart-failure. Furthermore the use as immunosuppressive drugs, e.g. in the field of transplantation surgery and inflammatory diseases is included.

Finally the invention comprises a kit for screening of modulators of calcineurin. The kit provides calcineurin and superoxide dismutase enabling complex formation for the screening for modulators of calcineurin as described above. In a first embodiment of the kit the components of the complex are provided as proteins. This kit is suitable for performing the inventive method in vitro. In a second embodiment of the kit the proteins are provided in the form of vectors. These vectors have to be transformed/transfected into cells leading to the expressed proteins. These vectors are prokaryotic or eukaryotic expression vectors, respectively, and could be used to produce the proteins for the in vitro assay or for the assay using complete cells as described above. In a third embodiment of the inventive kit cells transformed/transfected with the said vectors are provided saving the step of transforming/transfecting for the user. For details of the inventive kit reference is made to the above description.

The new approach to identify new substance classes of calcineurin/CuZnSOD inhibitors comprises inter alia:

coexpression of CuZnSOD/calcineurin A and calcineurin B to generate a oxidative stable enzyme which is suitable for drug screening, efficient purification of CuZnSOD on CuZn-nitrilotriacetat-metal affinity chromatography to retain enzymatic activity, efficient purification of calcineurin on Fe-nitrilotriacetat-metal affinity chromatography to retain enzymatic activity and prohibit $Fe^{2+}$ oxidation, identifying that mutations in the CuZnSOD associated with a neurological disorder (amyotrophic lateral sclerosis) are also critical for calcineurin-CuZnSOD interaction, use of fluorescent labeled recombinant CuZnSOD and calcineurin to screen for CuZnSOD/calcineurin activators or inhibitors, use of fluorescent labeled RII-peptide and calcineurin to screen for calcineurin activators or inhibitors, identification of calcineurin/CuZnSOD inhibitors or activators by using the recombinant enzymes as affinity ligands to purify new drugs from natural sources, inclusion of all isoforms, all known and two newly identified splicevariants into the screening procedure, which allows the identification of less toxic and tissue specific drugs which are more suitable for the therapeutical treatment of different clinical indications.

The described features of the invention and further features result in greater detail from the examples in combination with the subclaims. The features could be realized in combination with each other or alone.

EXAMPLE

1. Cloning of CuZnSOD transcript from human brain poly-A-RNA—Cloning of human CuZnSOD was performed by reverse transcription PCR using human brain poly-A-RNA as template (Clontech, Palo Alto, Calif., USA). The oligonucleotides SODs1 5'-ttc cgt tgc agt cct cgg aac-3', SODas1 5'-taa ggg gcc tca gac tac atc-3', SOD-PQE60s2 5'-caa gcc atg gcg acg aag gcc gtg tgc gtg ctg-3', SOD-PQE60 as2 5'-gaa gat ctt tgg gcg atc cca att aca cca c-3', SOD-PQE30-s2 5'-cgc gga tcc gcg acg aag gcc gtg tgc gtg-3' and SOD-PQE30-as2 5'-ggg ttc gaa tta ttg ggc gat ccc aat tac-3' were supplied by Interactiva (Ulm, Germany). Reverse transcription was performed with the SODas1 primer and 100 ng of poly-A-RNA according to the manufacturer's protocol (Expand reverse transcriptase, Boehringer Mannheim, Germany). The human CuZnSOD cDNA was amplified by nested PCR. The first PCR was performed in 20 μl, using 0.5 μl reverse transcription product, 10 μM SODs1 and SODas1 primers, 300 μM dNTPs, 2 μl of the manufacturer's 10×PCR buffer and 2.5 U Taq-polymerase with 30 cycles of 1 min 95° C., 1 min 45° C., 1 min 72° C. followed by a second PCR (50 μl) with 5 μl of the purified first PCR product, 10 μM SOD-PQE60s2 and SOD-PQE60 as2 primers, 300 μM dNTPs, 5 μl of the manufacturer's PCR buffer and 2.5 U Taq-polymerase with 30 cycles of 1 min 95° C., 1 min 60° C., 1 min 72° C. (Taq-polymerase, Pharmacia Biotech, Uppsala, Sweden). For the subcloning into pQE30 expression vector the primers SOD-PQE30-s2 and SOD-PQE30-as2 were used instead of SOD-PQE60s2/SOD-PQE60as2.

2. Subcloning of human CuZnSOD into pQE60 expression vector (C-terminal fusion protein)—The SOD-pQE60 PCR product was purified by gel extraction prior to NcoI/BglII restriction (New England Biolabs). In order to generate a C-terminal histidine tag fusion protein the CuZnSOD transcript was ligated into the NcoI/BglII treated prokaryotic expression vector pQE60 (QIAexpress expression kit type IV and type ATG, Qiagen, Hilden, Germany). For selection, amplification and sequencing of the CuZnSOD vector construct (CuZnSOD-pQE60), A1 ligation product was transformed into E. coli M15[pREP4] cells (QIAexpress expression kit type ATG, Qiagen, Hilden, Germany). Correct reading frames and exclusion of mismatches were confirmed by radioactive and automated sequencing on both strands (T7-sequencing kit, Pharmacia Biotech, Uppsala, Sweden; ABI 377 sequencer, Applied Biosystems, USA).

3. Subcloning of human CuZnSOD into pQE30 expression vector (N-terminal fusion protein)—The SOD-pQE30 PCR product was purified by gel extraction prior to direct ligation into the pCR2.1 vector according to the manufacturer's protocols (TA-Cloning Kit, Invitrogen, De Schelp, Netherlands). After amplification and plasmid purification the pCR2.1-CuZnSOD vector construct was restricted with BamHI to yield a CuZnSOD transcript extended at the 3'-end with the sequence 5'-GAATTCCAGCACACTGGCGGCCGTTACTAGTGGATCC-3' which originates from PCR2.1 vector and includes additional EcoRI/BstX-I/SpeI/BamHI restriction sites. In order to generate a N-terminal histidine tag fusion protein the extended transcript was ligated into the BamHI/HindIII treated prokaryotic expression vector pQE30 (QIAexpress expression kit type IV, Qiagen, Hilden, Germany), blunted by incubation with Klenow-DNA-polymerase and circularized by a second treatment with T4-DNA-Ligase (Boehringer Mannheim, Germany). For selection, amplification and sequencing of the CuZnSOD vector construct (CuZn-SOD-pQE30), 10 μl ligation product was transformed into E. coli M15[pREP4] cells (QIAexpress expression kit type IV and type ATG, Qiagen, Hilden, Germany). Correct reading frames and exclusion of mismatches were confirmed by radioactive and automated sequencing on both strands (T7-sequencing kit, Pharmacia Biotech, Uppsala, Sweden; ABI 377 sequencer, Applied Biosystems, USA).

4. Site directed mutagenesis (point mutations associated with the neurological disorder Amyotrophic Lateral Sclerosis and important for calcineurin/CuZnSOD protein interaction)—Amino acid substitutions were introduced according to the manufacturer's protocol, using the primers SOD-PQE60-A4V (5'-caa gcc atg gcg acg aag gtc gtg-3'), SOD-A4V (5'-tcb gcg acg aag qtc gtg tgc gtg ctg-3'), SOD-G37R (5'-gg aag catt aaa aga ctg act gaa ggc-3'), SOD-D90A (5'-aat gtg act gct gcc aaa gat ggt gtg-3'), SOD-G93A (5'-gct gac aaa gat gct gtg gcc gat gtg-3'), SOD-AflIII (5'-acg cag gaa aga aca tgt gag caa aag-3'), SOD-BglII (5'-acg cag gaa aga aga tct gag caa aag-3') and the expression vector CuZnSOD constructs CuZn-SOD-pQE30 and CuZnSOD-pQE60, respectively (Chameleon site directed mutagenesis kit, Stratagene, San Diego, Calif., USA). Incorporation of the site-directed mutations was confirmed by DNA sequencing of the expression vector. Site directed mutagenesis yielded eight additional vector sequences corresponding to eight protein sequences with clinical relevant amino acid substitutions:

| Vector-construct | amino acid subst. (pos. in protein) | nucleic acid subst. (pos. in sequ. prot.) |
|---|---|---|
| CuZnSOD-pQE60 | WT = wild-type | = SEQ ID NO 15 |
| CuZnSOD-pQE60-(A4V) | Ala-4 -> Val-4 | c-128 -> t-128 |
| CuZnSOD-pQE60-(G37R) | Gly-37 -> Arg-37 | g-226 -> a-226 |
| CuZnSOD-pQE60-(D90A) | Asp-90 -> Ala-90 | a-386 -> c-386 |
| CuZnSOD-pQE60-(G93A) | Gly-93 -> Ala-93 | g-395 -> c-395 |
| CuZnSOD-pQE30 | WT = wild-type | = SEQ ID NO 13 |
| CuZnSOD-pQE30-(A4V) | Ala-4 -> Val-4 | c-161 -> t-161 |
| CUZnSOD-pQE30-(G37R) | Gly-37 -> Arg-37 | g-259 -> a-259 |
| CUZnSOD-pQE30-(D90A) | Asp-90 -> Ala-90 | a-419 -> c-419 |
| CuZnSOD-pQE30-(G93A) | Gly-93 -> Ala-93 | g-428 -> c-428 |

5. Recombinant expression and purification of wild-type and mutated CuZnSOD—The CuZnSOD-pQE60 or CuZnSOD-pQE30 vector transformed E. coli M15[pREP4] cells were plated on LB/ampicillin (100 μg/ml)/kanamycin (25 μg/ml) agar. Expression cultures were grown in 250 ml LB/ampicillin (100 μg/ml)/kanamycin (25 μg/ml) until the $OD_{600}$ was 0.6. Constitutive leakage expression of human CuZnSOD was fully prevented by the repressor plasmid pREP4-lacI. Production of the human CuZnSOD fusion proteins was induced by addition of IPTG (1 mM). After two hours the bacterial cells were harvested by centrifugation (4000 g, 20 min), resuspended in 8 ml buffer A (20 mM Tris-HCl pH 7.9, 5 mM imidazole, 500 mM NaCl) and homogenized by three freeze thaw cycles and sonication on ice (Bandelin sonoplus GM70, 300 W, 3×10 sec). The lysate was centrifuged (10.000 g, 20 min) and incubated with 750 μl CuZn-NTA (nitrilotriacetat)-agarose for batch affinity binding for 1 h at 4° C. (Qiagen expressionist kit, Qiagen, Hilden, Germany). CuZn-NTA-agarose was prepared from Ni-NTA-agarose (Qiagen expressionist kit, Qiagen, Hilden, Germany) by subsequent washes in:
1) 2 volumes of bidistilled water
2) 3 volumes of regeneration buffer (6 M guanidiniumhydrochloride, 0.2 M acetic acid)
3) 5 volumes bidistilled water
4) 3 volumes 2% SDS
5) 1 volume 25% ethanol
6) 1 volume 50% ethanol
7) 1 volume 75% ethanol
8) 5 volumes 100% ethanol
9) 1 volume 75% ethanol
10) 1 volume 50% ethanol
11) 1 volume 25% ethanol
12) 1 volume bidistilled water
13) 5 volumes 100 mM Na-EDTA pH 8.0
14) 5 volumes bidistilled water
15) 2 volumes 100 mM CUSO4/100 mM ZnSO4 1 mM reduced glutathione/1 mM dithiothreitol
16) 2 volumes bidistilled water
17) 2 volumes regeneration buffer (6 M guanidiniumhydrochloride, 0.2 M acetic acid)
18) 2 volumes buffer buffer A2 (20 mM Tris-HCl pH 7.9, 5 mM imidazole, 500 mM NaCl, 200 μM CuSO4/200 μM ZnSO4/1 mM reduced glutathione/1 mM dithiothreitol.

The batch was applied to a 30 ml chromatography column, washed with 15 ml buffer A (20 mM Tris-HCl pH 7.9, 5 mM imidazole, 500 m.M NaCl) and subsequently with 8 ml buffer B (20 mM Tris-HCl pH 7.9, 60 mM imidazole, 500 mM NaCl). C-terminal or N-terminal histidine tagged CuZnSOD was eluted three times with 1.2 ml buffer C (10 mM Tris-HCl, 500 mM imidazole, 250 mM NaCl). Purity and correct expression products were checked by immunoblotting or N-terminal protein sequencing after separation of 20 μl eluate in SDS-PAGE (discontinuous 12.5% SDS-PAGE). To examine the protein levels in bacterial culture all CuZnSOD variants were induced synchronously at $OD_{600}$= 0.6 With 1 mM IPTG. After 1 h, 2 h, 3 h, 4 h and 20 h, aliquots (1 ml) of E. coli cultures were taken, centrifuged and homogenized in buffer A as described. The pellet was resuspended in 1 ml $H_2O$. Subsequently, 20 pl of the supernatant (soluble fractions) or 20 μl of the sonicated pellet suspension (insoluble fractions) were mixed with 7 μl of denaturing sample buffer (10% SDS, 10% mercaptoethanol, 20% glycerol, 130 mM Tris-HCl pH 6.8, 0.03% bromphenol blue). The samples were heated for 2 minutes at 80° C. and analyzed by 12% SDS-PAGE. After coomassie staining, the electropherograms were digitized with a CCD camera (Gel Doc 1000, BioRAD) and analyzed by densitometry using NIH-Image software (1.61).

6. Processing of CuZnSOD—In order to remove the nonphysiological histidine tag and to yield CuZnSOD useful for clinical applications the N-terminal histidin tagged CuZnSOD was proteolytically processed with cathepsin-C or the C-terminal variant was processed with carboxypeptidase-A according to the manufacturer's protocols (Boehringer-Mannheim, Mannheim, Germany). Treatment with cathepsin-C yielded a processed CuZnSOD starting with the amino acids $NH_2$-GSAT KAVCVLKGDGP (indicated in sequence protocol CuZnSOD-pQE30 SEQ ID NO 13). C-terminal fusion protein was yielded the C-terminal amino acid sequence VIGIAQR-COOH (indicated in sequence protocol CuZnSOD-pQE30 SEQ ID NO 13). Verification was done by peptide sequencing.

7. Reactivation of CuZnSOD—In order to yield physiologically relevant active homodimeric CuZnSOD, the CuZn-NTA eluate was ultrafiltered through a 5 kD membrane (omegacell, Filtron, Northborough, Mass., USA). For buffer exchange the samples were washed three times in reconstitution buffer (50 mM sodium citrate pH 5.5, 1 mM DTT). The protein solutions were incubated at 8° C. for 7 days (250 μg/ml protein). After distinct time intervals aliquots of the refolding mixture were either analyzed by native gel electrophoresis (2.6 μg CuZnSOD) and activity staining or assayed in a spectrophotometer (0.5–1 Ag CuZnSOD, superoxide dismutase assay kit, Calbiochem, San Diego, Calif., USA). For visualization of protein bands native gels were stained with coomassie blue. For the production of larger CuZnSOD amounts M15-E. coli cells were subsequently grown in 15 ml, 200 ml, 2500 ml and 20 L flasks. Refolded CuZnSOD proteins were dialyzed against 100 volumes of buffer D (10 mM Tris-HCl 0.1% Saccharose) and lyophilized.

8. SOD assay and activity staining—Enzymatic activity of the CuZnSOD proteins were either analyzed by 10% native gel electrophoresis and activity staining with nitrotetrazolium blue dye or by a quantitative spectrophotometrically assay according to published protocols (Beauchamp and Fridovich, 1971; Nebot et al., 1993). Protein yields were determined by the Bradford method (Protein assay kit, BioRAD, Hercules, Calif., USA). The concentration of purified CuZnSOD was determined spectrophotometrically using the extinction coefficient 265=$1.84 \times 10^4$ $M^{-1}$ $cm^{-1}$.

9. Subcloning of human CuZnSOD into pEGFP eukaryotic expression vector and generation of stable transfected PC12 cells (C-terminal fusion protein with enhanced green fluorescent protein as a fluorescent marker/label)—Using 10 μM of the primers SOD-pEGFP-s 5'-ccg cgg gcc cgc cat ggc gac gaa ggc cgt gtg cgt gc-3' and SOD-pEGFP-as 5'-gct cac cat ggt ggt ttg ggc gat ccc aat tac acc α-3', 10 ng CuZnSOD-pQE60 vector, 300 μM dNTPs, 5 μl of the manufacturer's PCR buffer and 2.5 U Taq-polymerase with 25 cycles of 1 min 95° C., 1 min 60° C., 1 min 72° C. (50 µl total volume, Taq-polymerase, Pharmacia Biotech, Uppsala, Sweden) a PCR product was generated which was cleaved by ApaI/NcoI digestion. The purified PCR product was ligated into ApaI/NcoI treated pEGFP—N3 vector (Clontech Laboratories, Palo Alto, Calif., USA). After amplification in XL2-Blue cells (25 µg/ml kanamycin) and plasmid purification the CuZnSOD-pEGFP vector construct was transfected into PC12 rat adrenal pheochromocytoma cells using the CalPhos™ Transfection Kit according to the manufacturer's protocols (Clontech Laboratories, Palo Alto, Calif., USA). Stable transfected CuZnSOD-pEGFP clones were selected by fluorescence microscopy (exitation 488 nm/emission 520 nm, MRC 1024 confocal microscope, BioRAD Laboratories, Hercules, Calif., USA).

10. Cloning of the regulatory subunit human calcineurin-B—Cloning of human calcineurin-B was performed by reverse transcription PCR using human brain poly-A-RNA as template (Clontech, Palo Alto, Calif., USA). The oligonucleotides CNBa-s1 5'-ccg ccg acc cgc cga gca-3', CNBa-as1 5'-ggt act ctc tga taa gag-3', CNBa-s3 5'-gga att ccc cgg gga aag agg aga aat taa cta tgg gaa atg agg caa gtt atc-3', CNBa-as2 5'-ttc cgg gcc caa gct tct aat taa tca cac atc tac cac cat c-3' were supplied by Interactiva (Ulm, Germany). Reverse transcription was performed with the CNBa-as1 primer and 100 ng of poly-A-RNA according to the manufacturer's protocol (Expand reverse transcriptase, Boehringer Mannheim, Germany). The human calcineurin-B cDNA was amplified by nested PCR. The first PCR was performed in 20 µl, using 0.5 µl reverse transcription product, 10 µM CNBa-s and CNBa-as1 primers, 300 µM dNTPs, 2 µl of the manufacturer's 10×PCR buffer and 2.5 U Pfu-polymerase with 20 cycles of 1 min 95° C., 1 min 55° C., 2 min 72° C. followed by a second PCR (50 µl) with 5 µl of the purified first PCR product, 10 µM CNBa-s3 and CNBa-as2 primers, 300 µM dNTPs, 5 µl of the manufacturer's PCR buffer and 2.5 U Pfu-polymerase with 20 cycles of 1 min 95° C., 1 min 55° C., 1 min 72° C. (Pfu-polymerase, Stratagene, San Diego, Calif., USA).

11. Cloning of the catalytic subunit human calcineurin-A-Alpha and splice variants—Cloning of human calcineurin-A-alpha was performed by reverse transcription PCR using human brain poly-A-RNA as template (Clontech, Palo Alto, Calif., USA). The oligonucleotides CNAa-s1 5'-gcg tcg ctg tcc tcc ggc agc-3', CNAa-as1 5'-gtg aac agg aag tgg tca ctg-3', CNAa-s2 5'-cat gcc atg gatc cat gtc cga gcc caa ggc-3', CNAa-as4 5'-tcc ccc cgg ggta ccc tag tta atc act gaa tat tgc tgc tat tac-3' were supplied by Interactiva (Ulm, Germany). Reverse transcription was performed with the CNAa-as1 primer and 100 ng of poly-A-RNA according to the manufacturer's protocol (Expand reverse transcriptase, Boehringer Mannheim, Germany) The human calcineurin-A-Alpha cDNA was amplified by nested PCR. The first PCR was performed in 25 µl, using 0.5 µl reverse transcription product, 10 µM CNAa-s1 and CNAa-as1 primers, 200 µM dNTPs, 2.5 µl of the manufacturer's 10×PCR buffer and 1.25 U Pfu-polymerase with 30 cycles of 40 seconds at 95° C., 40 seconds at 55° C., 3 min 72° C. followed by a second PCR (25 µl) With 2.5 µl of the purified first PCR product, 10 µM CNAa-s2 and CNAa-as2 primers, 200 µM dNTPs, 2.5 µl of the manufacturer's PCR buffer and 2.5 U Pfu-polymerase with 25 cycles of 40 seconds at 95° C., 40 seconds at 55° C., 3 min 72° C. (Pfu-polymerase, Stratagene, San Diego, Calif., USA).

Hereby a new splice variant was identified, which is important for calcium regulation and proteolytic regulation of calcineurin-A. The splice variant lacks the hole catalytic phosphatase domain and part of calcineurin-binding-site (Elimination of nucleic bases 208–1317 in sequence protocol CNAa1-pQE30 SEQ ID NO 17). The corresponding vector is named CNAa3-pQE30:

Location/Qualifiers
151 . . . 606/note="splicevariant: Calcineurin A alpha 1 lacking phosphatase domain, newly generated N-terminus exhibits protease activity"
115 . . . 150/note="His-Tag"
649 . . . 1161/note="Calcineurin B;Calcineurin B alpha $Ca^{2+}$ binding"

12. Cloning of the catalytic subunit human calcineurin-A-Beta and splice variants—PCR was performed as described under 11. with the exception that the primers CNAb-s1 5'-gag cct agc cga gcc ccg gg-3' and CNAb-as1 5'-ctg gga agt agt ggg tca ctg-3' were used for the first PCR and the primers and CNAb-s2 5'-cat gcc atg gat cca tgg ccg ccc cgg agc c-3' and CNAb-as4 5'-tcc ccc cgg ggt acc cta gtt aat cac tgg gca gta tgg ttg cca g-3' were used for second PCR.

13. Cloning of the catalytic subunit human calcineurin-A-Gamma and splice variants—PCR was performed as described under 11. with the exception that the primers CNAg-s1 5'-gga gcC tgg agg agg ccg ag-3' and CNAg-as1 5'-cgg cag gac tct aag tca tga-3' were used for the first PCR and the primers and CNAg-s2 5'-cat gcc atg gat cca tgt ccg gga ggc gct tc-3' and CNAg-as4 5'-tcc ccc cgg ggt acc cta gtt aat cat gaa tqg gct ttc ttc cct t-3' were used for second PCR.

Hereby a new splice variant was identified, which is important for calcium regulation and proteolytic regulation of calcineurin-A. The splice variant with human exon is not yet available in gene database (substitution of nucleic bases 1474–1503 in sequence protocol CNAg2-pQE30 SEQ ID NO 32) with 5'-ACA GTA GAA GCG GTA GAG GCC CGG GAA GCC-3' (corresponding peptide: NH2-TVEAVEAREA-COOH). The corresponding vector is named CNAg3-pQE30.

| Location/Qualifiers | |
|---|---|
| 115 . . . 150 | /note = "His-Tag" |
| 151 . . . 1689 | /note = "Calcineurin-A-Gamma-2" |
| 1474 . . . 1503 | /note = "human brain calcineurin-A-gamma alternative exon = interaction domain with cytoskelett, death-domain homolog, stomatin homolog" |
| 1690 . . . 1731 | /note = "RBS&MCS2" |
| 1732 . . . 2244 | /note = "Calcineurin-B" |

14. Subcloning of calcineurin-B and calcineurin-A variants into pQE30—For the recombinant expression in procaryotic cells calcineurin-B was subcloned with either calcineurin-A-alpha1, calcineurin-A-alpha2, calcineurin-A-beta1, calcineurin-A-beta2, calcineurin-A-gamma1 or calcineurin-A-gamma2. The purified calcineurin-A-alpha, calcineurin-B-alpha or calcineurin-A-gamma PCR products (described in 11.–13.) were restricted with BamHI/XmaI. The purified calcineurin-B product (described in 10.) was restricted with XmaI/HindIII and ligated together with the respective calcineurin-A-fragment into the BamHI/HindIII treated vector pQE30 to yield the final procaryotic expression vector constructs CNAa1-pQE30, CNAa2-pQE30, CNAa3-pQE30, CNAb1-pQE30, CNAb2-pQE30, CNAg1-pQE30, CNAg2-pQE30 and CNAg3-pQE30.

15. Recombinant coexpression and purification of calcineurin-B/calcineurin-A heterodimers with CuZnSOD—CNAa1-pQE30, CNAa2-pQE30, CNAa3- pQE30, CNAb1-pQE30, CNAb2-pQE30, CNAg1-pQE30, CNAg2-pQE30 or CNAg3-pQE30 were transformed into *E. coli* M15[pREP4][CuZnSOD-pQE30] to yield cells able to coexpress calcineurin-A, calcineurin-B and CuZnSOD. cells were plated on LB/ampicillin (100 µg/ml)/kanamycin (25 µg/ml) agar. Expression cultures were grown in 250 ml LB/ampicillin (100 µg/ml)/kanamycin (25 µg/ml) until the $OD_{600}$ was 0.6. Constitutive leakage expression was prevented by the repressor plasmid pREP4-lacI. Production of the human calcineurin-A/calcineurin-B histidine tagged heterodimers was induced by addition of IPTG (1 mM). After four hours the bacterial cells were harvested by centrifugation (4000 g, 20 min), resuspended in 8 ml buffer A (20 mM Tris-HCl pH 7.9, 5 mM imidazole, 500 mM NaCl) and homogenized by three freeze thaw cycles and sonication on ice (Bandelin sonoplus GM70, 300 W, 3×10 sec). The lysate was centrifuged (10,000 g, 20 min) and incubated with 750 µl Fe-NTA-agarose for batch affinity binding for 1 h at 4° C. (Qiagen expressionist kit, Qiagen, Hilden, Germany). Fe-NTA-agarose was prepared from Ni-NTA-agarose (Qiagen expressionist kit, Qiagen, Hilden, Germany) by subsequent washes in:
1) 2 volumes of bidistilled water
2) 3 volumes of regeneration buffer (6 M guanidiniumhydrochloride, 0.2 M acetic acid)
3) 5 volumes bidistilled water
4) 3 volumes 2% SDS
5) 1 volume 25% ethanol
6) 1 volume 50% ethanol
7) 1 volume 75% ethanol
8) 5 volumes 100% ethanol
9) 1 volume 75% ethanol
10) 1 volume 50% ethanol
11) 1 volume 25% ethanol
12) 1 volume bidistilled water
13) 5 volumes 100 mM Na-EDTA pH 8.0
14) 5 volumes bidistilled water
15) 2 volumes 100 mM $FeSO_4$/1 mM reduced glutathione 1 mM dithiothreitol/100 mM ascorbic acid
16) 2 volumes bidistilled water
17) 2 volumes regeneration buffer (6 M guanidiniumhydrochloride, 0.2 M acetic acid)
18) 2 volumes buffer buffer A3 (20 mM Tris-HCl pH 7.9, 5 mM imidazole, 500 mM NaCl, 200 gM $FeSO_4$/1 mM reduced glutathione/1 mM dithiothreitol/1 mM ascorbic acid.

The batch was applied to a 30 ml chromatography column, washed with 15 ml buffer A4 (20 m.M Tris-HCl pH 7.9, 5 mM imidazole, 500 mM NaCl/1 mM reduced glutathione/1 mM dithiothreitol/1 mM ascorbic acid) and subsequently with 8 ml buffer B (20 m.M Tris-HCl pH 7.9, 60 mM imidazole, 500 mM NaCl/1 mM reduced glutathion/1 mM dithiothreitol/1 mM ascorbic acid). N-terminal histidine tagged calcineurin-A/calcineurin-B heterodimer was eluted three times with 1.2 ml buffer C (10 mM Tris-HCl, 500 mM imidazole, 250 mM NaCl/1 mM reduced glutathion/1 mM dithiothreitol/1 mM ascorbic acid, buffer was degased and subsequently saturated with nitrogen). To prevent oxidation of calcineurin, the eluate was stored at −80° C. in nitrogen containing and oxygen free vials. Purity and correct expression products were checked by immunoblotting or N-terminal protein sequencing after separation of 20 µl eluate in SDS-PAGE (discontinuous 12, 5 SDS-PAGE).

16. Subcloning of human calcineurin-A-Alpha into pEGFP eukaryotic expression vector and generation of stable transfected PC12 cells (C-terminal fusion protein with enhanced green fluorescent protein as a fluorescent marker)—The vector CNAa2-pQE30 was digested with BamHI/XmaI to generate a sticky end CNAa2 fragment. The purified fragment was ligated into Bgl-II/XmaI treated pEGFP-Cl vector (Clontech Laboratories, Palo Alto, Calif., USA). After amplification in XL2-Blue cells (25 µg/ml kanamycin) and plasmid purification the CNAa-pEGFP vector construct was transfected into PC12 rat adrenal pheochromocytoma cells using the CalPhos™ Transfection Kit according to the manufacturer's protocols (Clontech Laboratories, Palo Alto, Calif., USA). Stable transfected CNAa-pEGFP clones were selected by fluorescence microscopy during a three month propagation procedure (exitation 488 nm/emission 520 nm, MRC 1024 confocal microscope, BioRAD Laboratories, Hercules, Calif., USA).

17. Subcloning of calcineurin-A-Beta into pEGFP—The same procedure as described in 16. was applied except that the CNAa2-pQE30 vector was substituted by CNAb2-pQE30 to generate CNAb-pEGFP.

18. Subcloning of calcineurin-A-Gamma into pEGFP—The same procedure as described in 16. was applied except that the CNAa2-pQE30 vector was substituted by CNAg2-pQE30 to generate CNAg-pEGFP.

19. Western blotting and protein sequencing—Transfer of purified proteins from 12% SDS-PAGE to PVDF membranes (Boehringer-Mannheim, Mannheim, Germany) was performed according to standard protocols using transfer buffer (48 mM Tris, 39 mM Glycine, 20% methanol, 1% SDS, pH 9.2) and following blotting conditions: 75 min at 25 V/110 mA. Blocking, washing and detection (HRP detection system) were performed according to the manufacturer's protocols (ECL kit, Amersham, Buckinghamshire, UK). An anti-human CuZnSOD antibody (1:5,000 dilution, rabbit polyclonal anti-human SOD1 antibody; BIOMOL, Hamburg, Germany) was used as primary antibody and an anti-rabbit IgG antibody (1:10,000 dilution) labeled with HRP was used as secondary antibody. For the detection of calcineurin-A (alpha, beta, gamma isoforms) a polyclonal calcineurin-A antibody was used as 1:5000 dilution (Sigma Aldrich, Deisenhofen, Germany). For N-terminal protein sequencing the PVDF membrane was soaked in 100% methanol. Proteins which seemed to be blocked by N-terminal posttranslational modifications were treated with acylamino-acid-peptidase according to the manufacturer's protocol (Boehringer-Mannheim, Mannheim, Germany). Coomassie brilliant blue stained bands were cut out. Automated Edman degradation of peptides was performed on an Applied Biosystems protein sequencer (476A).

20. Calcineurin phosphatase assay—100 ng–4 µg recombinant calcineurin (calcineurin-A/B heterodimer), 100 ng–1 µg purified bovine brain calcineurin (Sigma Aldrich, Deisenhofen, Germany) or 100 µg homogenized tissue or cell extracts were used for classical calcineurin phosphatase assays. 100 µg cells or tissue were homogenized exactly as described (Stemmer et al., 1995). Partly purified and redox sensitive calcineurin was prepared by centrifugation at 14,000 rpm at 4° C. for 10 min (Eppendorf centrifuge 5417R) and the resulting supernatant was separated on a 1.5×10 cm Sephadex-G50 gelfiltration column as described (Stemmer et al., 1995), (Gold et al., 1997). Phosphotyrosine phosphatase assay was performed in microplates (100 µl total assay volume) either using 30 µM fluoresceinmonophosphate or 20 mM para-nitrophenylphosphate (Sigma Aldrich, Deisenhofen, Germany); 10 µl recombinant, purified or partly purified and assay buffer (25 mM Tris/HCl, pH 7; 2 mM $CaCl_2$; 0.1 µM calmodulin; 25 µM FK506). After starting the enzymatic reaction with para-nitrophenylphosphate or fluoresceinmonophosphate the absorbance at 405 nm (para-nitrophenylphosphate) or fluorescence λ exication=485 nm; λ emission=520 nm) was monitored over 20 min at 30° C. using a UV/VIS/fluorescence microplate photometer (Biolumin 960 kinetic fluorescence/absorbance photometer, Molecular Dynamics). Phosphoserine phosphatase assay was performed as described (Hubbard and Klee, 1991), (Wang et al., 1996). In short: 40 µl recombinant or partly purified calcineurin was mixed with test buffer (40 mM Tris/Hcl pH 8; 0.1 M KCl; 0.4 mg/ml BSA; 0.67 mM DTT; 0.67 µM calmodulin; 1 µM FKBP binding protein; 0.5 µM ocadaic acid for inhibition of phophatase A1 and A2) and enzymatic reaction and calcium induced redox-inactivation of calcineurin started by addition of 20 µl substrate buffer (7.7 µM radioactive phosphorylated RII-peptid, 2.0 mM $CaCl_2$). The assay was performed in duplicates and the addition of 1 µM FK506 or cyclosporine was used to verify calcineurin activity for each reading point. The protective effect of CuZnSOD against redox inactivation of calcineurin was determined by addition of 3 µg recombinant human wild-type or mutated CuZnSOD (constant CuZnSOD protein) or addition of 1.67 units of recombinant human wild-type or mutated CuZnSOD (constant CuZnSOD activity). The reaction mixture was incubated for 2 min at 30° C. and stopped with 100 mM potassium phosphate/5% TCA. The reaction mixture was passed through a 0.5 ml ion-exchange column (Dowex; AG 50W-X8, BioRad) and the unbound phosphate eluted with 0.5 ml water. The quantity of released phosphate was determined by a scintillation counting.

An enzymatic protein phosphatase assay was established using the nonphysiological substrate fluoresceinmonophosphate (FMP). Assuming a Michaelis-Menten kinetic for FMP and using the Lineweaver-Burk method for analysis of kinetic data a $K_M$ of 40 µM and a $V_{max}$ of 400 µmol/min was determined. The assay was applicable to calcineurin and magnesium dependent proteinphosphatase 2C (data not shown, (Grothe et al., 1998)). The enzymatic activity is linear in the range of 12.5 pM to 75 pM calcineurin. FMP is more sensitive than para-nitrophenylphosphate (pNPP). Neither FMP nor pNPP are useful to measure calcineurin activity in crude preparations by inhibition with the immunsuppressive drugs FK506 or cyclosporine (cell homogenate, partly purified calcineurin). Both substrates also failed to measure calcium induced redox-inactivation of calcineurin or CuZnSOD mediated protection of this inactivation. The inhibition assay also failed when calcium was substituted against other divalent cations ($Ni^{2+}$, $Mg^{2+}$). Only the physiological relevant substrate could be used in an immunsuppressive drug inhibitory assay (RII-peptide phosphopeptide). In the classic radioactive assay 95% inhibition with 1 µM FK506 or cyclosporine was determined. It is concluded that inhibition of calcineurin activity by immunosuppresive drugs needs larger molecular weight substrates than pNPP and FMP. Furthermore it is concluded that redoxsensitivity is linked to phosphoserine phosphatase activity and therefore not detectable with phosphotyrosine analoges like pNPP or FMP. The recombinant human wild-type CuZnSOD and purified human erythrocyte CuZnSOD (Sigma Aldrich, Deisenhofen, Germany) were effective to protect 50–100% of calcineurin after calcium induced redox inactivation. Mutated CuZnSOD proteins, associated with the severe neurological disorder amyotrophic lateral sclerosis, were less effective to protect calcineurin against redox inactivation.

Protective Effect of CuZnSOD of Calcium Induced Inactivation of Calcineurin

Percentage of FK506 inhibitable RII-phosphopeptide activity after 20 min compared with the activity at 0 min

| human CuZnSOD | constant protein (3 µg) | constant activity (1.67 U) |
|---|---|---|
| erythrocyte wild-type (8330 U/mg) | 57 +/– 10% | 57 +/– 10% |
| recombinant wild-type (6380 U/mg) | 70 +/– 33% | 56 +/– 22% |
| recomb. mutation D90A (4590 U/mg) | 42 +/– 17% | 32 +/– 15% |
| recomb. mutation G93A (2130 U/mg) | 16 +/– 16% | 21 +/– 22% |
| recomb. mutation A4V (1820 U/mg) | 22 +/– 27% | 8 +/– 3% |
| control (no CuZnSOD) (0 U/mg) | 9 +/– 7% | 9 +/– 7% |

The protective effect does not depend on CuZnSOD activity since higher protein amounts of mutated CuZnSOD corresponding to a higher enzymatic activity were even less effective in protection of calcineurin.

Therefore it is concluded that amino acid substitutions, associated with familial amyotrophic lateral sclerosis, are important for the protein interaction of calcineurin and CuZnSOD and therefore are involved in the CuZnSOD mediated protection of calcium induced redox inactivation of calcineurin. Since this protective effect is disturbed in amyotrophic lateral sclerosis and protection of calcineurin by CuZnSOD it may also be important in other neurological and cardiovascular diseases (Alzheimer, Parkinson, epilepsy, ischemia, heart-failure).

An high-throughput bioassay was developed to detect and isolate artificial or endogenous drugs enhancing (activators) CuZnSOD-calcineurin interaction and therefore protecting calcineurin against redox-inactivation or drugs reducing (inhibitors) CuZnSOD-calcineurin interaction and therefore inhibit calcineurin activity. Inhibitors are useful to substitute toxic immunsuppressive drugs like FK506 or cyclosporine. Activators and inhibitors may be useful for the therapeutical treatment of amyotrophic lateral sclerosis, Parkinson, Alzheimer, epilepsy, ischemia and cardiovascular diseases.

21. High Throughput BioAssay using recombinant calcineurin-A, recombinant calcineurin-B, calmodulin and recombinant CuZnSOD (analytical assay to identify activators or inhibitors of CuZnSOD/calcineurin interaction)—Laser fluctuation correlation spectroscopy (FCS) is a useful tool to quantify ligand—ligand interactions. The fluorescence F(t) of a optical well defined volume element which is excitated by a confocal laser is monitored as a function of time. The temporal autocorrelation of the fluorescence fluctuation δ F(t) yields the time scale of this dynamics and the average number of independent fluorophores in the probe volume. If the fluoresence fluctuation arise from diffusive motion and from fluorescence sensitive reaction, fluorescent fluctuation correlation function signal is approximated by the formula:

$$G_{DR}(\tau)=G_{Dif}(\tau)*[1+A*\exp(-k_R*\tau)]$$

τ=fluorescence correlation time $k_R$=apparent binding constant of the fluorescent labeled ligand A=equilibrium coefficent dependent constant If one measurement is performed with a solution only containing the fluorescent labeled ligand and a second measurement is performed with a solution containing the fluorescent labeled ligand and an interacting molecule the correlation function $G_{DR}$ can be separately analyzed and yields binding parameters of the interacting molecules. Upon binding of the ligand to the interacting molecule the hydrodynamic radius increases and therefore the diffusion coefficient decreases resulting in a longer correlation time.

A fluorescence labeled recombinant CuZnSOD as a fluorescent label was used to monitor the binding dynamics to calcineurin. CuZnSOD was labeled with Oregon-Green-514 dye according to the manufacturer's protocols (FluoReporter Protein labeling Kit, Molecular Probes, Leiden, Netherlands). The amount of fluorescent dye labels per CuZnSOD dimer was quantified by determining the ratio of the absorbance at 265 nm (CuZnSOD protein)/514 nm (Oregon-dye). The diffusion constant and 110 correlation time of the labeled CuZnSOD (100 nM) was measured on a bovine serum albumin treated glass plate with an confocal laser microscope attached to an autocorrelator ($\lambda$ excitation= 488 nm, $\lambda$ emission=511 nm) in 10 $\mu$l assay buffer containing 50 mM sodiumphosphate pH 7.1, 150 mM NaCl, 0.67 mM DTT, 0.67 $\mu$M calmodulin, 0.67 mM $CaCl_2$, 1 mM $MgCl_2$. The beam from a modelocked Ti:Sa or cw argon ionlaser was collimated to fill the back aperture of a immersion microscope objective (Zeiss C-Apochromat 63×1.2 w), producing a small diffraction limited spot. The emitting fluorescent light was collected by the same objective separated from the excitation light by a beamsplitter/filter combination and imaged first to a variable pinhole and than to the detector (Avalanche Photodiode EG&G SPCM AQ161 or PMT Hamamatsu R5600-03). The labeled CuZnSOD exhibited an autocorrelation time corresponding to a hydrodynamic radius of 41,000 Dalton which is comparable to the expected molecular weight of the homodimer (34,600 Dalton). Next 0.2 $\mu$l calcineurin-A/B heterodimer (5 $\mu$M) was added to a labeled CuZnSOD mixture and the fluorescence correlation signal was determined. The hydrodynamic radius increases from 41 kDa to 90 kDa indicating that approximatly one calcineurin heterodimer interacts with one CuZnSOD dimer (expected: 114 kDa). Using mutated D90A CuZnSOD yielded an apparent molecular weight of 180.000 kDa indicating the formation of calcineurin/CuZnSOD aggregates. The apparent binding constant between human wild-type CuZnSOD and calcineurin was estimated as $kD=2\times10^{-6}$ M+/$-1\times10^{-6}$ M. It is concluded that laser correlation spectroscopy is useful to perform a ultra high throughput screening for ligands diminishing the CuZnSOD/calcineurin interaction which simply can be monitored by a reduction of the autocorrelation time after addition of a potential drugs. It is possible to screen for suitable substances using substances available in chemical, peptide or natural compound screening libraries.

22. High Throughput BioAssay using recombinant calcineurin-A, recombinant calcineurin-B, calmodulin and RII-Fluophos (analytical assay to identify activators or inhibitors of calcineurin)—RII peptide was synthesized according to standard peptide synthesis protocols ((Blumenthal et al., 1988); Interactiva, Ulm, Germany). To generate a fluorescent labeled peptide which furthermore contains a phosphoester at Ser-15, amino acid residue Ser-15 was coupled with fluorescein-phosphoamidit (FluoreDite Labeling Reagent, Perspective Biosystems), which is usually used for labeling of nucleotides, to yield RII-Fluophos (Interactiva, Ulm, Germany). The expected molecular weight (2578.8 Dalton) was confirmed by mass spectrometry (2580.6 Dalton). The Fluophos-RII-peptide was not converted by calcineurin as was monitored by fluorescence spectrometrie (Biolumin 960 UV-/VIS/fluorescence microplate reader). Therefore Fluophos-RII-peptide was used in laser fluorescence correlation spectroscopy as described in paragraph 20 except that $\lambda_{excitation}$ was 488 nm and $\lambda_{emission}$ was 520 nm. Furthermore, labeled CuZnSOD was substituted by 10 nM Fluophos-RII-peptide yielding a hydrodynamic radius corresponding to 4 kDa (expected 2.6 kDa). After calcineurin addition the molecular weight increases to 100.000 kDa and a binding constant of $Kd=0.6\times10^{-6}$ M is estimated. Binding constants were comparable between the six calcineurin isoforms/splice variants. It is concluded that laser correlation spectroscopy is useful to perform a ultra high throughput screening for ligands directly substrate binding to calcineurin by simply monitoring the autocorrelation time after addition of potential drugs. By descriminating the binding properties of potential drugs to the six different heterodimer combinations (calcineurin-A-alpha1/calcineurin-B, calcineurin-A-alpha2/calcineurin-B, calcineurin-A-beta1/calcineurin-B, calcineurin-A-beta2/calcineurin-B, calcineurin-A-gamma1/calcineurin-B, calcineurin-A-gamma2/calcineurin-B) it is possible to identify tissue specific and therefore less toxic calcineurin inhibitors.

It is possible to combine the screening procedures described in paragraph 20 and 21 strategically: substances which are able to inhibit the calcineurin-CuZnSOD interaction (positive hit in paragraph 20) but failed to show an effect in procedure 21 (negative hit) are predominantly positive candidates for the therapeutical use in neurological disorders because a toxic immunosuppressive side effect is less probable. Substances which fail to inhibit the calcineurin-CuZnSOD interaction (negative hit) but show an effect in procedure 21 (positive hit) are predominantly positive candidates for immunosuppression. Substances effective in both procedures are likely to be toxic.

23. Cellular BioAssay using eucaryotic cells transfected with calcineurin-A-EGFP fusionprotein or CuZnSOD-EGFP fusion protein—PC12 cells stably transfected with CuZnSOD and calcineurin isoenzymes serve as a model for monitoring the effects of CuZnSOD or calcineurin overexpression in neuronal cells. CuZnSOD reportedly has been implicated to be involved in the mediation of hypoxie tolerance, whereas calcineurin overexpression is associated with epileptogenesis, Parkinsonism or Alzheimers disease. It is possible to use theses cells subsequently to the identification of potential drugs in screening protocols 20 und 21. Toxicity of potential neuroprotective drugs and the effect on the subcellular distribution of calcineurin-isoforms or CuZnSOD, respectively can be monitored.

24. Pull-Down-BioAssay using histidine tagged recombinant CuZnSOD to purify CuZnSOD interacting ligands (Preparative assay to isolate activators or inhibitors of CuZnSOD/calcineurin interaction from biological sources)—Recombinant purified histidine tagged CuZnSOD in 50 mM sodiumphosphate buffer pH 8.0 was attached to CuZn-NTA magnetic agarose beads by incubating 100 $\mu$l beads suspension with 100 $\mu$l CuZnSOD solution (0.3 $\mu$g/$\mu$l) in 96 well microplates for 30 minutes at room temperature on a microplate shaker (600 rpm). CuZn-NTA magnetic beads were generated from Ni-NTA beads by applying the same procedure as described under paragraph 5 (Ni-NTA magnetic agarose beads, Qiagen, Hilden, Germany). The microplate was placed on the 96 well magnet for 1 minute and the supernatant removed from the wells.

Cytosolic ligands were isolated as follows: 200 $\mu$l interaction buffer (50 mM $NaH_2PO_4$, 300 mM NaCl, 20 mM imidazole pH 8.0, 0.1% Tween-80) were added to the CuZn-NTA agarose beads/CuZnSOD containig wells and placed on the 96 well magnet to remove interaction buffer.

100 mg tissue, cells or other biological specimen to be analyzed for CuZnSOD interacting ligands were homogenized in 200 µl lysis buffer (50 mM $NaH_2PO_4$, 300 mM NaCl, 10 mM imidazole pH 8.0, 0.1% Tween-80) using a dounce homogenizer. The lysate was cleared by 30 min centrifugation at 10,000 g at 4° C. The supernatant was applied to the wells containing CuZn-NTA absorbed recombinant human CuZnSOD, mixed and incubated for 60 minutes at 0° C. The microplate was placed on the 96 well magnet for 1 minute to remove the supernatant. After removal of the lysate the wells were washed twice by adding 200 µl interaction buffer. Elution of CuZnSOD and interacting ligands was achieved by addition of 100 µl elution buffer (50 mM $NaH_2PO_4$, 300 mM NaCl, 250 mM imidazole pH 8.0, 0.1% Tween-80).

Membranous ligands were isolated as follows: denaturing interaction buffer (6 M guanidine-HCL, 100 mM $NaH_2PO_4$ pH 8.0, 0.1% Tween-80) was added to the CuZn-NTA agarose beads/CuZnSOD containig wells and placed on the 96 well magnet to remove interaction buffer. The pellet from the procedure above was solubilized in 200 µl denaturing interaction buffer (6 M guanidine-HCL, 100 mM $NaH_2PO_4$ pH 8.0, 0.1% Tween-80) for 60 minutes at room temperature. The solubilisate was cleared by 30 min centrifugation at 10,000 g at room temperature. The supernatant was applied to the wells containing CuZn-NTA absorbed-recombinant human CuZnSOD, mixed and incubated for 60 minutes at room temperature. The microplate was placed on the 96 well magnet for 1 minute to remove the supernatant. The wells were washed once with 200 µl denaturing interaction buffer (6 M guanidine-HCL, 100 mM $NaH_2PO_4$ pH 8.0, 0.1% Tween-80) and a second time with 200 µl denaturing wash buffer (8 M Urea, 100 mM NaH2PO4 pH 8.0, 0.1% Tween-80). Elution of CuZnSOD and interacting ligands was achieved by addition of 100 µl denaturing elution buffer (8 M Urea, 100 mM $NaH_2PO_4$ pH 4.0, 0.1% Tween-80).

To remove low molecular weight ligands for HPLC analysis, the eluates (cytosolic or membranous) were ultrafiltered through a 5 kDa membrane as described under 7. Low molecular weight ligands were separated on a preparative reverse phase HPLC (UV detection at 200 nm). Homogeneity and molecular weight of UV detectable fractions were analyzed by mass spectrometry. High molecular weight ligands (ultrafiltration remainder) were separated on a 10% polyacrylamide gel and protein bands identified by sequencing or MALDI mass spectrometrie as described under 19. Interacting nucleic acid was analyzed by separating the membranous eluate on a 1% agarose gel and staining with ethidium bromide. Fluorescent bands were extracted from the agarose (Qiagen gel extraktion kit, Qiagen, Hilden, Germany) subjected to digestion with RsaI and subcloned into RsaI treated pQE30 vector for DNA sequencing.

25. Pull-Down-BioAssay using histidine tagged recombinant calcineurin-A and calcineurin-B to purify calcineurin interacting ligands (Preparative assay to isolate activators or inhibitors of CuZnSOD/calcineurin interaction from biological sources)—Isolation and identification of calcineurin interacting ligands was performed analogous to paragraph 24 with the exception that recombinant calcineurin-A/B heterodimer was attached to Fe-NTA magnetic agarose beads which were prepared as described under paragraph 15. Furthermore six different heterodimer combinations were used (calcineurin-A-alpha1/calcineurin-B, calcineurin-A-alpha2/calcineurin-B, calcineurin-A-beta1/calcineurin-B, calcineurin-A-beta2/calcineurin-B, calcineurin-A-gamma1/calcineurin-B, calcineurin-A-gamma2/calcineurin-B) to descriminate between isoenzyme and splice variant specific interaction partners.

LITERATURE

1. Ankarcrona, M., Dypbukt, J. M., Orrenius, S., and Nicotera, P. (1996). FEBS Lett. 394, 321–324.
2. Beauchamp, C. and Fridovich, I. (1971). Anal. Biochem. 44, 276–287.
3. Blumenthal, D. K., Charbonneau, H., Edelman, A. M., Hinds, T. R., Rosenberg, G. B., Storm, D. R., Vincenzi, F. F., Beavo, J. A., and Krebs, E. G. (1988). Biochem. Biophys. Res. Commun. 156, 860–865.
4. Butcher, S. P., Henshall, D. C., Teramura, Y., Iwasaki, K., and Sharkey, J. (1997). J. Neurosci. 17, 6939–6946.
5. Enz, A., Shapiro, G., Chappuis, A., and Dattler, A. (1994). Anal. Biochem. 216, 147–153.
6. Gold, B. G., Zeleny-Pooley, M., Wang, M. S., Chaturvedi, P., and Armistead, D. M. (1997). Exp. Neurol. 147, 269–278.
7. Griffith, J. P., Kim, J. L., Kim, E. E., Sintchak, M. D., Thomson, J. A., Fitzgibbon, M. J., Fleming, M. A., Caron, P. R., Hsiao, K., and Navia, M. A. (1995). Cell 82, 507–522.
8. Grothe, K., Hanke, C., Momayezi, M., Kissmehl, R., Plattner, H., and Schultz, J. E. (1998). J. Biol. Chem. 273, 19167–19172.
9. Guerini, D. (1997). Biochem. Biophys. Res. Commun. 235, 271–275.
10. Guerini, D. and Klee, C. B. (1989). Proc. Natl. Acad. Sci. U.S.A. 86, 9183–9187.
11. Guerini, D., Krinks, M. H., Sikela, J. M., Hahn, W. E., and Klee, C. B. (1989). DNA 8, 675–682.
12. Haddy, A. and Rusnak, F. (1994). Biochem. Biophys. Res. Commun. 200, 1221–1229.
13. Hashimoto, T., Kawamata, T., and Tanaka, C. (1998). Nippon. Yakurigaku. Zasshi. 111, 21–28.
14. Hubbard, M. J. and Klee, C. B. (1991). Molecular Neurobiology, A Practical Approach. J. Chad and H. Wheal, eds. (Oxford: IRL Press), pp. 135–157.
15. Ito, A., Hashimoto, T., Hirai, M., Takeda, T., Shuntoh, H., Kuno, T., and Tanaka, C. (1989). Biochem. Biophys. Res. Commun. 163, 1492–1497.
16. Kayyali, U.S., Zhang, W., Yee, A. G., Seidman, J. G., and Potter, H. (1997). J. Neurochem. 68, 1668–1678.
17. Kincaid, R. L., Giri, P. R., Higuchi, S., Tamura, J., Dixon, S. C., Marietta, C. A., Amorese, D. A., and Martin, B. M. (1990). J. Biol. Chem. 265, 11312–11319.
18. Klee, C. B. (1991). Neurochem. Res. 16, 1059–1065.
19. Klee, C. B., Draetta, G. F., and Hubbard, M. J. (1988). Adv. Enzymol. Relat. Areas. Mol. Biol. 61, 149–200.
20. Kuno, T., Takeda, T., Hirai, M., Ito, A., Mukai, H., and Tanaka, C. (1989). Biochem. Biophys. Res. Commun. 165, 1352–1358.
21. Ladner, C. J., Czech, J., Maurice, J., Lorens, S. A., and Lee, J. M. (1996). J. Neuropathol. Exp. Neurol. 55, 924–931.
22. Liu, J., Albers, M. W., Wandless, T. J., Luan, S., Alberg, D. G., Belshaw, P. J., Cohen, P., MacKintosh, C., Klee, C. B., and Schreiber, S. L. (1992). Biochemistry 31, 3896–3901.
23. Liu, J., Farmer, J. D. Jr., Lane, W. S., Friedman, J., Weissman, I., and Schreiber, S. L. (1991). Cell 66, 807–815.
24. Molkentin, J. D., Lu, J. R., Antos, C. L., Markham, B., Richardson, J., Robbins, J., Grant, S. R., and Olson, E. N. (1998). Cell 93, 215–228.
25. Mondragon, A., Griffith, E. C., Sun, L., Xiong, F., Armstrong, C., and Liu, J. O. (1997). Biochemistry 36, 4934–4942.

26. Moriwaki, A., Lu, Y. F., Hayashi, Y., Tomizawa, K., Tokuda, M., Itano, T., Hatase, O., and Matsui, H. (1996). Neurosci. Res. 25, 191–194.
27. Muramatsu, T. and Kincaid, R. L. (1993). Biochim. Biophys. Acta 1178, 117–120.
28. Nebot, C., Moutet, M., Huet, P., Xu, J. Z., Yadan, J. C., and Chaudiere, J. (1993). Anal. Biochem. 214, 442–451.
29. Nelson, P. A., Akselband, Y., Kawamura, A., Su, M., Tung, R. D., Rich, D. H., Kishore, V., Rosborough, S. L., DeCenzo, M. T., and Livingston, D. J. (1993). J. Immunol. 150, 2139–2147.
30. Perrino, B. A., Fong, Y. L., Brickey, D. A., Saitoh, Y., Ushio, Y., Fukunaga, K., Miyamoto, E., and Soderling, T. R. (1992). J. Biol. Chem. 267, 15965–15969.
31. Perrino, B. A., Ng, L. Y., and Soderling, T. R. (1995). J. Biol. Chem. 270, 340–346.
32. Stemmer, P. M., Wang, X., Krinks, M. H., and Klee, C. B. (1995). FEBS Lett. 374, 237–240.
33. Wang, X., Culotta, V. C., and Klee, C. B. (1996). Nature 383, 434–437.
34. Yakel, J. L. (1997). Trends. Pharmacol. Sci. 18, 124–134.
35. Yu, L., Golbeck, J., Yao, J., and Rusnak, F. (1997). Biochemistry 36, 10727–10734.

Content of Sequence Listing 1. eukaryotic expression vector CuZnSOD-EGFP (CuZnSOD-pEGFP) (DNA)
2. CuZnSOD (PRT)
3. EGFP (PRT)
4. eukaryotic expression vector EGFP-Calcineurin A alpha (CNAa-pEGFP) (DNA)
5. EGFP (PRT)
6. Calcineurin A alpha (PRT)
7. eukaryotic expression vector EGFP-Calcineurin A beta (CNAb-pEGFP) (DNA)
8. EGFP (PRT)
9. Calcineurin A beta (PRT)
10. eukaryotic expression vector EGFP-Calcineurin A gamma (CNAg-pEGFP) (DNA)
11. EGFP (PRT)
12. Calcineurin A gamma (PRT)
13. prokaryotic expression vector His-CuZnSOD (CuZnSOD-pQE30) (DNA)
14. CuZnSOD (PRT)
15. prokaryotic expression vector CuZnSOD-His (CuZnSOD-pQE60) (DNA)
16. CuZnSOD (PRT)
17. prokaryotic expression vector His-Calcineurin A alpha1-Calcineurin B (CNAa1-pQE30) (DNA)
18. Calcineurin A alpha1 (PRT)
19. Calcineurin B (PRT)
20. prokaryotic expression vector His-Calcineurin A alpha2-Calcineurin B (CNAa2-pQE30) (DNA)
21. Calcineurin A alpha2 (PRT)
22. Calcineurin B (PRT)
23. prokaryotic expression vector His-Calcineurin A beta1-Calcineurin B (CNAb1-pQE30) (DNA)
24. Calcineurin A beta1 (PRT)
25. Calcineurin B (PRT)
26. prokaryotic expression vector His-Calcineurin A beta2-Calcineurin B (CNAb2-pQE30) (DNA)
27. Calcineurin A beta2 (PRT)
28. Calcineurin B (PRT)
29. prokaryotic expression vector His-Calcineurin A gamma1-Calcineurin B (CNAg1-pQE30) (DNA)
30. Calcineurin A gamma1 (PRT)
31. Calcineurin B (PRT)
32. prokaryotic expression vector His-Calcineurin A gamma2-Calcineurin B (CNAg2-pQE30) (DNA)
33. Calcineurin A gamma2 (PRT)
34. Calcineurin B (PRT)
35. peptide RII (PRT)

What is claimed is:

1. A method for screening for a modulator of calcineurin enzymatic activity, characterized in that a direct interaction between mammalian calcineurin and mammalian Cu/Zn-superoxide dismutase is monitored, comprising the following steps
   formation of a complex comprising at least mammalian calcineurin and mammalian Cu/Zn-superoxide dismutase in the presence of at least one potential modulator,
   detecting an influence of the potential modulator by directly monitoring the complex formation.

2. The method according to claim 1, characterized in that the monitoring is performed by detection of labels.

3. The method according to claim 1, characterized in that the mammalian calcineurin and/or the mammalian Cu/Zn-superoxide dismutase carry labels, wherein the labels are enhanced green fluorescent protein.

4. The method according to claim 3, characterized in that mammalian calcineurin and/or mammalian Cu/Zn-superoxide dismutase are expressed as fluorescent proteins.

5. The method according to claim 1, characterized in that the monitoring of complex formation is performed by laser fluctuation correlation spectroscopy.

6. The method according to claim 1, characterized in that mammalian calcineurin and mammalian Cu/Zn-superoxide dismutase are coexpressed in cells, and that the complex formation is performed within the cell.

7. The method according to claim 1, characterized in that mammalian calcineurin and/or mammalian Cu/Zn-superoxide dismutase are expressed in cells, and that mammalian calcineurin and/or mammalian Cu/Zn-superoxide dismutase are isolated and/or purified before the complex formation is performed.

8. The method according to claim 7, characterized in that purification of mammalian calcineurin is achieved by ferro-nitrilotriacetat(NTA)-metal affinity chromatography.

9. The method according to claim 7, characterized in that purification of mammalian Cu/Zn-superoxide dismutase is achieved by copper/zinc-NTA-metal affinity chromatography.

10. The method according to claim 1, characterized in that in the complex formation step, calmodulin and/or calcium are present.

11. The method according to claim 1, characterized in that additionally a monitoring of the enzymatic activity is performed by analyzing the phosphatase activity of mammalian calcineurin.

12. The method according to claim 11, characterized in that the phosphatase activity is analyzed by the use of at least one substrate, which carries a label.

13. The method according to claim 12, characterized in that the substrate is a peptide characterized by the amino acid sequence
   Asp-Leu-Asp-Val-Pro-Ile-Pro-Gly-Arg-Phe-Asp-Arg-Arg-Val-Ser-Val-Ala-Ala-Glu.

14. The method according to claim 12, characterized in that the substrate is a peptide containing a residue labeled with fluoresceine.

15. The method according to claim 11, characterized in that the influence of the potential modulator on the enzymatic activity is detected separately from the influence of the potential modulator on the complex formation.

16. A method for screening of modulators of mammalian calcineurin activity, comprising:
   a) determining the interaction of a potential modulator with either mammalian calcineurin or mammalian Cu/Zn-superoxide dismutase as a partner,
   b) taking a potential modulator showing interaction with mammalian calcineurin or mammalian Cu/Zn-superoxide dismutase according to step a),
   c) determining the interaction of said modulator taken in step b), with the other partner, namely mammalian calcineurin or mammalian Cu/Zn-superoxide dismutase, respectively, and
   d) identifying the potential modulator showing interaction also according to step c).

17. The method according to claim 16, characterized in that mammalian calcineurin and/or mammalian Cu/Zn-superoxide dismutase comprises at least one tag.

18. The method according to claim 16, characterized in that mammalian calcineurin and/or mammalian Cu/Zn-superoxide dismutase is attached to a solid matrix.

19. The method according to claim 1, characterized in that said mammalian calcineurin is human calcineurin.

20. The method according to claim 19, characterized in that said human calcineurin is a combination of a calcineurin A subunit selected from the group consisting of A-α1, A-α2, A-β1, A-β2, A-γ1, and A-γ2, and calcineurin B.

21. The method according to claim 16, characterized in that said mammalian calcineurin is human calcineurin.

22. The method according to claim 21, characterized in that said human calcineurin is a combination of a calcineurin A subunit selected from the group consisting of A-α1, A-α2, A-β1, A-β52, A-γ1, and A-γ2, and calcineurin B.

* * * * *

SEQUENCE LISTING

```
<160> NUMBER OF SEQ ID NOS: 35

<210> SEQ ID NO 1
<211> LENGTH: 5184
<212> TYPE: DNA
<213> ORGANISM: Homo sapiens
<220> FEATURE:
<221> NAME/KEY: CDS
<222> LOCATION: (662)..(1123)
<223> OTHER INFORMATION: copper/zinc superoxide dismutase
<221> NAME/KEY: CDS
<222> LOCATION: (1124)..(1849)
<223> OTHER INFORMATION: enhanced green fluorescent protein

<400> SEQUENCE: 1
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
```

-continued

```
atttccaagt ctccacccca ttgacgtcaa tgggagtttg ttttggcacc aaaatcaacg      480
ggactttcca aaatgtcgta acaactccgc cccattgacg caaatgggcg gtaggcgtgt      540
acggtgggag gtctatataa gcagagctgg tttagtgaac cgtcagatcc gctagcgcta      600
ccggactcag atctcgagct caagcttcga attctgcagt cgacggtacc gcgggcccgc      660 c atg gcg acg aag gcc gtg tgc gtg ctg aag ggc gac ggc cca gtg cag      709
  Met Ala Thr Lys Ala Val Cys Val Leu Lys Gly Asp Gly Pro Val Gln
   1               5                  10                  15 ggc atc atc aat ttc gag cag aag gaa agt aat gga cca gtg aag gtg         757
Gly Ile Ile Asn Phe Glu Gln Lys Glu Ser Asn Gly Pro Val Lys Val
                 20                  25                  30 tgg gga agc att aaa gga ctg act gaa ggc ctg cat gga ttc cat gtt         805
Trp Gly Ser Ile Lys Gly Leu Thr Glu Gly Leu His Gly Phe His Val
         35                  40                  45 cat gag ttt gga gat aat aca gca ggc tgt acc agt gca ggt cct cac         853
His Glu Phe Gly Asp Asn Thr Ala Gly Cys Thr Ser Ala Gly Pro His
     50                  55                  60 ttt aat cct cta tcc aga aaa cac ggt ggg cca aag gat gaa gag agg         901
Phe Asn Pro Leu Ser Arg Lys His Gly Gly Pro Lys Asp Glu Glu Arg
 65                  70                  75                  80 cat gtt gga gac ttg ggc aat gtg act gct gac aaa gat ggt gtg gcc         949
His Val Gly Asp Leu Gly Asn Val Thr Ala Asp Lys Asp Gly Val Ala
                 85                  90                  95 gat gtg tct att gaa gat tct gtg atc tca ctc tca gga gac cat tgc         997
Asp Val Ser Ile Glu Asp Ser Val Ile Ser Leu Ser Gly Asp His Cys
            100                 105                 110 atc att ggc cgc aca ctg gtg gtc cat gaa aaa gca gat gac ttg ggc        1045
Ile Ile Gly Arg Thr Leu Val Val His Glu Lys Ala Asp Asp Leu Gly
        115                 120                 125 aaa ggt gga aat gaa gaa agt aca aag aca gga aac gct gga agt cgt        1093
Lys Gly Gly Asn Glu Glu Ser Thr Lys Thr Gly Asn Ala Gly Ser Arg
    130                 135                 140 ttg gct tgt ggt gta att ggg atc gcc caa acc acc atg gtg agc aag        1141
Leu Ala Cys Gly Val Ile Gly Ile Ala Gln Thr Thr Met Val Ser Lys
145                 150                 155                 160 ggc gag gag ctg ttc acc ggg gtg gtg ccc atc ctg gtc gag ctg gac        1189
Gly Glu Glu Leu Phe Thr Gly Val Val Pro Ile Leu Val Glu Leu Asp
                165                 170                 175 ggc gac gta aac ggc cac aag ttc agc gtg tcc ggc gag ggc gag ggc        1237
Gly Asp Val Asn Gly His Lys Phe Ser Val Ser Gly Glu Gly Glu Gly
            180                 185                 190 gat gcc acc tac ggc aag ctg acc ctg aag ttc atc tgc acc acc ggc        1285
Asp Ala Thr Tyr Gly Lys Leu Thr Leu Lys Phe Ile Cys Thr Thr Gly
        195                 200                 205 aag ctg ccc gtg ccc tgg ccc acc ctc gtg acc acc ctg acc tac ggc        1333
Lys Leu Pro Val Pro Trp Pro Thr Leu Val Thr Thr Leu Thr Tyr Gly
    210                 215                 220 gtg cag tgc ttc agc cgc tac ccc gac cac atg aag cag cac gac ttc        1381
Val Gln Cys Phe Ser Arg Tyr Pro Asp His Met Lys Gln His Asp Phe
225                 230                 235                 240 ttc aag tcc gcc atg ccc gaa ggc tac gtc cag gag cgc acc atc ttc        1429
Phe Lys Ser Ala Met Pro Glu Gly Tyr Val Gln Glu Arg Thr Ile Phe
                245                 250                 255 ttc aag gac gac ggc aac tac aag acc cgc gcc gag gtg aag ttc gag        1477
Phe Lys Asp Asp Gly Asn Tyr Lys Thr Arg Ala Glu Val Lys Phe Glu
            260                 265                 270 ggc gac acc ctg gtg aac cgc atc gag ctg aag ggc atc gac ttc aag        1525
Gly Asp Thr Leu Val Asn Arg Ile Glu Leu Lys Gly Ile Asp Phe Lys
```

-continued

```
Gly Asp Thr Leu Val Asn Arg Ile Glu Leu Lys Gly Ile Asp Phe Lys
        275                 280                 285 gag gac ggc aac atc ctg ggg cac aag ctg gag tac aac tac aac agc      1573
Glu Asp Gly Asn Ile Leu Gly His Lys Leu Glu Tyr Asn Tyr Asn Ser
    290                 295                 300 cac aac gtc tat atc atg gcc gac aag cag aag aac ggc atc aag gtg      1621
His Asn Val Tyr Ile Met Ala Asp Lys Gln Lys Asn Gly Ile Lys Val
305                 310                 315                 320 aac ttc aag atc cgc cac aac atc gag gac ggc agc gtg cag ctc gcc      1669
Asn Phe Lys Ile Arg His Asn Ile Glu Asp Gly Ser Val Gln Leu Ala
                325                 330                 335 gac cac tac cag cag aac acc ccc atc ggc gac ggc ccc gtg ctg ctg      1717
Asp His Tyr Gln Gln Asn Thr Pro Ile Gly Asp Gly Pro Val Leu Leu
            340                 345                 350 ccc gac aac cac tac ctg agc acc cag tcc gcc ctg agc aaa gac ccc      1765
Pro Asp Asn His Tyr Leu Ser Thr Gln Ser Ala Leu Ser Lys Asp Pro
        355                 360                 365 aac gag aag cgc gat cac atg gtc ctg ctg gag ttc gtg acc gcc gcc      1813
Asn Glu Lys Arg Asp His Met Val Leu Leu Glu Phe Val Thr Ala Ala
    370                 375                 380 ggg atc act ctc ggc atg gac gag ctg tac aag taa agcggccgcg           1859
Gly Ile Thr Leu Gly Met Asp Glu Leu Tyr Lys
385                 390                 395 actctagatc ataatcagcc ataccacatt tgtagaggtt ttacttgctt taaaaaacct    1919
cccacacctc cccctgaacc tgaaacataa aatgaatgca attgttgttg ttaacttgtt    1979
tattgcagct tataatggtt acaaataaag caatagcatc acaaatttca caaataaagc    2039
atttttttca ctgcattcta gttgtggttt gtccaaactc atcaatgtat cttaaggcgt    2099
aaattgtaag cgttaatatt tgttaaaat tcgcgttaaa ttttttgttaa atcagctcat    2159 tttttaacca ataggccgaa atcggcaaaa tcccttataa atcaaaagaa tagaccgaga    2219
tagggttgag tgttgttcca gtttggaaca agagtccact attaaagaac gtggactcca    2279
acgtcaaagg gcgaaaaacc gtctatcagg gcgatggccc actacgtgaa ccatcaccct    2339
aatcaagttt tttggggtcg aggtgccgta agcactaaa tcggaaccct aaagggagcc    2399
cccgatttag agcttgacgg ggaaagccgg cgaacgtggc gagaaaggaa gggaagaaag    2459
cgaaaggagc gggcgctagg gcgctggcaa gtgtagcggt cacgctgcgc gtaaccacca    2519
cacccgccgc gcttaatgcg ccgctacagg gcgcgtcagg tggcactttt cggggaaatg    2579
tgcgcggaac ccctatttgt ttattttct aaatacattc aaatatgtat ccgctcatga    2639
gacaataacc ctgataaatg cttcaataat attgaaaaag gaagagtcct gaggcggaaa    2699
gaaccagctg tggaatgtgt gtcagttagg gtgtggaaag tccccaggct ccccagcagg    2759
cagaagtatg caaagcatgc atctcaatta gtcagcaacc aggtgtggaa agtccccagg    2819
ctccccagca ggcagaagta tgcaaagcat gcatctcaat tagtcagcaa ccatagtccc    2879
gcccctaact ccgcccatcc cgcccctaac tccgcccagt tccgcccatt ctccgcccca    2939
tggctgacta ttttttttta tttatgcaga ggccgaggcc gcctcggcct ctgagctatt    2999
ccagaagtag tgaggaggct ttttggagg cctaggcttt tgcaaagatc gatcaagaga    3059
caggatgagg atcgtttcgc atgattgaac aagatggatt gcacgcaggt tctccggccg    3119
cttgggtgga gaggctattc ggctatgact gggcacaaca gacaatcggc tgctctgatg    3179
ccgccgtgtt ccggctgtca gcgcaggggc gcccggttct ttttgtcaag accgacctgt    3239
ccggtgccct gaatgaactg caagacgagg cagcgcggct atcgtggctg gccacgacgg    3299
```

```
gcgttccttg cgcagctgtg ctcgacgttg tcactgaagc gggaagggac tggctgctat    3359
tgggcgaagt gccggggcag gatctcctgt catctcacct tgctcctgcc gagaaagtat    3419
ccatcatggc tgatgcaatg cggcggctgc atacgcttga tccggctacc tgcccattcg    3479
accaccaagc gaaacatcgc atcgagcgag cacgtactcg gatggaagcc ggtcttgtcg    3539
atcaggatga tctggacgaa gagcatcagg ggctcgcgcc agccgaactg ttcgccaggc    3599
tcaaggcgag catgcccgac ggcgaggatc tcgtcgtgac ccatggcgat gcctgcttgc    3659
cgaatatcat ggtggaaaat ggccgctttt ctggattcat cgactgtggc cggctgggtg    3719
tggcggaccg ctatcaggac atagcgttgg ctacccgtga tattgctgaa gagcttggcg    3779
gcgaatgggc tgaccgcttc ctcgtgcttt acggtatcgc cgctcccgat tcgcagcgca    3839
tcgccttcta tcgccttctt gacgagttct tctgagcggg actctgggt tcgaaatgac    3899 cgaccaagcg acgcccaacc tgccatcacg agatttcgat tccaccgccg ccttctatga    3959
aaggttgggc ttcggaatcg ttttccggga cgccggctgg atgatcctcc agcgcgggga    4019
tctcatgctg gagttcttcg cccacccctag ggggaggcta actgaaacac ggaaggagac    4079
aataccggaa ggaacccgcg ctatgacggc aataaaaaga cagaataaaa cgcacggtgt    4139
tgggtcgttt gttcataaac gcggggttcg gtcccagggc tggcactctg tcgataccc    4199 accgagaccc cattgggggcc aatacgcccg cgtttcttcc ttttccccac cccacccccc    4259
aagttcgggt gaaggcccag ggctcgcagc caacgtcggg gcggcaggcc ctgccatagc    4319
ctcaggttac tcatatatac tttagattga tttaaaactt cattttaat ttaaaaggat    4379 ctaggtgaag atccttttg ataatctcat gaccaaaatc ccttaacgtg agttttcgtt    4439
ccactgagcg tcagacccg tagaaaagat caaaggatct tcttgagatc cttttttttct    4499 gcgcgtaatc tgctgcttgc aaacaaaaaa accaccgcta ccagcggtgg tttgtttgcc    4559
ggatcaagag ctaccaactc ttttttccgaa ggtaactggc ttcagcagag cgcagatacc    4619
aaatactgtc cttctagtgt agccgtagtt aggccaccac ttcaagaact ctgtagcacc    4679
gcctacatac ctcgctctgc taatcctgtt accagtggct gctgccagtg gcgataagtc    4739
gtgtcttacc gggttggact caagacgata gttaccggat aaggcgcagc ggtcgggctg    4799 aacgggggt tcgtgcacac agcccagctt ggagcgaacg acctacaccg aactgagata    4859
cctacagcgt gagctatgag aaagcgccac gcttcccgaa gggagaaagg cggacaggta    4919
tccggtaagc ggcagggtcg gaacaggaga gcgcacgagg gagcttccag ggggaaacgc    4979
ctggtatctt tatagtcctg tcgggtttcg ccacctctga cttgagcgtc gatttttgtg    5039
atgctcgtca gggggggcgga gcctatgaa aaacgccagc aacgcggcct ttttacggtt    5099
cctggccttt tgctggcctt tgctcacat gttctttcct gcgttatccc ctgattctgt    5159
ggataaccgt attaccgcca tgcat                                          5184
```

<210> SEQ ID NO 2
<211> LENGTH: 154
<212> TYPE: PRT
<213> ORGANISM: Homo sapiens

<400> SEQUENCE: 2

Met Ala Thr Lys Ala Val Cys Val Leu Lys Gly Asp Gly Pro Val Gln
 1               5                  10                  15

Gly Ile Ile Asn Phe Glu Gln Lys Glu Ser Asn Gly Pro Val Lys Val
             20                  25                  30

Trp Gly Ser Ile Lys Gly Leu Thr Glu Gly Leu His Gly Phe His Val

-continued

```
                35                  40                  45
His Glu Phe Gly Asp Asn Thr Ala Gly Cys Thr Ser Ala Gly Pro His
 50                  55                  60

Phe Asn Pro Leu Ser Arg Lys His Gly Pro Lys Asp Glu Glu Arg
 65                  70                  75                  80

His Val Gly Asp Leu Gly Asn Val Thr Ala Asp Lys Asp Gly Val Ala
                 85                  90                  95

Asp Val Ser Ile Glu Asp Ser Val Ile Ser Leu Ser Gly Asp His Cys
                100                 105                 110

Ile Ile Gly Arg Thr Leu Val Val His Glu Lys Ala Asp Asp Leu Gly
            115                 120                 125

Lys Gly Gly Asn Glu Glu Ser Thr Lys Thr Gly Asn Ala Gly Ser Arg
130                 135                 140

Leu Ala Cys Gly Val Ile Gly Ile Ala Gln
145                 150

<210> SEQ ID NO 3
<211> LENGTH: 241
<212> TYPE: PRT
<213> ORGANISM: Homo sapiens

<400> SEQUENCE: 3

Thr Thr Met Val Ser Lys Gly Glu Glu Leu Phe Thr Gly Val Val Pro
  1               5                  10                  15

Ile Leu Val Glu Leu Asp Gly Asp Val Asn Gly His Lys Phe Ser Val
                 20                  25                  30

Ser Gly Glu Gly Glu Gly Asp Ala Thr Tyr Gly Lys Leu Thr Leu Lys
            35                  40                  45

Phe Ile Cys Thr Thr Gly Lys Leu Pro Val Pro Trp Pro Thr Leu Val
 50                  55                  60

Thr Thr Leu Thr Tyr Gly Val Gln Cys Phe Ser Arg Tyr Pro Asp His
 65                  70                  75                  80

Met Lys Gln His Asp Phe Phe Lys Ser Ala Met Pro Glu Gly Tyr Val
                 85                  90                  95

Gln Glu Arg Thr Ile Phe Phe Lys Asp Asp Gly Asn Tyr Lys Thr Arg
            100                 105                 110

Ala Glu Val Lys Phe Glu Gly Asp Thr Leu Val Asn Arg Ile Glu Leu
            115                 120                 125

Lys Gly Ile Asp Phe Lys Glu Asp Gly Asn Ile Leu Gly His Lys Leu
130                 135                 140

Glu Tyr Asn Tyr Asn Ser His Asn Val Tyr Ile Met Ala Asp Lys Gln
145                 150                 155                 160

Lys Asn Gly Ile Lys Val Asn Phe Lys Ile Arg His Asn Ile Glu Asp
                165                 170                 175

Gly Ser Val Gln Leu Ala Asp His Tyr Gln Gln Asn Thr Pro Ile Gly
            180                 185                 190

Asp Gly Pro Val Leu Leu Pro Asp Asn His Tyr Leu Ser Thr Gln Ser
            195                 200                 205

Ala Leu Ser Lys Asp Pro Asn Glu Lys Arg Asp His Met Val Leu Leu
        210                 215                 220

Glu Phe Val Thr Ala Ala Gly Ile Thr Leu Gly Met Asp Glu Leu Tyr
225                 230                 235                 240

Lys
```

<210> SEQ ID NO 4
<211> LENGTH: 6268
<212> TYPE: DNA
<213> ORGANISM: Homo sapiens
<220> FEATURE:
<221> NAME/KEY: CDS
<222> LOCATION: (613)..(1329)
<223> OTHER INFORMATION: enhanced green fluorescent protein
<221> NAME/KEY: CDS
<222> LOCATION: (1330)..(2859)
<223> OTHER INFORMATION: calcineurin A alpha

<400> SEQUENCE: 4

```
tagttattaa tagtaatcaa ttacggggtc attagttcat agcccatata tggagttccg        60
cgttacataa cttacggtaa atggcccgcc tggctgaccg cccaacgacc cccgcccatt       120
gacgtcaata atgacgtatg ttcccatagt aacgccaata gggactttcc attgacgtca       180
atgggtggag tatttacggt aaactgccca cttggcagta catcaagtgt atcatatgcc       240
aagtacgccc cctattgacg tcaatgacgg taaatggccc gcctggcatt atgcccagta       300
catgacctta tgggactttc ctacttggca gtacatctac gtattagtca tcgctattac       360
catggtgatg cggttttggc agtacatcaa tgggcgtgga tagcggtttg actcacgggg       420
atttccaagt ctccacccca ttgacgtcaa tgggagtttg ttttggcacc aaaatcaacg       480
ggactttcca aaatgtcgta caactccgcc ccattgacg caaatgggcg gtaggcgtgt       540
acggtgggag gtctatataa gcagagctgg tttagtgaac cgtcagatcc gctagcgcta       600
ccggtcgcca cc atg gtg agc aag ggc gag gag ctg ttc acc ggg gtg gtg       651
         Met Val Ser Lys Gly Glu Glu Leu Phe Thr Gly Val Val
         1               5                  10 ccc atc ctg gtc gag ctg gac ggc gac gta aac ggc cac aag ttc agc        699
Pro Ile Leu Val Glu Leu Asp Gly Asp Val Asn Gly His Lys Phe Ser
 15                  20                  25 gtg tcc ggc gag ggc gag ggc gat gcc acc tac ggc aag ctg acc ctg        747
Val Ser Gly Glu Gly Glu Gly Asp Ala Thr Tyr Gly Lys Leu Thr Leu
 30                  35                  40                  45 aag ttc atc tgc acc acc ggc aag ctg ccc gtg ccc tgg ccc acc ctc        795
Lys Phe Ile Cys Thr Thr Gly Lys Leu Pro Val Pro Trp Pro Thr Leu
                 50                  55                  60 gtg acc acc ctg acc tac ggc gtg cag tgc ttc agc cgc tac ccc gac        843
Val Thr Thr Leu Thr Tyr Gly Val Gln Cys Phe Ser Arg Tyr Pro Asp
             65                  70                  75 cac atg aag cag cac gac ttc ttc aag tcc gcc atg ccc gaa ggc tac        891
His Met Lys Gln His Asp Phe Phe Lys Ser Ala Met Pro Glu Gly Tyr
         80                  85                  90 gtc cag gag cgc acc atc ttc ttc aag gac gac ggc aac tac aag acc        939
Val Gln Glu Arg Thr Ile Phe Phe Lys Asp Asp Gly Asn Tyr Lys Thr
     95                 100                 105 cgc gcc gag gtg aag ttc gag ggc gac acc ctg gtg aac cgc atc gag        987
Arg Ala Glu Val Lys Phe Glu Gly Asp Thr Leu Val Asn Arg Ile Glu
110                 115                 120                 125 ctg aag ggc atc gac ttc aag gag gac ggc aac atc ctg ggg cac aag       1035
Leu Lys Gly Ile Asp Phe Lys Glu Asp Gly Asn Ile Leu Gly His Lys
                130                 135                 140 ctg gag tac aac tac aac agc cac aac gtc tat atc atg gcc gac aag       1083
Leu Glu Tyr Asn Tyr Asn Ser His Asn Val Tyr Ile Met Ala Asp Lys
            145                 150                 155 cag aag aac ggc atc aag gtg aac ttc aag atc cgc cac aac atc gag       1131
Gln Lys Asn Gly Ile Lys Val Asn Phe Lys Ile Arg His Asn Ile Glu
        160                 165                 170 gac ggc agc gtg cag ctc gcc gac cac tac cag cag aac acc ccc atc       1179
```

```
                Asp Gly Ser Val Gln Leu Ala Asp His Tyr Gln Gln Asn Thr Pro Ile
                    175                 180                 185 ggc gac ggc ccc gtg ctg ctg ccc gac aac cac tac ctg agc acc cag       1227
Gly Asp Gly Pro Val Leu Leu Pro Asp Asn His Tyr Leu Ser Thr Gln
190                 195                 200                 205 tcc gcc ctg agc aaa gac ccc aac gag aag cgc gat cac atg gtc ctg       1275
Ser Ala Leu Ser Lys Asp Pro Asn Glu Lys Arg Asp His Met Val Leu
                210                 215                 220 ctg gag ttc gtg acc gcc gcc ggg atc act ctc ggc atg gac gag ctg       1323
Leu Glu Phe Val Thr Ala Ala Gly Ile Thr Leu Gly Met Asp Glu Leu
            225                 230                 235 tac aag tcc gga ctc aga tcc atg tcc gag ccc aag gca att gat ccc       1371
Tyr Lys Ser Gly Leu Arg Ser Met Ser Glu Pro Lys Ala Ile Asp Pro
        240                 245                 250 aag ttg tcg acg acc gac agg gtg gtg aaa gct gtt cca ttt cct cca       1419
Lys Leu Ser Thr Thr Asp Arg Val Val Lys Ala Val Pro Phe Pro Pro
    255                 260                 265 agt cac cgg ctt aca gca aaa gaa gtg ttt gat aat gat gga aaa cct       1467
Ser His Arg Leu Thr Ala Lys Glu Val Phe Asp Asn Asp Gly Lys Pro
270                 275                 280                 285 cgt gtg gat atc tta aag gcg cat ctt atg aag gag gga agg ctg gaa       1515
Arg Val Asp Ile Leu Lys Ala His Leu Met Lys Glu Gly Arg Leu Glu
                290                 295                 300 gag agt gtt gca ttg aga ata ata aca gag ggt gca tca att ctt cga       1563
Glu Ser Val Ala Leu Arg Ile Ile Thr Glu Gly Ala Ser Ile Leu Arg
            305                 310                 315 cag gaa aaa aat ttg ctg gat att gat gcg cca gtc act gtt tgt ggg       1611
Gln Glu Lys Asn Leu Leu Asp Ile Asp Ala Pro Val Thr Val Cys Gly
        320                 325                 330 gac att cat gga caa ttc ttt gat ttg atg aag ctc ttt gaa gtc ggg       1659
Asp Ile His Gly Gln Phe Phe Asp Leu Met Lys Leu Phe Glu Val Gly
    335                 340                 345 gga tct cct gcc aac act cgc tac ctc ttc tta ggg gac tat gtt gac       1707
Gly Ser Pro Ala Asn Thr Arg Tyr Leu Phe Leu Gly Asp Tyr Val Asp
350                 355                 360                 365 aga ggg tac ttc agt att gaa tgt gtg ctg tat ttg tgg gcc ttg aaa       1755
Arg Gly Tyr Phe Ser Ile Glu Cys Val Leu Tyr Leu Trp Ala Leu Lys
                370                 375                 380 att ctc tac ccc aaa aca ctg ttt tta ctt cgt gga aat cat gaa tgt       1803
Ile Leu Tyr Pro Lys Thr Leu Phe Leu Leu Arg Gly Asn His Glu Cys
            385                 390                 395 aga cat cta aca gag tat ttc aca ttt aaa caa gaa tgt aaa ata aag       1851
Arg His Leu Thr Glu Tyr Phe Thr Phe Lys Gln Glu Cys Lys Ile Lys
        400                 405                 410 tat tca gaa cga gta tat gat gcc tgt atg gat gcc ttt gac tgc ctt       1899
Tyr Ser Glu Arg Val Tyr Asp Ala Cys Met Asp Ala Phe Asp Cys Leu
    415                 420                 425 ccc ctg gct gcc ctg atg aac caa cag ttc ctg tgt gtg cat ggt ggt       1947
Pro Leu Ala Ala Leu Met Asn Gln Gln Phe Leu Cys Val His Gly Gly
430                 435                 440                 445 ttg tct cca gag att aac act tta gat gat atc aga aaa tta gac cga       1995
Leu Ser Pro Glu Ile Asn Thr Leu Asp Asp Ile Arg Lys Leu Asp Arg
                450                 455                 460 ttc aaa gaa cca cct gca tat gga cct atg tgt gat atc ctg tgg tca       2043
Phe Lys Glu Pro Pro Ala Tyr Gly Pro Met Cys Asp Ile Leu Trp Ser
            465                 470                 475 gac ccc ctg gaa gat ttt gga aat gag aag act cag gaa cat ttc act       2091
Asp Pro Leu Glu Asp Phe Gly Asn Glu Lys Thr Gln Glu His Phe Thr
        480                 485                 490
```

-continued

| | |
|---|---|
| cac aac aca gtc agg ggg tgt tca tac ttc tac agt tac ccg gct gta<br>His Asn Thr Val Arg Gly Cys Ser Tyr Phe Tyr Ser Tyr Pro Ala Val<br>495                      500                  505 | 2139 |
| tgt gaa ttc tta cag cac aat aac ttg tta tct ata ctc cga gcc cac<br>Cys Glu Phe Leu Gln His Asn Asn Leu Leu Ser Ile Leu Arg Ala His<br>510                      515                  520                  525 | 2187 |
| gaa gcc caa gat gca ggg tac cgc atg tac agg aaa agc caa aca aca<br>Glu Ala Gln Asp Ala Gly Tyr Arg Met Tyr Arg Lys Ser Gln Thr Thr<br>                  530                  535                  540 | 2235 |
| ggc ttc cct tct cta att aca att ttt tca gca cca aat tac tta gat<br>Gly Phe Pro Ser Leu Ile Thr Ile Phe Ser Ala Pro Asn Tyr Leu Asp<br>              545                  550                  555 | 2283 |
| gta tac aat aac aaa gct gca gta ttg aag tat gag aac aat gtt atg<br>Val Tyr Asn Asn Lys Ala Ala Val Leu Lys Tyr Glu Asn Asn Val Met<br>560                      565                  570 | 2331 |
| aat atc agg caa ttc aac tgt tct cct cat cca tac tgg ctt cca aat<br>Asn Ile Arg Gln Phe Asn Cys Ser Pro His Pro Tyr Trp Leu Pro Asn<br>575                      580                  585 | 2379 |
| ttc atg gat gtt ttt act tgg tcc ctt cca ttt gtt ggg gaa aaa gtg<br>Phe Met Asp Val Phe Thr Trp Ser Leu Pro Phe Val Gly Glu Lys Val<br>590                      595                  600                  605 | 2427 |
| act gag atg ctg gta aat gtc ctc aac atc tgc tca gat gat gaa cta<br>Thr Glu Met Leu Val Asn Val Leu Asn Ile Cys Ser Asp Asp Glu Leu<br>                    610                  615                  620 | 2475 |
| ggg tca gaa gaa gat gga ttt gat ggt gca aca gct gca gcc cgg aaa<br>Gly Ser Glu Glu Asp Gly Phe Asp Gly Ala Thr Ala Ala Ala Arg Lys<br>              625                  630                  635 | 2523 |
| gag gtg ata agg aac aag atc cga gca ata ggc aaa atg gcc aga gtg<br>Glu Val Ile Arg Asn Lys Ile Arg Ala Ile Gly Lys Met Ala Arg Val<br>                    640                  645                  650 | 2571 |
| ttc tca gtg ctc aga gaa gag agt gag agt gtg ctg acg ctg aaa ggc<br>Phe Ser Val Leu Arg Glu Glu Ser Glu Ser Val Leu Thr Leu Lys Gly<br>655                      660                  665 | 2619 |
| ttg acc cca act ggc atg ctc ccc agc gga gta ctt tct gga ggg aag<br>Leu Thr Pro Thr Gly Met Leu Pro Ser Gly Val Leu Ser Gly Gly Lys<br>670                      675                  680                  685 | 2667 |
| caa acc ctg caa agc gct act gtt gag gct att gag gct gat gaa gct<br>Gln Thr Leu Gln Ser Ala Thr Val Glu Ala Ile Glu Ala Asp Glu Ala<br>                    690                  695                  700 | 2715 |
| atc aaa gga ttt tca cca caa cat aag atc act agc ttc gag gaa gcc<br>Ile Lys Gly Phe Ser Pro Gln His Lys Ile Thr Ser Phe Glu Glu Ala<br>              705                  710                  715 | 2763 |
| aag ggc tta gac cga att aat gag agg atg ccg cct cgc aga gat gcc<br>Lys Gly Leu Asp Arg Ile Asn Glu Arg Met Pro Pro Arg Arg Asp Ala<br>720                      725                  730 | 2811 |
| atg ccc tct gac gcc aac ctt aac tcc atc aac aag gct ctc acc tca<br>Met Pro Ser Asp Ala Asn Leu Asn Ser Ile Asn Lys Ala Leu Thr Ser<br>735                      740                  745 | 2859 |
| gagactaacg gcacggacag caatggcagt aatagcagca atattcagtg attaactagg | 2919 |
| gtaccccgga tccaccggat ctagataact gatcataatc agccatacca catttgtaga | 2979 |
| ggttttactt gctttaaaaa acctcccaca cctcccctg aacctgaaac ataaaatgaa | 3039 |
| tgcaattgtt gttgttaact tgtttattgc agcttataat ggttacaaat aaagcaatag | 3099 |
| catcacaaat ttcacaaata aagcattttt ttcactgcat tctagttgtg gtttgtccaa | 3159 |
| actcatcaat gtatcttaac gcgtaaattg taagcgttaa tattttgtta aaattcgcgt | 3219 |
| taaattttg ttaaatcagc tcattttta accaataggc cgaaatcggc aaaatccctt | 3279 |

```
ataaatcaaa agaatagacc gagatagggt tgagtgttgt tccagtttgg aacaagagtc    3339
cactattaaa gaacgtggac tccaacgtca aagggcgaaa aaccgtctat cagggcgatg    3399
gcccactacg tgaaccatca ccctaatcaa gttttttggg gtcgaggtgc cgtaaagcac    3459
taaatcggaa ccctaaaggg agcccccgat ttagagcttg acggggaaag ccggcgaacg    3519
tggcgagaaa ggaagggaag aaagcgaaag gagcgggcgc tagggcgctg gcaagtgtag    3579
cggtcacgct gcgcgtaacc accacacccg ccgcgcttaa tgcgccgcta cagggcgcgt    3639
caggtggcac ttttcgggga aatgtgcgcg gaacccctat ttgtttattt ttctaaatac    3699
attcaaatat gtatccgctc atgagacaat aaccctgata aatgcttcaa taatattgaa    3759
aaaggaagag tcctgaggcg gaaagaacca gctgtggaat gtgtgtcagt tagggtgtgg    3819
aaagtcccca ggctcccag caggcagaag tatgcaaagc atgcatctca attagtcagc    3879
aaccaggtgt ggaaagtccc caggctcccc agcaggcaga agtatgcaaa gcatgcatct    3939
caattagtca gcaaccatag tcccgcccct aactccgccc atcccgcccc taactccgcc    3999
cagttccgcc cattctccgc cccatggctg actaatttt tttatttatg cagaggccga    4059
ggccgcctcg gcctctgagc tattccagaa gtagtgagga ggcttttttg gaggcctagg    4119
cttttgcaaa gatcgatcaa gagacaggat gaggatcgtt tcgcatgatt gaacaagatg    4179
gattgcacgc aggttctccg gccgcttggg tggagaggc attcggctat gactgggcac    4239
aacagacaat cggctgctct gatgccgccg tgttccggct gtcagcgcag gggcgcccgg    4299 ttcttttgt caagaccgac ctgtccgtg ccctgaatga actgcaagac gaggcagcgc    4359
ggctatcgtg gctggccacg acgggcgttc cttgcgcagc tgtgctcgac gttgtcactg    4419
aagcgggaag ggactggctg ctattgggcg aagtgccggg gcaggatctc ctgtcatctc    4479
accttgctcc tgccgagaaa gtatccatca tggctgatgc aatgcggcgg ctgcatacgc    4539
ttgatccggc tacctgccca ttcgaccacc aagcgaaaca tcgcatcgag cgagcacgta    4599
ctcggatgga agccggtctt gtcgatcagg atgatctgga cgaagagcat caggggctcg    4659
cgccagccga actgttcgcc aggctcaagg cgagcatgcc cgacggcgag gatctcgtcg    4719
tgacccatgg cgatgcctgc ttgccgaata tcatggtgga aaatggccgc ttttctggat    4779
tcatcgactg tggccggctg ggtgtggcgg accgctatca ggacatagcg ttggctaccc    4839
gtgatattgc tgaagagctt ggcggcgaat gggctgaccg cttcctcgtg ctttacggta    4899
tcgccgctcc cgattcgcag cgcatcgcct tctatcgcct tcttgacgag ttcttctgag    4959
cgggactctg gggttcgaaa tgaccgacca agcgacgccc aacctgccat cacgagattt    5019
cgattccacc gccgccttct atgaaaggtt gggcttcgga atcgttttcc gggacgccgg    5079
ctggatgatc ctccagcgcg gggatctcat gctggagttc ttcgcccacc ctaggggag    5139 gctaactgaa acacggaagg agacaatacc ggaaggaacc cgcgctatga cggcaataaa    5199
aagacagaat aaaacgcacg tgttgggtc gtttgttcat aaacgcgggg ttcggtccca    5259
gggctggcac tctgtcgata ccccaccgag accccattgg ggccaatacg cccgcgtttc    5319
ttccttttcc ccaccccacc cccaagttc gggtgaaggc ccagggctcg cagccaacgt    5379
cggggcggca ggccctgcca tagcctcagg ttactcatat atactttaga ttgatttaaa    5439
acttcatttt taatttaaaa ggatctaggt gaagatcctt tttgataatc tcatgaccaa    5499
aatcccttaa cgtgagtttt cgttccactg agcgtcagac cccgtagaaa agatcaaagg    5559
atcttcttga gatccttttt ttctgcgcgt aatctgctgc ttgcaaacaa aaaaaccacc    5619
```

-continued

```
gctaccagcg gtggtttgtt tgccggatca agagctacca actctttttc cgaaggtaac    5679
tggcttcagc agagcgcaga taccaaatac tgtccttcta gtgtagccgt agttaggcca    5739
ccacttcaag aactctgtag caccgcctac atacctcgct ctgctaatcc tgttaccagt    5799
ggctgctgcc agtggcgata agtcgtgtct taccggggttg gactcaagac gatagttacc   5859
ggataaggcg cagcggtcgg gctgaacggg gggttcgtgc acacagccca gcttggagcg    5919
aacgacctac accgaactga gatacctaca gcgtgagcta tgagaaagcg ccacgcttcc    5979
cgaagggaga aagcggaca ggtatccggt aagcggcagg gtcggaacag gagagcgcac     6039
gagggagctt ccaggggaa acgcctggta tctttatagt cctgtcgggt ttcgccacct     6099
ctgacttgag cgtcgatttt tgtgatgctc gtcaggggg cggagcctat ggaaaacgc      6159 cagcaacgcg gccttttac ggttcctggc cttttgctgg ccttttgctc acatgttctt    6219
tcctgcgtta tccctgatt ctgtggataa ccgtattacc gccatgcat                6268
```

<210> SEQ ID NO 5
<211> LENGTH: 239
<212> TYPE: PRT
<213> ORGANISM: Homo sapiens

<400> SEQUENCE: 5

```
Met Val Ser Lys Gly Glu Glu Leu Phe Thr Gly Val Val Pro Ile Leu
  1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
     50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 6
<211> LENGTH: 510
<212> TYPE: PRT

<213> ORGANISM: Homo sapiens

<400> SEQUENCE: 6

```
Ser Gly Leu Arg Ser Met Ser Glu Pro Lys Ala Ile Asp Pro Lys Leu
  1               5                  10                  15
Ser Thr Thr Asp Arg Val Val Lys Ala Val Pro Phe Pro Pro Ser His
                 20                  25                  30
Arg Leu Thr Ala Lys Glu Val Phe Asp Asn Asp Gly Lys Pro Arg Val
             35                  40                  45
Asp Ile Leu Lys Ala His Leu Met Lys Glu Gly Arg Leu Glu Glu Ser
         50                  55                  60
Val Ala Leu Arg Ile Ile Thr Glu Gly Ala Ser Ile Leu Arg Gln Glu
 65                  70                  75                  80
Lys Asn Leu Leu Asp Ile Asp Ala Pro Val Thr Val Cys Gly Asp Ile
                 85                  90                  95
His Gly Gln Phe Phe Asp Leu Met Lys Leu Phe Glu Val Gly Gly Ser
            100                 105                 110
Pro Ala Asn Thr Arg Tyr Leu Phe Leu Gly Asp Tyr Val Asp Arg Gly
        115                 120                 125
Tyr Phe Ser Ile Glu Cys Val Leu Tyr Leu Trp Ala Leu Lys Ile Leu
130                 135                 140
Tyr Pro Lys Thr Leu Phe Leu Leu Arg Gly Asn His Glu Cys Arg His
145                 150                 155                 160
Leu Thr Glu Tyr Phe Thr Phe Lys Gln Glu Cys Lys Ile Lys Tyr Ser
                165                 170                 175
Glu Arg Val Tyr Asp Ala Cys Met Asp Ala Phe Asp Cys Leu Pro Leu
            180                 185                 190
Ala Ala Leu Met Asn Gln Gln Phe Leu Cys Val His Gly Gly Leu Ser
        195                 200                 205
Pro Glu Ile Asn Thr Leu Asp Asp Ile Arg Lys Leu Asp Arg Phe Lys
    210                 215                 220
Glu Pro Pro Ala Tyr Gly Pro Met Cys Asp Ile Leu Trp Ser Asp Pro
225                 230                 235                 240
Leu Glu Asp Phe Gly Asn Glu Lys Thr Gln Glu His Phe Thr His Asn
                245                 250                 255
Thr Val Arg Gly Cys Ser Tyr Phe Tyr Ser Tyr Pro Ala Val Cys Glu
            260                 265                 270
Phe Leu Gln His Asn Asn Leu Leu Ser Ile Leu Arg Ala His Glu Ala
        275                 280                 285
Gln Asp Ala Gly Tyr Arg Met Tyr Arg Lys Ser Gln Thr Thr Gly Phe
    290                 295                 300
Pro Ser Leu Ile Thr Ile Phe Ser Ala Pro Asn Tyr Leu Asp Val Tyr
305                 310                 315                 320
Asn Asn Lys Ala Ala Val Leu Lys Tyr Glu Asn Asn Val Met Asn Ile
                325                 330                 335
Arg Gln Phe Asn Cys Ser Pro His Pro Tyr Trp Leu Pro Asn Phe Met
            340                 345                 350
Asp Val Phe Thr Trp Ser Leu Pro Phe Val Gly Glu Lys Val Thr Glu
        355                 360                 365
Met Leu Val Asn Val Leu Asn Ile Cys Ser Asp Asp Glu Leu Gly Ser
    370                 375                 380
Glu Glu Asp Gly Phe Asp Gly Ala Thr Ala Ala Ala Arg Lys Glu Val
385                 390                 395                 400
```

-continued

```
Ile Arg Asn Lys Ile Arg Ala Ile Gly Lys Met Ala Arg Val Phe Ser
            405                 410                 415
Val Leu Arg Glu Glu Ser Glu Ser Val Leu Thr Leu Lys Gly Leu Thr
        420                 425                 430
Pro Thr Gly Met Leu Pro Ser Gly Val Leu Ser Gly Lys Gln Thr
            435                 440                 445
Leu Gln Ser Ala Thr Val Glu Ala Ile Glu Ala Asp Glu Ala Ile Lys
    450                 455                 460
Gly Phe Ser Pro Gln His Lys Ile Thr Ser Phe Glu Glu Ala Lys Gly
465                 470                 475                 480
Leu Asp Arg Ile Asn Glu Arg Met Pro Pro Arg Asp Ala Met Pro
                485                 490                 495
Ser Asp Ala Asn Leu Asn Ser Ile Asn Lys Ala Leu Thr Ser
            500                 505                 510

<210> SEQ ID NO 7
<211> LENGTH: 6275
<212> TYPE: DNA
<213> ORGANISM: Homo sapiens
<220> FEATURE:
<221> NAME/KEY: CDS
<222> LOCATION: (613)..(1329)
<223> OTHER INFORMATION: enhanced green fluorescent protein
<221> NAME/KEY: CDS
<222> LOCATION: (1330)..(2916)
<223> OTHER INFORMATION: calcineurin A beta

<400> SEQUENCE: 7
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cgtcagatcc gctagcgcta    600
ccggtcgcca cc atg gtg agc aag ggc gag gag ctg ttc acc ggg gtg gtg    651
          Met Val Ser Lys Gly Glu Glu Leu Phe Thr Gly Val Val
            1               5                  10 ccc atc ctg gtc gag ctg gac ggc gac gta aac ggc cac aag ttc agc    699
Pro Ile Leu Val Glu Leu Asp Gly Asp Val Asn Gly His Lys Phe Ser
    15                  20                  25 gtg tcc ggc gag ggc gag ggc gat gcc acc tac ggc aag ctg acc ctg    747
Val Ser Gly Glu Gly Glu Gly Asp Ala Thr Tyr Gly Lys Leu Thr Leu
 30                  35                  40                  45 aag ttc atc tgc acc acc ggc aag ctg ccc gtg ccc tgg ccc acc ctc    795
Lys Phe Ile Cys Thr Thr Gly Lys Leu Pro Val Pro Trp Pro Thr Leu
                50                  55                  60 gtg acc acc ctg acc tac ggc gtg cag tgc ttc agc cgc tac ccc gac    843
Val Thr Thr Leu Thr Tyr Gly Val Gln Cys Phe Ser Arg Tyr Pro Asp
            65                  70                  75 cac atg aag cag cac gac ttc ttc aag tcc gcc atg ccc gaa ggc tac    891
His Met Lys Gln His Asp Phe Phe Lys Ser Ala Met Pro Glu Gly Tyr
        80                  85                  90
```

-continued

| | |
|---|---|
| gtc cag gag cgc acc atc ttc ttc aag gac gac ggc aac tac aag acc<br>Val Gln Glu Arg Thr Ile Phe Phe Lys Asp Asp Gly Asn Tyr Lys Thr<br>    95                       100                   105 | 939 |
| cgc gcc gag gtg aag ttc gag ggc gac acc ctg gtg aac cgc atc gag<br>Arg Ala Glu Val Lys Phe Glu Gly Asp Thr Leu Val Asn Arg Ile Glu<br>110               115                   120                 125 | 987 |
| ctg aag ggc atc gac ttc aag gag gac ggc aac atc ctg ggg cac aag<br>Leu Lys Gly Ile Asp Phe Lys Glu Asp Gly Asn Ile Leu Gly His Lys<br>                   130                   135                 140 | 1035 |
| ctg gag tac aac tac aac agc cac aac gtc tat atc atg gcc gac aag<br>Leu Glu Tyr Asn Tyr Asn Ser His Asn Val Tyr Ile Met Ala Asp Lys<br>        145                   150                   155 | 1083 |
| cag aag aac ggc atc aag gtg aac ttc aag atc cgc cac aac atc gag<br>Gln Lys Asn Gly Ile Lys Val Asn Phe Lys Ile Arg His Asn Ile Glu<br>160               165                   170 | 1131 |
| gac ggc agc gtg cag ctc gcc gac cac tac cag cag aac acc ccc atc<br>Asp Gly Ser Val Gln Leu Ala Asp His Tyr Gln Gln Asn Thr Pro Ile<br>                   175                   180                 185 | 1179 |
| ggc gac ggc ccc gtg ctg ctg ccc gac aac cac tac ctg agc acc cag<br>Gly Asp Gly Pro Val Leu Leu Pro Asp Asn His Tyr Leu Ser Thr Gln<br>190               195                   200                 205 | 1227 |
| tcc gcc ctg agc aaa gac ccc aac gag aag cgc gat cac atg gtc ctg<br>Ser Ala Leu Ser Lys Asp Pro Asn Glu Lys Arg Asp His Met Val Leu<br>                   210                   215                 220 | 1275 |
| ctg gag ttc gtg acc gcc gcc ggg atc act ctc ggc atg gac gag ctg<br>Leu Glu Phe Val Thr Ala Ala Gly Ile Thr Leu Gly Met Asp Glu Leu<br>        225                   230                   235 | 1323 |
| tac aag tcc gga ctc aga tcc gcc gcc ccg gag ccg gcc cgg gct gca<br>Tyr Lys Ser Gly Leu Arg Ser Ala Ala Pro Glu Pro Ala Arg Ala Ala<br>240               245                   250 | 1371 |
| ccg ccc cca ccc ccg ccc ccg ccg ccc cct ccc ggg gct gac cgc gtc<br>Pro Pro Pro Pro Pro Pro Pro Pro Pro Pro Pro Gly Ala Asp Arg Val<br>        255                   260                   265 | 1419 |
| gtc aaa gct gtc cct ttc ccc cca aca cat cgc ttg aca tct gaa gaa<br>Val Lys Ala Val Pro Phe Pro Pro Thr His Arg Leu Thr Ser Glu Glu<br>270               275                   280                 285 | 1467 |
| gta ttt gat ttg gat ggg ata ccc agg gtt gat gtt ctg aag aac cac<br>Val Phe Asp Leu Asp Gly Ile Pro Arg Val Asp Val Leu Lys Asn His<br>                   290                   295                 300 | 1515 |
| ttg gtg aaa gaa ggt cga gta gat gaa gaa att gcg ctt aga att atc<br>Leu Val Lys Glu Gly Arg Val Asp Glu Glu Ile Ala Leu Arg Ile Ile<br>        305                   310                   315 | 1563 |
| aat gag ggt gct gcc atc ctt cgg aga gag aaa acc atg ata gaa gta<br>Asn Glu Gly Ala Ala Ile Leu Arg Arg Glu Lys Thr Met Ile Glu Val<br>                   320                   325                 330 | 1611 |
| gaa gct cca atc aca gtg tgt ggt gac atc cat ggc caa ttt ttt gat<br>Glu Ala Pro Ile Thr Val Cys Gly Asp Ile His Gly Gln Phe Phe Asp<br>335               340                   345 | 1659 |
| ctg atg aaa ctt ttt gaa gta gga gga tca cct gct aat aca cga tac<br>Leu Met Lys Leu Phe Glu Val Gly Gly Ser Pro Ala Asn Thr Arg Tyr<br>350               355                   360                 365 | 1707 |
| ctt ttt ctt ggc gat tat gtg gac aga ggt tat ttt agt ata gag tgt<br>Leu Phe Leu Gly Asp Tyr Val Asp Arg Gly Tyr Phe Ser Ile Glu Cys<br>                   370                   375                 380 | 1755 |
| gtc tta tat tta tgg gtt ctg aag att cta tac cca agc aca tta ttt<br>Val Leu Tyr Leu Trp Val Leu Lys Ile Leu Tyr Pro Ser Thr Leu Phe<br>        385                   390                   395 | 1803 |
| ctt ctg aga ggc aac cat gaa tgc aga cac ctt act gaa tat ttt acc<br>Leu Leu Arg Gly Asn His Glu Cys Arg His Leu Thr Glu Tyr Phe Thr | 1851 |

```
                400                 405                 410
ttt aag cag gaa tgt aaa att aag tat tcg gaa aga gtc tat gaa gct   1899
Phe Lys Gln Glu Cys Lys Ile Lys Tyr Ser Glu Arg Val Tyr Glu Ala
        415                 420                 425 tgt atg gaa gct ttt gat agt ttg cct ctt gct gca ctt tta aac caa   1947
Cys Met Glu Ala Phe Asp Ser Leu Pro Leu Ala Ala Leu Leu Asn Gln
430                 435                 440                 445 cag ttt ctt tgt gtt cat ggt gga ctt tca cca gaa ata cac aca ctg   1995
Gln Phe Leu Cys Val His Gly Gly Leu Ser Pro Glu Ile His Thr Leu
                450                 455                 460 gat gat att agg aga tta gat aga ttc aaa gag cca cct gca ttt gga   2043
Asp Asp Ile Arg Arg Leu Asp Arg Phe Lys Glu Pro Pro Ala Phe Gly
            465                 470                 475 cca atg tgt gac ttg tta tgg tcc gat cct tct gaa gat ttt gga aat   2091
Pro Met Cys Asp Leu Leu Trp Ser Asp Pro Ser Glu Asp Phe Gly Asn
        480                 485                 490 gaa aaa tca cag gaa cat ttt agt cac aat aca gtt cga gga tgt tct   2139
Glu Lys Ser Gln Glu His Phe Ser His Asn Thr Val Arg Gly Cys Ser
    495                 500                 505 tat ttt tat aac tat cca gca gtg tgt gaa ttt ttg caa aac aat aat   2187
Tyr Phe Tyr Asn Tyr Pro Ala Val Cys Glu Phe Leu Gln Asn Asn Asn
510                 515                 520                 525 ttg tta tcg att att aga gct cat gaa gct caa gat gca ggc tat aga   2235
Leu Leu Ser Ile Ile Arg Ala His Glu Ala Gln Asp Ala Gly Tyr Arg
                530                 535                 540 atg tac aga aaa agt caa act aca ggg ttc cct tca tta ata aca att   2283
Met Tyr Arg Lys Ser Gln Thr Thr Gly Phe Pro Ser Leu Ile Thr Ile
            545                 550                 555 ttt tcg gca cct aat tac tta gat gtc tac aat aat aaa gct gct gta   2331
Phe Ser Ala Pro Asn Tyr Leu Asp Val Tyr Asn Asn Lys Ala Ala Val
        560                 565                 570 tta aag tat gaa aat aat gtg atg aat att cga cag ttt aac tgt tct   2379
Leu Lys Tyr Glu Asn Asn Val Met Asn Ile Arg Gln Phe Asn Cys Ser
    575                 580                 585 cca cat cct tac tgg ttg cct aat ttt atg gat gtc ttc acg tgg tct   2427
Pro His Pro Tyr Trp Leu Pro Asn Phe Met Asp Val Phe Thr Trp Ser
590                 595                 600                 605 tta ccg ttt gtt gga gaa aaa gtg aca gaa atg ttg gta aat gtt ctg   2475
Leu Pro Phe Val Gly Glu Lys Val Thr Glu Met Leu Val Asn Val Leu
                610                 615                 620 agt att tgc tct gat gat gaa cta atg act gaa ggt gaa gac cag ttt   2523
Ser Ile Cys Ser Asp Asp Glu Leu Met Thr Glu Gly Glu Asp Gln Phe
            625                 630                 635 gat ggt tca gct gca gcc cgg aaa gaa atc ata aga aac aaa att cga   2571
Asp Gly Ser Ala Ala Ala Arg Lys Glu Ile Ile Arg Asn Lys Ile Arg
        640                 645                 650 gca att ggc aag atg gca aga gtc ttc tct gtt ctc agg gag gag agt   2619
Ala Ile Gly Lys Met Ala Arg Val Phe Ser Val Leu Arg Glu Glu Ser
    655                 660                 665 gaa agt gtg ctg aca ctc aag ggc ctg act ccc aca ggg atg ttg cct   2667
Glu Ser Val Leu Thr Leu Lys Gly Leu Thr Pro Thr Gly Met Leu Pro
670                 675                 680                 685 agt gga gtg tta gct gga gga cgg cag acc ctg caa agt gcc aca gtt   2715
Ser Gly Val Leu Ala Gly Gly Arg Gln Thr Leu Gln Ser Ala Thr Val
                690                 695                 700 gag gct att gag gct gaa aaa gca ata cga gga ttc tct cca cca cat   2763
Glu Ala Ile Glu Ala Glu Lys Ala Ile Arg Gly Phe Ser Pro Pro His
            705                 710                 715 aga atc tgc agt ttt gaa gag gca aag ggt ttg gat agg atc aat gag   2811
```

```
                Arg Ile Cys Ser Phe Glu Glu Ala Lys Gly Leu Asp Arg Ile Asn Glu
                        720                 725                 730 aga atg cca cct cgg aaa gat gct gta cag caa gat ggt ttc aat tct         2859
Arg Met Pro Pro Arg Lys Asp Ala Val Gln Gln Asp Gly Phe Asn Ser
        735                 740                 745 ctg aac acc gca cat gcc act gag aac cac ggg acg ggc aac cat act         2907
Leu Asn Thr Ala His Ala Thr Glu Asn His Gly Thr Gly Asn His Thr
750                 755                 760                 765 gcc cag tga ttaactaggg taccccggga tccaccggat ctagataact                 2956
Ala Gln gatcataatc agccatacca catttgtaga ggttttactt gctttaaaaa acctcccaca       3016 cctcccctg aacctgaaac ataaaatgaa tgcaattgtt gttgttaact tgtttattgc        3076
agcttataat ggttacaaat aaagcaatag catcacaaat tcacaaata aagcattttt        3136 ttcactgcat tctagttgtg gtttgtccaa actcatcaat gtatcttaac gcgtaaattg       3196
taagcgttaa tattttgtta aaattcgcgt taaattttg ttaaatcagc tcatttttta       3256
accaataggc cgaaatcggc aaaatccctt ataaatcaaa agaatagacc gagatagggt      3316
tgagtgttgt tccagtttgg aacaagagtc cactattaaa gaacgtggac tccaacgtca      3376
aagggcgaaa aaccgtctat cagggcgatg gcccactacg tgaaccatca ccctaatcaa      3436
gttttttggg gtcgaggtgc cgtaaagcac taaatcggaa ccctaaaggg agcccccgat      3496
ttagagcttg acggggaaag ccggcgaacg tggcgagaaa ggaagggaag aaagcgaaag      3556
gagcgggcgc tagggcgctg gcaagtgtag cggtcacgct gcgcgtaacc accacacccg      3616
ccgcgcttaa tgcgccgcta cagggcgcgt caggtggcac ttttcgggga aatgtgcgcg      3676 gaaccctat ttgtttattt ttctaaatac attcaaatat gtatccgctc atgagacaat       3736
aaccctgata aatgcttcaa taatattgaa aaaggaagag tcctgaggcg aaagaaccca     3796
gctgtggaat gtgtgtcagt tagggtgtgg aaagtcccca ggctcccag caggcagaag      3856 tatgcaaagc atgcatctca attagtcagc aaccaggtgt ggaaagtccc caggctcccc    3916
agcaggcaga gtatgcaaaa gcatgcatct caattagtca gcaaccatag tcccgccct     3976 aactccgccc atcccgcccc taactccgcc cagttccgcc cattctccgc cccatggctg     4036
actaattttt tttatttatg cagaggccga ggccgcctcg gcctctgagc tattccagaa     4096
gtagtgagga ggctttttg gaggcctagg cttttgcaaa gatcgatcaa gagacaggat     4156
gaggatcgtt tcgcatgatt gaacaagatg gattgcacgc aggttctccg gccgcttggg    4216
tggagaggct attcggctat gactgggcac aacagacaat cggctgctct gatgccgccg    4276
tgttccggct gtcagcgcag gggcgcccgg ttcttttgt caagaccgac ctgtccggtg    4336
ccctgaatga actgcaagac gaggcagcgc ggctatcgtg gctggccacg acgggcgttc   4396
cttgcgcagc tgtgctcgac gttgtcactg aagcgggaag ggactggctg ctattgggcg   4456
aagtgccggg gcaggatctc ctgtcatctc accttgctcc tgccgagaaa gtatccatca   4516
tggctgatgc aatgcggcgg ctgcatacgc ttgatccggc tacctgccca ttcgaccacc   4576
aagcgaaaca tcgcatcgag cgagcacgta ctcggatgga agccggtctt gtcgatcagg   4636
atgatctgga cgaagagcat caggggctcg cgccagccga actgttcgcc aggctcaagg   4696
cgagcatgcc cgacgcgag gatctcgtcg tgacccatgg cgatgcctgc ttgccgaata   4756
tcatggtgga aaatggccgc ttttctggat tcatcgactg tggccggctg ggtgtggcgg   4816
accgctatca ggacatagcg ttggctaccc gtgatattgc tgaagagctt ggcggcgaat   4876
gggctgaccg cttcctcgtg ctttacggta tcgccgctcc cgattcgcag cgcatcgcct   4936
```

-continued

```
tctatcgcct tcttgacgag ttcttctgag cgggactctg gggttcgaaa tgaccgacca    4996
agcgacgccc aacctgccat cacgagattt cgattccacc gccgccttct atgaaaggtt    5056
gggcttcgga atcgttttcc gggacgccgg ctggatgatc ctccagcgcg gggatctcat    5116
gctggagttc ttcgcccacc ctaggggag gctaactgaa acacggaagg agacaatacc    5176
ggaaggaacc cgcgctatga cggcaataaa aagacagaat aaaacgcacg gtgttgggtc    5236
gtttgttcat aaacgcgggg ttcggtccca gggctggcac tctgtcgata ccccaccgag    5296
accccattgg ggccaatacg cccgcgtttc ttccttttcc ccacccccacc cccaagttc    5356 gggtgaaggc ccagggctcg cagccaacgt cggggcggca ggccctgcca tagcctcagg    5416
ttactcatat atactttaga ttgatttaaa acttcatttt taatttaaaa ggatctaggt    5476
gaagatcctt tttgataatc tcatgaccaa atcccttaa cgtgagtttt cgttccactg    5536
agcgtcagac cccgtagaaa agatcaaagg atcttcttga gatccttttt ttctgcgcgt    5596
aatctgctgc ttgcaaacaa aaaaccacc gctaccagcg gtggtttgtt tgccggatca    5656
agagctacca actcttttc cgaaggtaac tggcttcagc agagcgcaga taccaaatac    5716
tgtccttcta gtgtagccgt agttaggcca ccacttcaag aactctgtag caccgcctac    5776
atacctcgct ctgctaatcc tgttaccagt ggctgctgcc agtggcgata agtcgtgtct    5836 taccggttg gactcaagac gatagttacc ggataaggcg cagcggtcgg gctgaacggg    5896
gggttcgtgc acacagccca gcttggagcg aacgacctac accgaactga gatacctaca    5956
gcgtgagcta tgagaaagcg ccacgcttcc gaagggaga aaggcggaca ggtatccggt    6016
aagcggcagg gtcggaacag gagagcgcac gagggagctt ccaggggaa acgcctggta    6076 tctttatagt cctgtcgggt ttcgccacct ctgacttgag cgtcgatttt tgtgatgctc    6136 gtcaggggg cggagcctat ggaaaaacgc cagcaacgcg gcctttttac ggttcctggc    6196
cttttgctgg ccttttgctc acatgttctt tcctgcgtta tccctgatt ctgtggataa    6256 ccgtattacc gccatgcat                                                  6275
```

<210> SEQ ID NO 8
<211> LENGTH: 239
<212> TYPE: PRT
<213> ORGANISM: Homo sapiens

<400> SEQUENCE: 8

```
Met Val Ser Lys Gly Glu Glu Leu Phe Thr Gly Val Val Pro Ile Leu
  1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
     50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125
```

```
Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235
```

<210> SEQ ID NO 9
<211> LENGTH: 528
<212> TYPE: PRT
<213> ORGANISM: Homo sapiens

<400> SEQUENCE: 9

```
Ser Gly Leu Arg Ser Ala Ala Pro Glu Pro Ala Arg Ala Ala Pro Pro
1               5                   10                  15

Pro Pro Pro Pro Pro Pro Pro Gly Ala Asp Arg Val Val Lys
                20                  25                  30

Ala Val Pro Phe Pro Pro Thr His Arg Leu Thr Ser Glu Glu Val Phe
            35                  40                  45

Asp Leu Asp Gly Ile Pro Arg Val Asp Val Leu Lys Asn His Leu Val
    50                  55                  60

Lys Glu Gly Arg Val Asp Glu Glu Ile Ala Leu Arg Ile Ile Asn Glu
65                  70                  75                  80

Gly Ala Ala Ile Leu Arg Arg Glu Lys Thr Met Ile Glu Val Glu Ala
                85                  90                  95

Pro Ile Thr Val Cys Gly Asp Ile His Gly Gln Phe Phe Asp Leu Met
            100                 105                 110

Lys Leu Phe Glu Val Gly Gly Ser Pro Ala Asn Thr Arg Tyr Leu Phe
        115                 120                 125

Leu Gly Asp Tyr Val Asp Arg Gly Tyr Phe Ser Ile Glu Cys Val Leu
    130                 135                 140

Tyr Leu Trp Val Leu Lys Ile Leu Tyr Pro Ser Thr Leu Phe Leu Leu
145                 150                 155                 160

Arg Gly Asn His Glu Cys Arg His Leu Thr Glu Tyr Phe Thr Phe Lys
                165                 170                 175

Gln Glu Cys Lys Ile Lys Tyr Ser Glu Arg Val Tyr Glu Ala Cys Met
            180                 185                 190

Glu Ala Phe Asp Ser Leu Pro Leu Ala Ala Leu Leu Asn Gln Gln Phe
        195                 200                 205

Leu Cys Val His Gly Gly Leu Ser Pro Glu Ile His Thr Leu Asp Asp
    210                 215                 220

Ile Arg Arg Leu Asp Arg Phe Lys Glu Pro Pro Ala Phe Gly Pro Met
225                 230                 235                 240

Cys Asp Leu Leu Trp Ser Asp Pro Ser Glu Asp Phe Gly Asn Glu Lys
                245                 250                 255

Ser Gln Glu His Phe Ser His Asn Thr Val Arg Gly Cys Ser Tyr Phe
            260                 265                 270
```

```
Tyr Asn Tyr Pro Ala Val Cys Glu Phe Leu Gln Asn Asn Asn Leu Leu
        275                 280                 285
Ser Ile Ile Arg Ala His Glu Ala Gln Asp Ala Gly Tyr Arg Met Tyr
        290                 295                 300
Arg Lys Ser Gln Thr Thr Gly Phe Pro Ser Leu Ile Thr Ile Phe Ser
305                 310                 315                 320
Ala Pro Asn Tyr Leu Asp Val Tyr Asn Lys Ala Ala Val Leu Lys
                325                 330                 335
Tyr Glu Asn Asn Val Met Asn Ile Arg Gln Phe Asn Cys Ser Pro His
            340                 345                 350
Pro Tyr Trp Leu Pro Asn Phe Met Asp Val Phe Thr Trp Ser Leu Pro
        355                 360                 365
Phe Val Gly Glu Lys Val Thr Glu Met Leu Val Asn Val Leu Ser Ile
        370                 375                 380
Cys Ser Asp Asp Glu Leu Met Thr Glu Gly Glu Asp Gln Phe Asp Gly
385                 390                 395                 400
Ser Ala Ala Arg Lys Glu Ile Ile Arg Asn Lys Ile Arg Ala Ile
                405                 410                 415
Gly Lys Met Ala Arg Val Phe Ser Val Leu Arg Glu Glu Ser Glu Ser
            420                 425                 430
Val Leu Thr Leu Lys Gly Leu Thr Pro Thr Gly Met Leu Pro Ser Gly
        435                 440                 445
Val Leu Ala Gly Gly Arg Gln Thr Leu Gln Ser Ala Thr Val Glu Ala
        450                 455                 460
Ile Glu Ala Glu Lys Ala Ile Arg Gly Phe Ser Pro Pro His Arg Ile
465                 470                 475                 480
Cys Ser Phe Glu Glu Ala Lys Gly Leu Asp Arg Ile Asn Glu Arg Met
                485                 490                 495
Pro Pro Arg Lys Asp Ala Val Gln Gln Asp Gly Phe Asn Ser Leu Asn
            500                 505                 510
Thr Ala His Ala Thr Glu Asn His Gly Thr Gly Asn His Thr Ala Gln
        515                 520                 525

<210> SEQ ID NO 10
<211> LENGTH: 6218
<212> TYPE: DNA
<213> ORGANISM: Homo sapiens
<220> FEATURE:
<221> NAME/KEY: CDS
<222> LOCATION: (613)..(1329)
<223> OTHER INFORMATION: enhanced green fluorescent protein
<221> NAME/KEY: CDS
<222> LOCATION: (1330)..(2856)
<223> OTHER INFORMATION: calcineurin A gamma

<400> SEQUENCE: 10
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
```

-continued

```
ggactttcca aaatgtcgta acaactccgc cccattgacg caaatgggcg gtaggcgtgt    540
acggtgggag gtctatataa gcagagctgg tttagtgaac cgtcagatcc gctagcgcta    600
ccggtcgcca cc atg gtg agc aag ggc gag gag ctg ttc acc ggg gtg gtg    651
              Met Val Ser Lys Gly Glu Glu Leu Phe Thr Gly Val Val
                1               5                  10 ccc atc ctg gtc gag ctg gac ggc gac gta aac ggc cac aag ttc agc     699
Pro Ile Leu Val Glu Leu Asp Gly Asp Val Asn Gly His Lys Phe Ser
 15              20                  25 gtg tcc ggc gag ggc gag ggc gat gcc acc tac ggc aag ctg acc ctg     747
Val Ser Gly Glu Gly Glu Gly Asp Ala Thr Tyr Gly Lys Leu Thr Leu
 30              35                  40                  45 aag ttc atc tgc acc acc ggc aag ctg ccc gtg ccc tgg ccc acc ctc     795
Lys Phe Ile Cys Thr Thr Gly Lys Leu Pro Val Pro Trp Pro Thr Leu
                 50                  55                  60 gtg acc acc ctg acc tac ggc gtg cag tgc ttc agc cgc tac ccc gac     843
Val Thr Thr Leu Thr Tyr Gly Val Gln Cys Phe Ser Arg Tyr Pro Asp
                 65                  70                  75 cac atg aag cag cac gac ttc ttc aag tcc gcc atg ccc gaa ggc tac     891
His Met Lys Gln His Asp Phe Phe Lys Ser Ala Met Pro Glu Gly Tyr
             80                  85                  90 gtc cag gag cgc acc atc ttc ttc aag gac gac ggc aac tac aag acc     939
Val Gln Glu Arg Thr Ile Phe Phe Lys Asp Asp Gly Asn Tyr Lys Thr
             95                 100                 105 cgc gcc gag gtg aag ttc gag ggc gac acc ctg gtg aac cgc atc gag     987
Arg Ala Glu Val Lys Phe Glu Gly Asp Thr Leu Val Asn Arg Ile Glu
110                 115                 120                 125 ctg aag ggc atc gac ttc aag gag gac ggc aac atc ctg ggg cac aag    1035
Leu Lys Gly Ile Asp Phe Lys Glu Asp Gly Asn Ile Leu Gly His Lys
                130                 135                 140 ctg gag tac aac tac aac agc cac aac gtc tat atc atg gcc gac aag    1083
Leu Glu Tyr Asn Tyr Asn Ser His Asn Val Tyr Ile Met Ala Asp Lys
                145                 150                 155 cag aag aac ggc atc aag gtg aac ttc aag atc cgc cac aac atc gag    1131
Gln Lys Asn Gly Ile Lys Val Asn Phe Lys Ile Arg His Asn Ile Glu
                160                 165                 170 gac ggc agc gtg cag ctc gcc gac cac tac cag cag aac acc ccc atc    1179
Asp Gly Ser Val Gln Leu Ala Asp His Tyr Gln Gln Asn Thr Pro Ile
175                 180                 185 ggc gac ggc ccc gtg ctg ctg ccc gac aac cac tac ctg agc acc cag    1227
Gly Asp Gly Pro Val Leu Leu Pro Asp Asn His Tyr Leu Ser Thr Gln
190                 195                 200                 205 tcc gcc ctg agc aaa gac ccc aac gag aag cgc gat cac atg gtc ctg    1275
Ser Ala Leu Ser Lys Asp Pro Asn Glu Lys Arg Asp His Met Val Leu
                210                 215                 220 ctg gag ttc gtg acc gcc gcc ggg atc act ctc ggc atg gac gag ctg    1323
Leu Glu Phe Val Thr Ala Ala Gly Ile Thr Leu Gly Met Asp Glu Leu
                225                 230                 235 tac aag tcc gga ctc aga tcc aga tcc atg tcc ggg agg cgc ttc cac    1371
Tyr Lys Ser Gly Leu Arg Ser Arg Ser Met Ser Gly Arg Arg Phe His
                240                 245                 250 ctc tcc acc acc gac cgc gtc atc aaa gct gtc ccc ttt cct cca acc    1419
Leu Ser Thr Thr Asp Arg Val Ile Lys Ala Val Pro Phe Pro Pro Thr
255                 260                 265 caa cgg ctt act ttc aag gaa gta ttt gag aat ggg aaa cct aaa gtt    1467
Gln Arg Leu Thr Phe Lys Glu Val Phe Glu Asn Gly Lys Pro Lys Val
270                 275                 280                 285 gat gtt tta aaa aac cat ttg gta aag gaa gga cga ctg gaa gag gaa    1515
Asp Val Leu Lys Asn His Leu Val Lys Glu Gly Arg Leu Glu Glu Glu
```

-continued

```
                        290                       295                       300
gta gcc tta aag ata atc aat gat ggg gct gcc atc ctg agg caa gag         1563
Val Ala Leu Lys Ile Ile Asn Asp Gly Ala Ala Ile Leu Arg Gln Glu
            305                       310                       315 aag act atg ata gaa gta gat gct cca atc aca gta tgt ggt gat att         1611
Lys Thr Met Ile Glu Val Asp Ala Pro Ile Thr Val Cys Gly Asp Ile
                320                       325                       330 cat gga caa ttc ttt gac cta atg aag tta ttt gaa gtt gga gga tca         1659
His Gly Gln Phe Phe Asp Leu Met Lys Leu Phe Glu Val Gly Gly Ser
    335                       340                       345 cct agt aac aca cgc tac ctc ttt ctg ggt gac tat gtg gac aga ggc         1707
Pro Ser Asn Thr Arg Tyr Leu Phe Leu Gly Asp Tyr Val Asp Arg Gly
350                       355                       360                       365 tat ttc agt ata gag tgt gtg ctg tat tta tgg agt tta aag att aat         1755
Tyr Phe Ser Ile Glu Cys Val Leu Tyr Leu Trp Ser Leu Lys Ile Asn
                370                       375                       380 cat ccc aaa aca ttg ttt ctg ctt cgg gga aat cat gaa tgc agg cat         1803
His Pro Lys Thr Leu Phe Leu Leu Arg Gly Asn His Glu Cys Arg His
            385                       390                       395 ctt aca gac tat ttc acc ttc aaa cag gaa tgt cga atc aaa tat tcg         1851
Leu Thr Asp Tyr Phe Thr Phe Lys Gln Glu Cys Arg Ile Lys Tyr Ser
        400                       405                       410 gaa cag gtg tat gat gcc tgt atg gag aca ttt gac tgt ctt cct ctt         1899
Glu Gln Val Tyr Asp Ala Cys Met Glu Thr Phe Asp Cys Leu Pro Leu
    415                       420                       425 gct gcc ctc tta aac cag cag ttt ctc tgt gta cat gga gga atg tca         1947
Ala Ala Leu Leu Asn Gln Gln Phe Leu Cys Val His Gly Gly Met Ser
430                       435                       440                       445 cct gaa att act tct tta gat gac att agg aaa tta gac agg ttt acg         1995
Pro Glu Ile Thr Ser Leu Asp Asp Ile Arg Lys Leu Asp Arg Phe Thr
                450                       455                       460 gaa cct ccc gcc ttt gga cct gtg tgt gac ctg ctt tgg tct gat ccc         2043
Glu Pro Pro Ala Phe Gly Pro Val Cys Asp Leu Leu Trp Ser Asp Pro
            465                       470                       475 tca gag gat tat ggc aat gag aag acc ttg gag cac tat acc cac aac         2091
Ser Glu Asp Tyr Gly Asn Glu Lys Thr Leu Glu His Tyr Thr His Asn
        480                       485                       490 act gtc cga ggg tgc tct tat ttc tac agt tac cct gca gtt tgt gaa         2139
Thr Val Arg Gly Cys Ser Tyr Phe Tyr Ser Tyr Pro Ala Val Cys Glu
    495                       500                       505 ttt ttg cag aac aat aat tta cta tca att atc aga gcc cat gaa gcc         2187
Phe Leu Gln Asn Asn Asn Leu Leu Ser Ile Ile Arg Ala His Glu Ala
510                       515                       520                       525 caa gat gct ggg tat cga atg tac agg aag agc caa gcc aca ggc ttt         2235
Gln Asp Ala Gly Tyr Arg Met Tyr Arg Lys Ser Gln Ala Thr Gly Phe
                530                       535                       540 cca tca ctt att aca att ttc tct gcc ccc aat tac cta gat gtc tat         2283
Pro Ser Leu Ile Thr Ile Phe Ser Ala Pro Asn Tyr Leu Asp Val Tyr
            545                       550                       555 aac aat aaa gct gct gtg ttg aaa tat gaa aac aat gtc atg aat atc         2331
Asn Asn Lys Ala Ala Val Leu Lys Tyr Glu Asn Asn Val Met Asn Ile
        560                       565                       570 agg cag ttt aac tgt tct cca cac ccc tac tgg ctt cca aac ttt atg         2379
Arg Gln Phe Asn Cys Ser Pro His Pro Tyr Trp Leu Pro Asn Phe Met
    575                       580                       585 gat gtt ttc aca tgg tct ttg cct ttt gtt ggg gaa aaa gtc aca gag         2427
Asp Val Phe Thr Trp Ser Leu Pro Phe Val Gly Glu Lys Val Thr Glu
590                       595                       600                       605 atg ctg gta aat gtg ctc aac ata tgc tct gat gac gaa ctg att tct         2475
Met Leu Val Asn Val Leu Asn Ile Cys Ser Asp Asp Glu Leu Ile Ser
```

```
                                                                -continued

Met Leu Val Asn Val Leu Asn Ile Cys Ser Asp Asp Glu Leu Ile Ser
            610                 615                 620 gat gat gaa gca gaa gga agc act aca gtt cgt aag gag atc atc agg        2523
Asp Asp Glu Ala Glu Gly Ser Thr Thr Val Arg Lys Glu Ile Ile Arg
            625                 630                 635 aat aag atc aga gcc att ggg aag atg gca cgg gtc ttt tca att ctt        2571
Asn Lys Ile Arg Ala Ile Gly Lys Met Ala Arg Val Phe Ser Ile Leu
            640                 645                 650 cgg caa gaa agt gag agt gtg ctg act ctc aag ggc ctg act ccc aca        2619
Arg Gln Glu Ser Glu Ser Val Leu Thr Leu Lys Gly Leu Thr Pro Thr
        655                 660                 665 ggc aca ctc cct ctg ggc gtc ctc tca gga ggc aag cag act atc gag        2667
Gly Thr Leu Pro Leu Gly Val Leu Ser Gly Gly Lys Gln Thr Ile Glu
670                 675                 680                 685 aca gcc atc aga ggg ttc tcg ctt cag cac aag atc cgg agt ttt gaa        2715
Thr Ala Ile Arg Gly Phe Ser Leu Gln His Lys Ile Arg Ser Phe Glu
                690                 695                 700 gaa gcg cga ggt ctg gac cga att aat gag cga atg cca ccc cga aag        2763
Glu Ala Arg Gly Leu Asp Arg Ile Asn Glu Arg Met Pro Pro Arg Lys
            705                 710                 715 gat agc ata tac cct ggt ggg cca atg aaa tct gta acc tca gca cac        2811
Asp Ser Ile Tyr Pro Gly Gly Pro Met Lys Ser Val Thr Ser Ala His
            720                 725                 730 tca cat gct gcg cac agg agc gac caa ggg aag aaa gcc cat tca            2856
Ser His Ala Ala His Arg Ser Asp Gln Gly Lys Lys Ala His Ser
735                 740                 745 tgattaacta gggtacccccg ggatccaccg gatctagata actgatcata atcagccata     2916
ccacatttgt agaggtttta cttgctttaa aaaacctccc acacctcccc ctgaacctga      2976
aacataaaat gaatgcaatt gttgttgtta acttgtttat tgcagcttat aatggttaca      3036
aataaagcaa tagcatcaca aatttcacaa ataaagcatt ttttcactg cattctagtt       3096 gtggtttgtc caaactcatc aatgtatctt aacgcgtaaa ttgtaagcgt taatattttg      3156
ttaaaattcg cgttaaattt tgttaaatc agctcatttt ttaaccaata ggccgaaatc       3216
ggcaaaatcc cttataaatc aaaagaatag accgagatag ggttgagtgt tgttccagtt      3276
tggaacaaga gtccactatt aaagaacgtg gactccaacg tcaaagggcg aaaaaccgtc      3336
tatcagggcg atggcccact acgtgaacca tcacccctaat caagttttttt ggggtcgagg    3396 tgccgtaaag cactaaatcg aaccctaaa gggagcccccc gatttagagc ttgacgggga     3456
aagccggcga acgtggcgag aaaggaaggg aagaaagcga aaggagcggg cgctagggcg      3516
ctggcaagtg tagcggtcac gctgcgcgta accaccacac ccgccgcgct taatgcgccg     3576
ctacagggcg cgtcaggtgg cacttttcgg ggaaatgtgc gcggaacccc tatttgttta     3636 ttttttctaaa tacattcaaa tatgtatccg ctcatgagac aataaccctg ataaatgctt    3696
caataatatt gaaaaaggaa gagtcctgag gcggaaagaa ccagctgtgg aatgtgtgtc     3756
agttagggtg tggaaagtcc ccaggctccc cagcaggcag aagtatgcaa agcatgcatc     3816
tcaattagtc agcaaccagg tgtggaaagt ccccaggctc cccagcaggc agaagtatgc     3876
aaagcatgca tctcaattag tcagcaacca tagtcccgcc cctaactccg cccatcccgc     3936
ccctaactcc gcccagttcc gcccattctc cgccccatgg ctgactaatt ttttttattt     3996
atgcagaggc cgaggccgcc tcggcctctg agctattcca gaagtagtga ggaggctttt     4056
ttggaggcct aggcttttgc aaagatcgat caagagacag gatgaggatc gtttcgcatg     4116
attgaacaag atggattgca cgcaggttct ccggccgctt gggtggagag gctattcggc     4176
```

| | |
|---|---|
| tatgactggg cacaacagac aatcggctgc tctgatgccg ccgtgttccg gctgtcagcg | 4236 |
| caggggcgcc cggttcttt tgtcaagacc gacctgtccg gtgccctgaa tgaactgcaa | 4296 |
| gacgaggcag cgcggctatc gtggctggcc acgacgggcg ttccttgcgc agctgtgctc | 4356 |
| gacgttgtca ctgaagcggg aagggactgg ctgctattgg gcgaagtgcc ggggcaggat | 4416 |
| ctcctgtcat ctcaccttgc tcctgccgag aaagtatcca tcatggctga tgcaatgcgg | 4476 |
| cggctgcata cgcttgatcc ggctacctgc ccattcgacc accaagcgaa acatcgcatc | 4536 |
| gagcgagcac gtactcggat ggaagccggt cttgtcgatc aggatgatct ggacgaagag | 4596 |
| catcaggggc tcgcgccagc cgaactgttc gccaggctca aggcgagcat gcccgacggc | 4656 |
| gaggatctcg tcgtgaccca tggcgatgcc tgcttgccga atatcatggt ggaaaatggc | 4716 |
| cgcttttctg gattcatcga ctgtggccgg ctgggtgtgg cggaccgcta tcaggacata | 4776 |
| gcgttggcta cccgtgatat tgctgaagag cttggcggcg aatgggctga ccgcttcctc | 4836 |
| gtgctttacg gtatcgccgc tcccgattcg cagcgcatcg ccttctatcg ccttcttgac | 4896 |
| gagttcttct gagcgggact ctggggttcg aaatgaccga ccaagcgacg cccaacctgc | 4956 |
| catcacgaga tttcgattcc accgccgcct tctatgaaag gttgggcttc ggaatcgttt | 5016 |
| tccgggacgc cggctggatg atcctccagc gcggggatct catgctggag ttcttcgccc | 5076 |
| accctagggg gaggctaact gaaacacgga aggagacaat accggaagga cccgcgcta | 5136 |
| tgacggcaat aaaaagacag aataaaacgc acggtgttgg gtcgtttgtt cataaacgcg | 5196 |
| gggttcggtc ccagggctgg cactctgtcg ataccccacc gagacccat tggggccaat | 5256 |
| acgcccgcgt tcttcctttt tccccacccc accccccaag ttcgggtgaa ggcccagggc | 5316 |
| tcgcagccaa cgtcggggcg gcaggccctg ccatagcctc aggttactca tatatacttt | 5376 |
| agattgattt aaaacttcat ttttaattta aaaggatcta ggtgaagatc cttttgata | 5436 |
| atctcatgac caaaatccct taacgtgagt tttcgttcca ctgagcgtca gaccccgtag | 5496 |
| aaaagatcaa aggatcttct tgagatcctt ttttctgcg cgtaatctgc tgcttgcaaa | 5556 |
| caaaaaaacc accgctacca gcggtggttt gtttgccgga tcaagagcta ccaactcttt | 5616 |
| ttccgaaggt aactggcttc agcagagcgc agataccaaa tactgtcctt ctagtgtagc | 5676 |
| cgtagttagg ccaccacttc aagaactctg tagcaccgcc tacatacctc gctctgctaa | 5736 |
| tcctgttacc agtggctgct gccagtggcg ataagtcgtg tcttaccggg ttggactcaa | 5796 |
| gacgatagtt accggataag gcgcagcggt cgggctgaac ggggggttcg tgcacacagc | 5856 |
| ccagcttgga gcgaacgacc tacaccgaac tgagatacct acagcgtgag ctatgagaaa | 5916 |
| gcgccacgct tcccgaaggg agaaaggcgg acaggtatcc ggtaagcggc agggtcggaa | 5976 |
| caggagagcg cacgagggag cttccagggg gaaacgcctg gtatctttat agtcctgtcg | 6036 |
| ggtttcgcca cctctgactt gagcgtcgat ttttgtgatg ctcgtcaggg gggcggagcc | 6096 |
| tatgaaaaa cgccagcaac gcggcctttt tacggttcct ggccttttgc tggccttttg | 6156 |
| ctcacatgtt ctttcctgcg ttatcccctg attctgtgga taaccgtatt accgccatgc | 6216 |
| at | 6218 |

<210> SEQ ID NO 11
<211> LENGTH: 239
<212> TYPE: PRT
<213> ORGANISM: Homo sapiens

<400> SEQUENCE: 11

Met Val Ser Lys Gly Glu Glu Leu Phe Thr Gly Val Val Pro Ile Leu

```
  1               5                  10                 15
Val Glu Leu Asp Gly Asp Val Asn Gly His Lys Phe Ser Val Ser Gly
             20                 25                 30

Glu Gly Glu Gly Asp Ala Thr Tyr Gly Lys Leu Thr Leu Lys Phe Ile
             35                 40                 45

Cys Thr Thr Gly Lys Leu Pro Val Pro Trp Pro Thr Leu Val Thr Thr
 50                 55                 60

Leu Thr Tyr Gly Val Gln Cys Phe Ser Arg Tyr Pro Asp His Met Lys
 65                 70                 75                 80

Gln His Asp Phe Phe Lys Ser Ala Met Pro Glu Gly Tyr Val Gln Glu
                 85                 90                 95

Arg Thr Ile Phe Phe Lys Asp Asp Gly Asn Tyr Lys Thr Arg Ala Glu
                100                105                110

Val Lys Phe Glu Gly Asp Thr Leu Val Asn Arg Ile Glu Leu Lys Gly
            115                120                125

Ile Asp Phe Lys Glu Asp Gly Asn Ile Leu Gly His Lys Leu Glu Tyr
130                135                140

Asn Tyr Asn Ser His Asn Val Tyr Ile Met Ala Asp Lys Gln Lys Asn
145                150                155                160

Gly Ile Lys Val Asn Phe Lys Ile Arg His Asn Ile Glu Asp Gly Ser
                165                170                175

Val Gln Leu Ala Asp His Tyr Gln Gln Asn Thr Pro Ile Gly Asp Gly
            180                185                190

Pro Val Leu Leu Pro Asp Asn His Tyr Leu Ser Thr Gln Ser Ala Leu
            195                200                205

Ser Lys Asp Pro Asn Glu Lys Arg Asp His Met Val Leu Leu Glu Phe
210                215                220

Val Thr Ala Ala Gly Ile Thr Leu Gly Met Asp Glu Leu Tyr Lys
225                230                235

<210> SEQ ID NO 12
<211> LENGTH: 509
<212> TYPE: PRT
<213> ORGANISM: Homo sapiens

<400> SEQUENCE: 12

Ser Gly Leu Arg Ser Arg Ser Met Ser Gly Arg Arg Phe His Leu Ser
  1               5                 10                 15

Thr Thr Asp Arg Val Ile Lys Ala Val Pro Phe Pro Thr Gln Arg
             20                 25                 30

Leu Thr Phe Lys Glu Val Phe Glu Asn Gly Lys Pro Lys Val Asp Val
             35                 40                 45

Leu Lys Asn His Leu Val Lys Glu Gly Arg Leu Glu Glu Val Ala
         50                 55                 60

Leu Lys Ile Ile Asn Asp Gly Ala Ala Ile Leu Arg Gln Glu Lys Thr
 65                 70                 75                 80

Met Ile Glu Val Asp Ala Pro Ile Thr Val Cys Gly Asp Ile His Gly
                 85                 90                 95

Gln Phe Phe Asp Leu Met Lys Leu Phe Glu Val Gly Gly Ser Pro Ser
                100                105                110

Asn Thr Arg Tyr Leu Phe Leu Gly Asp Tyr Val Asp Arg Gly Tyr Phe
            115                120                125

Ser Ile Glu Cys Val Leu Tyr Leu Trp Ser Leu Lys Ile Asn His Pro
130                135                140
```

```
Lys Thr Leu Phe Leu Leu Arg Gly Asn His Glu Cys Arg His Leu Thr
145                 150                 155                 160

Asp Tyr Phe Thr Phe Lys Gln Glu Cys Arg Ile Lys Tyr Ser Glu Gln
            165                 170                 175

Val Tyr Asp Ala Cys Met Glu Thr Phe Asp Cys Leu Pro Leu Ala Ala
        180                 185                 190

Leu Leu Asn Gln Gln Phe Leu Cys Val His Gly Gly Met Ser Pro Glu
    195                 200                 205

Ile Thr Ser Leu Asp Asp Ile Arg Lys Leu Asp Arg Phe Thr Glu Pro
210                 215                 220

Pro Ala Phe Gly Pro Val Cys Asp Leu Leu Trp Ser Asp Pro Ser Glu
225                 230                 235                 240

Asp Tyr Gly Asn Glu Lys Thr Leu Glu His Tyr Thr His Asn Thr Val
            245                 250                 255

Arg Gly Cys Ser Tyr Phe Tyr Ser Tyr Pro Ala Val Cys Glu Phe Leu
        260                 265                 270

Gln Asn Asn Asn Leu Leu Ser Ile Ile Arg Ala His Glu Ala Gln Asp
    275                 280                 285

Ala Gly Tyr Arg Met Tyr Arg Lys Ser Gln Ala Thr Gly Phe Pro Ser
290                 295                 300

Leu Ile Thr Ile Phe Ser Ala Pro Asn Tyr Leu Asp Val Tyr Asn Asn
305                 310                 315                 320

Lys Ala Ala Val Leu Lys Tyr Glu Asn Asn Val Met Asn Ile Arg Gln
            325                 330                 335

Phe Asn Cys Ser Pro His Pro Tyr Trp Leu Pro Asn Phe Met Asp Val
        340                 345                 350

Phe Thr Trp Ser Leu Pro Phe Val Gly Glu Lys Val Thr Glu Met Leu
    355                 360                 365

Val Asn Val Leu Asn Ile Cys Ser Asp Asp Glu Leu Ile Ser Asp Asp
370                 375                 380

Glu Ala Glu Gly Ser Thr Thr Val Arg Lys Glu Ile Ile Arg Asn Lys
385                 390                 395                 400

Ile Arg Ala Ile Gly Lys Met Ala Arg Val Phe Ser Ile Leu Arg Gln
            405                 410                 415

Glu Ser Glu Ser Val Leu Thr Leu Lys Gly Leu Thr Pro Thr Gly Thr
        420                 425                 430

Leu Pro Leu Gly Val Leu Ser Gly Gly Lys Gln Thr Ile Glu Thr Ala
    435                 440                 445

Ile Arg Gly Phe Ser Leu Gln His Lys Ile Arg Ser Phe Glu Glu Ala
450                 455                 460

Arg Gly Leu Asp Arg Ile Asn Glu Arg Met Pro Pro Arg Lys Asp Ser
465                 470                 475                 480

Ile Tyr Pro Gly Gly Pro Met Lys Ser Val Thr Ser Ala His Ser His
            485                 490                 495

Ala Ala His Arg Ser Asp Gln Gly Lys Lys Ala His Ser
        500                 505

<210> SEQ ID NO 13
<211> LENGTH: 3975
<212> TYPE: DNA
<213> ORGANISM: Homo sapiens
<220> FEATURE:
<221> NAME/KEY: misc_feature
<222> LOCATION: (115)..(150)
<223> OTHER INFORMATION: histidine tag
<221> NAME/KEY: misc_feature
```

```
<222> LOCATION: (148)..(153)
<223> OTHER INFORMATION: cathepsin-C cleavage site
<221> NAME/KEY: CDS
<222> LOCATION: (151)..(612)
<223> OTHER INFORMATION: copper/zinc superoxide dismutase

<400> SEQUENCE: 13
ctcgagaaat cataaaaaat ttatttgctt tgtgagcgga taacaattat aatagattca      60
attgtgagcg gataacaatt tcacacagaa ttcattaaag aggagaaatt aactatgaga     120
ggatcgcatc accatcacca tcacggatcc gcg acg aag gcc gtg tgc gtg ctg     174
                                 Ala Thr Lys Ala Val Cys Val Leu
                                  1               5 aag ggc gac ggc cca gtg cag ggc atc atc aat ttc gag cag aag gaa     222
Lys Gly Asp Gly Pro Val Gln Gly Ile Ile Asn Phe Glu Gln Lys Glu
 10              15                  20 agt aat gga cca gtg aag gtg tgg gga agc att aaa gga ctg act gaa     270
Ser Asn Gly Pro Val Lys Val Trp Gly Ser Ile Lys Gly Leu Thr Glu
 25              30                  35                  40 ggc ctg cat gga ttc cat gtt cat gag ttt gga gat aat aca gca ggc     318
Gly Leu His Gly Phe His Val His Glu Phe Gly Asp Asn Thr Ala Gly
                 45                  50                  55 tgt acc agt gca ggt cct cac ttt aat cct cta tcc aga aaa cac ggt     366
Cys Thr Ser Ala Gly Pro His Phe Asn Pro Leu Ser Arg Lys His Gly
             60                  65                  70 ggg cca aag gat gaa gag agg cat gtt gga gac ttg ggc aat gtg act     414
Gly Pro Lys Asp Glu Glu Arg His Val Gly Asp Leu Gly Asn Val Thr
         75                  80                  85 gct gac aaa gat ggt gtg gcc gat gtg tct att gaa gat tct gtg atc     462
Ala Asp Lys Asp Gly Val Ala Asp Val Ser Ile Glu Asp Ser Val Ile
 90                  95                 100 tca ctc tca gga gac cat tgc atc att ggc cgc aca ctg gtg gtc cat     510
Ser Leu Ser Gly Asp His Cys Ile Ile Gly Arg Thr Leu Val Val His
105                 110                 115                 120 gaa aaa gca gat gac ttg ggc aaa ggt gga aat gaa gaa agt aca aag     558
Glu Lys Ala Asp Asp Leu Gly Lys Gly Gly Asn Glu Glu Ser Thr Lys
                125                 130                 135 aca gga aac gct gga agt cgt ttg gct tgt ggt gta att ggg atc gcc     606
Thr Gly Asn Ala Gly Ser Arg Leu Ala Cys Gly Val Ile Gly Ile Ala
            140                 145                 150 caa taa ttcgaaccca gccgaattc cagcacactg gcggccgtta ctagtggatc      662
Gln cgcatgcgag tcggtaccc cgggtcgacc tgcagccaag cttaattagc tgagcttgga      722
ctcctgttga tagatccagt aatgacctca gaactccatc tggatttgtt cagaacgctc      782
ggttgccgcc gggcgttttt tattggtgag aatccaagct agcttggcga gattttcagg      842
agctaaggaa gctaaaatgg agaaaaaaat cactggatat accaccgttg atatatccca      902
atggcatcgt aaagaacatt tgaggcatt tcagtcagtt gctcaatgta cctataacca      962
gaccgttcag ctggatatta cggcctttt aaagaccgta agaaaaata agcacaagtt     1022 ttatccggcc tttattcaca ttcttgcccg cctgatgaat gctcatccgg aatttcgtat     1082
ggcaatgaaa gacggtgagc tggtgatatg ggatagtgtt cacccttgtt acaccgtttt     1142
ccatgagcaa actgaaacgt tttcatcgct ctggagtgaa taccacgacg atttccggca     1202
gtttctacac atatattcgc aagatgtggc gtgttacggt gaaaacctgg cctatttccc     1262
taaagggttt attgagaata tgttttttcgt ctcagccaat ccctgggtga gtttcaccag     1322
ttttgattta aacgtggcca atatggacaa cttcttcgcc cccgttttca ccatgggcaa     1382
```

```
atattatacg caaggcgaca aggtgctgat gccgctggcg attcaggttc atcatgccgt   1442
ctgtgatggc ttccatgtcg gcagaatgct taatgaatta caacagtact gcgatgagtg   1502
gcagggcggg gcgtaatttt tttaaggcag ttattggtgc ccttaaacgc ctggggtaat   1562
gactctctag cttgaggcat caaataaaac gaaaggctca gtcgaaagac tgggcctttc   1622
gttttatctg ttgtttgtcg gtgaacgctc tcctgagtag gacaaatccg ccgctctaga   1682
gctgcctcgc gcgtttcggt gatgacggtg aaaacctctg acacatgcag ctcccggaga   1742
cggtcacagc ttgtctgtaa gcggatgccg ggagcagaca gcccgtcag gcgcgtcag    1802 cgggtgttgg cgggtgtcgg ggcgcagcca tgacccagtc acgtagcgat agcggagtgt   1862
atactggctt aactatgcgg catcagagca gattgtactg agagtgcacc atatgcggtg   1922
tgaaataccg cacagatgcg taaggagaaa ataccgcatc aggcgctctt ccgcttcctc   1982
gctcactgac tcgctgcgct cggtctgtcg gctgcggcga gcggtatcag ctcactcaaa   2042
ggcggtaata cggttatcca cagaatcagg ggataacgca ggaaagaaca tgtgagcaaa   2102
aggccagcaa aaggccagga accgtaaaaa ggccgcgttg ctggcgtttt tccataggct   2162
ccgcccccct gacgagcatc acaaaaatcg acgctcaagt cagaggtggc gaaacccgac   2222
aggactataa agataccagg cgtttccccc tggaagctcc ctcgtgcgct ctcctgttcc   2282
gaccctgccg cttaccggat acctgtccgc ctttctccct tcgggaagcg tggcgctttc   2342
tcaatgctca cgctgtaggt atctcagttc ggtgtaggtc gttcgctcca agctgggctg   2402
tgtgcacgaa ccccccgttc agcccgaccg ctgcgcctta ccggtaact atcgtcttga   2462 gtccaacccg gtaagacacg acttatcgcc actggcagca gccactggta acaggattag   2522
cagagcgagg tatgtaggcg gtgctacaga gttcttgaag tggtggccta actacggcta   2582
cactagaagg acagtatttg gtatctgcgc tctgctgaag ccagttacct tcggaaaaag   2642
agttggtagc tcttgatccg gcaaacaaac caccgctggt agcggtggtt ttttgtttg    2702 caagcagcag attacgcgca gaaaaaaagg atctcaagaa gatcctttga tcttttctac   2762
ggggtctgac gctcagtgga acgaaaactc acgttaaggg attttggtca tgagattatc   2822
aaaaaggatc ttcacctaga tccttttaaa ttaaaaatga gttttaaat caatctaaag    2882 tatatatgag taaacttggt ctgacagtta ccaatgctta atcagtgagg cacctatctc   2942
agcgatctgt ctatttcgtt catccatagc tgcctgactc cccgtcgtgt agataactac   3002
gatacgggag ggcttaccat ctggccccag tgctgcaatg ataccgcgag acccacgctc   3062
accggctcca gatttatcag caataaacca gccagccgga agggccgagc gcagaagtgg   3122
tcctgcaact ttatccgcct ccatccagtc tattaattgt tgccgggaag ctagagtaag   3182
tagttcgcca gttaatagtt tgcgcaacgt tgttgccatt gctacaggca tcgtggtgtc   3242
acgctcgtcg tttggtatgg cttcattcag ctccggttcc caacgatcaa ggcgagttac   3302
atgatccccc atgttgtgca aaaaagcggt tagctccttc ggtcctccga tcgttgtcag   3362
aagtaagttg gccgcagtgt tatcactcat ggttatggca gcactgcata attctcttac   3422
tgtcatgcca tccgtaagat gcttttctgt gactggtgag tactcaacca agtcattctg   3482
agaatagtgt atgcggcgac cgagttgctc ttgcccggcg tcaatacggg ataataccgc   3542
gccacatagc agaactttaa aagtgctcat cattggaaaa cgttcttcgg ggcgaaaact   3602
ctcaaggatc ttaccgctgt tgagatccag ttcgatgtaa cccactcgtg cacccaactg   3662
atcttcagca tcttttactt tcaccagcgt ttctgggtga gcaaaacag gaaggcaaaa    3722 tgccgcaaaa aagggaataa gggcgacacg gaaatgttga atactcatac tcttcctttt   3782
```

```
tcaatattat tgaagcattt atcagggtta ttgtctcatg agcggataca tatttgaatg   3842
tatttagaaa ataaacaaa tagggttcc gcgcacattt ccccgaaaag tgccacctga    3902
cgtctaagaa accattatta tcatgacatt aacctataaa aataggcgta tcacgaggcc   3962
ctttcgtctt cac                                                      3975

<210> SEQ ID NO 14
<211> LENGTH: 153
<212> TYPE: PRT
<213> ORGANISM: Homo sapiens

<400> SEQUENCE: 14

Ala Thr Lys Ala Val Cys Val Leu Lys Gly Asp Gly Pro Val Gln Gly
  1               5                  10                  15

Ile Ile Asn Phe Glu Gln Lys Glu Ser Asn Gly Pro Val Lys Val Trp
             20                  25                  30

Gly Ser Ile Lys Gly Leu Thr Glu Gly Leu His Gly Phe His Val His
         35                  40                  45

Glu Phe Gly Asp Asn Thr Ala Gly Cys Thr Ser Ala Gly Pro His Phe
     50                  55                  60

Asn Pro Leu Ser Arg Lys His Gly Gly Pro Lys Asp Glu Glu Arg His
 65                  70                  75                  80

Val Gly Asp Leu Gly Asn Val Thr Ala Asp Lys Asp Gly Val Ala Asp
                 85                  90                  95

Val Ser Ile Glu Asp Ser Val Ile Ser Leu Ser Gly Asp His Cys Ile
            100                 105                 110

Ile Gly Arg Thr Leu Val Val His Glu Lys Ala Asp Asp Leu Gly Lys
        115                 120                 125

Gly Gly Asn Glu Glu Ser Thr Lys Thr Gly Asn Ala Gly Ser Arg Leu
    130                 135                 140

Ala Cys Gly Val Ile Gly Ile Ala Gln
145                 150

<210> SEQ ID NO 15
<211> LENGTH: 3881
<212> TYPE: DNA
<213> ORGANISM: Homo sapiens
<220> FEATURE:
<221> NAME/KEY: CDS
<222> LOCATION: (115)..(576)
<223> OTHER INFORMATION: copper/zinc superoxide dismutase
<221> NAME/KEY: misc_feature
<222> LOCATION: (577)..(582)
<223> OTHER INFORMATION: carboxypeptidase-A cleavage site
<221> NAME/KEY: misc_feature
<222> LOCATION: (578)..(603)
<223> OTHER INFORMATION: histidine tag

<400> SEQUENCE: 15
ctcgagaaat cataaaaaat ttatttgctt tgtgagcgga taacaattat aatagattca    60
attgtgagcg gataacaatt tcacacagaa ttcattaaag gagagaaatt aacc atg     117
                                                              Met
                                                                1 gcg acg aag gcc gtg tgc gtg ctg aag ggc gac ggc cca gtg cag ggc     165
Ala Thr Lys Ala Val Cys Val Leu Lys Gly Asp Gly Pro Val Gln Gly
          5                  10                  15 atc atc aat ttc gag cag aag gaa agt aat gga cca gtg aag gtg tgg     213
Ile Ile Asn Phe Glu Gln Lys Glu Ser Asn Gly Pro Val Lys Val Trp
         20                  25                  30
```

-continued

| | | |
|---|---|---|
| gga agc att aaa gga ctg act gaa ggc ctg cat gga ttc cat gtt cat<br>Gly Ser Ile Lys Gly Leu Thr Glu Gly Leu His Gly Phe His Val His<br>35                  40                  45 | | 261 |
| gag ttt gga gat aat aca gca ggc tgt acc agt gca ggt cct cac ttt<br>Glu Phe Gly Asp Asn Thr Ala Gly Cys Thr Ser Ala Gly Pro His Phe<br>50                  55                  60                  65 | | 309 |
| aat cct cta tcc aga aaa cac ggt ggg cca aag gat gaa gag agg cat<br>Asn Pro Leu Ser Arg Lys His Gly Gly Pro Lys Asp Glu Glu Arg His<br>                  70                  75                  80 | | 357 |
| gtt gga gac ttg ggc aat gtg act gct gac aaa gat ggt gtg gcc gat<br>Val Gly Asp Leu Gly Asn Val Thr Ala Asp Lys Asp Gly Val Ala Asp<br>85                  90                  95 | | 405 |
| gtg tct att gaa gat tct gtg atc tca ctc tca gga gac cat tgc atc<br>Val Ser Ile Glu Asp Ser Val Ile Ser Leu Ser Gly Asp His Cys Ile<br>100                105              110 | | 453 |
| att ggc cgc aca ctg gtg gtc cat gaa aaa gca gat gac ttg ggc aaa<br>Ile Gly Arg Thr Leu Val Val His Glu Lys Ala Asp Asp Leu Gly Lys<br>115                120              125 | | 501 |
| ggt gga aat gaa gaa agt aca aag aca gga aac gct gga agt cgt ttg<br>Gly Gly Asn Glu Glu Ser Thr Lys Thr Gly Asn Ala Gly Ser Arg Leu<br>130                135              140              145 | | 549 |
| gct tgt ggt gta att ggg atc gcc caa agatctcatc accatcacca<br>Ala Cys Gly Val Ile Gly Ile Ala Gln<br>                  150 | | 596 |
| tcactaagct taattagctg agcttggact cctgttgata gatccagtaa tgacctcaga | | 1656 |
| actccatctg gatttgttca gaacgctcgg ttgccgccgg gcgttttta ttggtgagaa | | 1716 |
| tccaagctag cttggcgaga ttttcaggag ctaaggaagc taaaatggag aaaaaaatca | | 1776 |
| ctggatatac caccgttgat atatcccaat ggcatcgtaa agaacatttt gaggcatttc | | 1836 |
| agtcagttgc tcaatgtacc tataaccaga ccgttcagct ggatattacg gcctttttaa | | 1896 |
| agaccgtaaa gaaaaataag cacaagtttt atccggcctt tattcacatt cttgcccgcc | | 1956 |
| tgatgaatgc tcatccggaa tttcgtatgg caatgaaaga cggtgagctg gtgatatggg | 1016 |
| atagtgttca cccttgttac accgttttcc atgagcaaac tgaaacgttt tcatcgctct | 1076 |
| ggagtgaata ccacgacgat ttccggcagt ttctacacat atattcgcaa gatgtggcgt | 1136 |
| gttacggtga aaacctggcc tatttcccta aagggtttat tgagaatatg ttttcgtct | 1196 |
| cagccaatcc ctgggtgagt ttcaccagtt ttgatttaaa cgtggccaat atggacaact | 1256 |
| tcttcgcccc cgttttcacc atgcatgggc aaatattata cgcaaggcga caaggtgctg | 1316 |
| atgccgctgg cgattcaggt tcatcatgcc gtctgtgatg gcttccatgt cggcagaatg | 1376 |
| cttaatgaat tacaacagta ctgcgatgag tggcagggcg ggcgtaatt tttttaaggc | 1436 |
| agttattggt gcccttaaac gcctggggta atgactctct agcttgaggc atcaaataaa | 1496 |
| acgaaaggct cagtcgaaag actgggcctt tcgttttatc tgttgtttgt cggtgaacgc | 1556 |
| tctcctgagt aggacaaatc cgccgctcta gagctgcctc gcgcgtttcg gtgatgacgg | 1616 |
| tgaaaacctc tgacacatgc agctcccgga cggtcaca gcttgtctgt aagcggatgc | 1676 |
| cgggagcaga caagcccgtc agggcgcgtc agcgggtgtt ggcgggtgtc ggggcgcagc | 1736 |
| catgacccag tcacgtagcg atagcggagt gtatactggc ttaactatgc ggcatcagag | 1796 |
| cagattgtac tgagagtgca ccatatgcgg tgtgaaatac cgcacagatg cgtaaggaga | 1856 |
| aaataccgca tcaggcgctc ttccgcttcc tcgctcactg actcgctgcg ctcggtctgt | 1916 |
| cggctgcggc gagcggtatc agctcactca aaggcggtaa tacggttatc cacagaatca | 1976 |
| ggggataacg caggaaagaa catgtgagca aaaggccagc aaaaggccag gaaccgtaaa | 2036 |

-continued

```
aaggccgcgt tgctggcgtt tttccatagg ctccgccccc ctgacgagca tcacaaaaat    2096
cgacgctcaa gtcagaggtg gcgaaacccg acaggactat aaagatacca ggcgtttccc    2156
cctggaagct ccctcgtgcg ctctcctgtt ccgaccctgc cgcttaccgg atacctgtcc    2216
gcctttctcc cttcgggaag cgtggcgctt tctcaatgct cacgctgtag gtatctcagt    2276
tcggtgtagg tcgttcgctc caagctgggc tgtgtgcacg aaccccccgt tcagcccgac    2336
cgctgcgcct tatccggtaa ctatcgtctt gagtccaacc cggtaagaca cgacttatcg    2396
ccactggcag cagccactgg taacaggatt agcagagcga ggtatgtagg cggtgctaca    2456
gagttcttga agtggtggcc taactacggc tacactagaa ggacagtatt tggtatctgc    2516
gctctgctga agccagttac cttcggaaaa agagttggta gctcttgatc cggcaaacaa    2576
accaccgctg gtagcggtgg ttttttttgtt tgcaagcagc agattacgcg cagaaaaaaa    2636
ggatctcaag aagatccttt gatcttttct acggggtctg acgctcagtg gaacgaaaac    2696
tcacgttaag ggattttggt catgagatta tcaaaagga tcttcaccta gatccttta    2756
aattaaaaat gaagttttaa atcaatctaa agtatatatg agtaaacttg gtctgacagt    2816
taccaatgct taatcagtga ggcacctatc tcagcgatct gtctatttcg ttcatccata    2876
gctgcctgac tccccgtcgt gtagataact acgatacggg agggcttacc atctggcccc    2936
agtgctgcaa tgataccgcg agacccacgc tcaccggctc cagatttatc agcaataaac    2996
cagccagccg gaagggccga gcgcagaagt ggtcctgcaa ctttatccgc ctccatccag    3056
tctattaatt gttgccggga agctagagta agtagttcgc cagttaatag tttgcgcaac    3116
gttgttgcca ttgctacagg catcgtggtg tcacgctcgt cgtttggtat ggcttcattc    3176
agctccggtt cccaacgatc aaggcgagtt acatgatccc ccatgttgtg caaaaaagcg    3236
gttagctcct tcggtcctcc gatcgttgtc agaagtaagt tggccgcagt gttatcactc    3296
atggttatgg cagcactgca taattctctt actgtcatgc catccgtaag atgcttttct    3356
gtgactggtg agtactcaac caagtcattc tgagaatagt gtatgcggcg accgagttgc    3416
tcttgcccgg cgtcaatacg ggataatacc gcgccacata gcagaacttt aaaagtgctc    3476
atcattggaa aacgttcttc ggggcgaaaa ctctcaagga tcttaccgct gttgagatcc    3536
agttcgatgt aacccactcg tgcacccaac tgatcttcag catctttac tttcaccagc    3596
gtttctgggt gagcaaaaac aggaaggcaa atgccgcaa aaagggaat aagggcgaca    3656
cggaaatgtt gaatactcat actcttcctt tttcaatatt attgaagcat ttatcagggt    3716
tattgtctca tgagcggata catatttgaa tgtatttaga aaataaaca aatagggtt    3776
ccgcgcacat ttccccgaaa agtgccacct gacgtctaag aaaccattat tatcatgaca    3836
ttaacctata aaataggcg tatcacgagg ccctttcgtc ttcac                     3881
```

<210> SEQ ID NO 16
<211> LENGTH: 154
<212> TYPE: PRT
<213> ORGANISM: Homo sapiens

<400> SEQUENCE: 16

```
Met Ala Thr Lys Ala Val Cys Val Leu Lys Gly Asp Gly Pro Val Gln
  1               5                  10                  15

Gly Ile Ile Asn Phe Glu Gln Lys Glu Ser Asn Gly Pro Val Lys Val
             20                  25                  30

Trp Gly Ser Ile Lys Gly Leu Thr Glu Gly Leu His Gly Phe His Val
         35                  40                  45
```

```
His Glu Phe Gly Asp Asn Thr Ala Gly Cys Thr Ser Ala Gly Pro His
 50                  55                  60

Phe Asn Pro Leu Ser Arg Lys His Gly Pro Lys Asp Glu Glu Arg
 65                  70                  75                  80

His Val Gly Asp Leu Gly Asn Val Thr Ala Asp Lys Asp Gly Val Ala
                 85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
            115                 120                 125

Lys Gly Gly Asn Glu Glu Ser Thr Lys Thr Gly Asn Ala Gly Ser Arg
            130                 135                 140

Leu Ala Cys Gly Val Ile Gly Ile Ala Gln
145                 150

<210> SEQ ID NO 17
<211> LENGTH: 5555
<212> TYPE: DNA
<213> ORGANISM: Homo sapiens
<220> FEATURE:
<221> NAME/KEY: CDS
<222> LOCATION: (115)..(1713)
<223> OTHER INFORMATION: histidine tagged calcineurin A alpha1
<221> NAME/KEY: misc_feature
<222> LOCATION: (1714)..(1758)
<223> OTHER INFORMATION: ribosomal binding site, multiple cloning site 2
<221> NAME/KEY: CDS
<222> LOCATION: (1759)..(2268)
<223> OTHER INFORMATION: calcineurin B
<221> NAME/KEY: variation
<222> LOCATION: (115)..(1713)
<223> OTHER INFORMATION: splicevariant: histidine tagged calcineurin A
      alpha1 lacking pos. 208 - 2317 ( phosphatase domain), newly
      generated N-terminus exhibits protease activity

<400> SEQUENCE: 17
ctcgagaaat cataaaaaat ttatttgctt tgtgagcgga taacaattat aatagattca    60
attgtgagcg gataacaatt tcacacagaa ttcattaaag aggagaaatt aactatg     117
                                                             Met
                                                              1 aga gga tcg cat cac cat cac cat cac gga tcc atg tcc gag ccc aag    165
Arg Gly Ser His His His His His His Gly Ser Met Ser Glu Pro Lys
              5                  10                  15 gca att gat ccc aag ttg tcg acg acc gac agg gtg gtg aaa gct gtt    213
Ala Ile Asp Pro Lys Leu Ser Thr Thr Asp Arg Val Val Lys Ala Val
         20                  25                  30 cca ttt cct cca agt cac cgg ctt aca gca aaa gaa gtg ttt gat aat    261
Pro Phe Pro Pro Ser His Arg Leu Thr Ala Lys Glu Val Phe Asp Asn
 35                  40                  45 gat gga aaa cct cgt gtg gat atc tta aag gcg cat ctt atg aag gag    309
Asp Gly Lys Pro Arg Val Asp Ile Leu Lys Ala His Leu Met Lys Glu
 50                  55                  60                  65 gga agg ctg gaa gag agt gtt gca ttg aga ata ata aca gag ggt gca    357
Gly Arg Leu Glu Glu Ser Val Ala Leu Arg Ile Ile Thr Glu Gly Ala
                 70                  75                  80 tca att ctt cga cag gaa aaa aat ttg ctg gat att gat gcg cca gtc    405
Ser Ile Leu Arg Gln Glu Lys Asn Leu Leu Asp Ile Asp Ala Pro Val
             85                  90                  95 act gtt tgt ggg gac att cat gga caa ttc ttt gat ttg atg aag ctc    453
Thr Val Cys Gly Asp Ile His Gly Gln Phe Phe Asp Leu Met Lys Leu
        100                 105                 110
```

```
ttt gaa gtc ggg gga tct cct gcc aac act cgc tac ctc ttc tta ggg       501
Phe Glu Val Gly Gly Ser Pro Ala Asn Thr Arg Tyr Leu Phe Leu Gly
    115                 120                 125 gac tat gtt gac aga ggg tac ttc agt att gaa tgt gtg ctg tat ttg       549
Asp Tyr Val Asp Arg Gly Tyr Phe Ser Ile Glu Cys Val Leu Tyr Leu
130                 135                 140                 145 tgg gcc ttg aaa att ctc tac ccc aaa aca ctg ttt tta ctt cgt gga       597
Trp Ala Leu Lys Ile Leu Tyr Pro Lys Thr Leu Phe Leu Leu Arg Gly
                150                 155                 160 aat cat gaa tgt aga cat cta aca gag tat ttc aca ttt aaa caa gaa       645
Asn His Glu Cys Arg His Leu Thr Glu Tyr Phe Thr Phe Lys Gln Glu
            165                 170                 175 tgt aaa ata aag tat tca gaa cga gta tat gat gcc tgt atg gat gcc       693
Cys Lys Ile Lys Tyr Ser Glu Arg Val Tyr Asp Ala Cys Met Asp Ala
        180                 185                 190 ttt gac tgc ctt ccc ctg gct gcc ctg atg aac caa cag ttc ctg tgt       741
Phe Asp Cys Leu Pro Leu Ala Ala Leu Met Asn Gln Gln Phe Leu Cys
195                 200                 205 gtg cat ggt ggt ttg tct cca gag att aac act tta gat gat atc aga       789
Val His Gly Gly Leu Ser Pro Glu Ile Asn Thr Leu Asp Asp Ile Arg
210                 215                 220                 225 aaa tta gac cga ttc aaa gaa cca cct gca tat gga cct atg tgt gat       837
Lys Leu Asp Arg Phe Lys Glu Pro Pro Ala Tyr Gly Pro Met Cys Asp
                230                 235                 240 atc ctg tgg tca gac ccc ctg gaa gat ttt gga aat gag aag act cag       885
Ile Leu Trp Ser Asp Pro Leu Glu Asp Phe Gly Asn Glu Lys Thr Gln
            245                 250                 255 gaa cat ttc act cac aac aca gtc agg ggg tgt tca tac ttc tac agt       933
Glu His Phe Thr His Asn Thr Val Arg Gly Cys Ser Tyr Phe Tyr Ser
        260                 265                 270 tac ccg gct gta tgt gaa ttc tta cag cac aat aac ttg tta tct ata       981
Tyr Pro Ala Val Cys Glu Phe Leu Gln His Asn Asn Leu Leu Ser Ile
275                 280                 285 ctc cga gcc cac gaa gcc caa gat gca ggg tac cgc atg tac agg aaa      1029
Leu Arg Ala His Glu Ala Gln Asp Ala Gly Tyr Arg Met Tyr Arg Lys
290                 295                 300                 305 agc caa aca aca ggc ttc cct tct cta att aca att ttt tca gca cca      1077
Ser Gln Thr Thr Gly Phe Pro Ser Leu Ile Thr Ile Phe Ser Ala Pro
                310                 315                 320 aat tac tta gat gta tac aat aac aaa gct gca gta ttg aag tat gag      1125
Asn Tyr Leu Asp Val Tyr Asn Asn Lys Ala Ala Val Leu Lys Tyr Glu
            325                 330                 335 aac aat gtt atg aat atc agg caa ttc aac tgt tct cct cat cca tac      1173
Asn Asn Val Met Asn Ile Arg Gln Phe Asn Cys Ser Pro His Pro Tyr
        340                 345                 350 tgg ctt cca aat ttc atg gat gtt ttt act tgg tcc ctt cca ttt gtt      1221
Trp Leu Pro Asn Phe Met Asp Val Phe Thr Trp Ser Leu Pro Phe Val
355                 360                 365 ggg gaa aaa gtg act gag atg ctg gta aat gtc ctc aac atc tgc tca      1269
Gly Glu Lys Val Thr Glu Met Leu Val Asn Val Leu Asn Ile Cys Ser
370                 375                 380                 385 gat gat gaa cta ggg tca gaa gaa gat gga ttt gat ggt gca aca gct      1317
Asp Asp Glu Leu Gly Ser Glu Glu Asp Gly Phe Asp Gly Ala Thr Ala
                390                 395                 400 gca gcc cgg aaa gag gtg ata agg aac aag atc cga gca ata ggc aaa      1365
Ala Ala Arg Lys Glu Val Ile Arg Asn Lys Ile Arg Ala Ile Gly Lys
            405                 410                 415 atg gcc aga gtg ttc tca gtg ctc aga gaa gag agt gag agt gtg ctg      1413
Met Ala Arg Val Phe Ser Val Leu Arg Glu Glu Ser Glu Ser Val Leu
420                 425                 430
```

```
acg ctg aaa ggc ttg acc cca act ggc atg ctc ccc agc gga gta ctt      1461
Thr Leu Lys Gly Leu Thr Pro Thr Gly Met Leu Pro Ser Gly Val Leu
        435                 440                 445 tct gga ggg aag caa acc ctg caa agc gct act gtt gag gct att gag      1509
Ser Gly Gly Lys Gln Thr Leu Gln Ser Ala Thr Val Glu Ala Ile Glu
450                 455                 460                 465 gct gat gaa gct atc aaa gga ttt tca cca caa cat aag atc act agc      1557
Ala Asp Glu Ala Ile Lys Gly Phe Ser Pro Gln His Lys Ile Thr Ser
                470                 475                 480 ttc gag gaa gcc aag ggc tta gac cga att aat gag agg atg ccg cct      1605
Phe Glu Glu Ala Lys Gly Leu Asp Arg Ile Asn Glu Arg Met Pro Pro
            485                 490                 495 cgc aga gat gcc atg ccc tct gac gcc aac ctt aac tcc atc aac aag      1653
Arg Arg Asp Ala Met Pro Ser Asp Ala Asn Leu Asn Ser Ile Asn Lys
        500                 505                 510 gct ctc acc tca gag act aac ggc acg gac agc aat ggc agt aat agc      1701
Ala Leu Thr Ser Glu Thr Asn Gly Thr Asp Ser Asn Gly Ser Asn Ser
    515                 520                 525 agc aat att cag tga ttaactaggg taccccgggg taccaaagag gagaaattaa      1756
Ser Asn Ile Gln
530 ct atg gga aat gag gca agt tat cct ttg gaa atg tgc tca cac ttt       1803
   Met Gly Asn Glu Ala Ser Tyr Pro Leu Glu Met Cys Ser His Phe
       535                 540                 545 gat gca gat gaa att aaa agg cta gga aag aga ttt aag aag ctc gat      1851
Asp Ala Asp Glu Ile Lys Arg Leu Gly Lys Arg Phe Lys Lys Leu Asp
550                 555                 560                 565 ttg gac aat tct ggt tct ttg agt gtg gaa gag ttc atg tct cta cct      1899
Leu Asp Asn Ser Gly Ser Leu Ser Val Glu Glu Phe Met Ser Leu Pro
                570                 575                 580 gag tta caa cag aat ccc tta gta cag cga gta ata gat ata ttc gac      1947
Glu Leu Gln Gln Asn Pro Leu Val Gln Arg Val Ile Asp Ile Phe Asp
            585                 590                 595 aca gat ggg aat gga gaa gta gac ttt aaa gag ttc att gag gga gtc      1995
Thr Asp Gly Asn Gly Glu Val Asp Phe Lys Glu Phe Ile Glu Gly Val
        600                 605                 610 tct cag ttc agt gtc aaa gga gat aag gaa cag aag ttg agg ttt gct      2043
Ser Gln Phe Ser Val Lys Gly Asp Lys Glu Gln Lys Leu Arg Phe Ala
    615                 620                 625 ttc cgt atc tat gac atg gat aaa gac ggc tat att tcc aat ggg gaa      2091
Phe Arg Ile Tyr Asp Met Asp Lys Asp Gly Tyr Ile Ser Asn Gly Glu
630                 635                 640                 645 ctc ttc cag gtg cta aag atg atg gtg ggg aac aat ctg aaa gat aca      2139
Leu Phe Gln Val Leu Lys Met Met Val Gly Asn Asn Leu Lys Asp Thr
                650                 655                 660 cag tta cag caa att gta gac aaa acc ata ata aat gca gat aag gat      2187
Gln Leu Gln Gln Ile Val Asp Lys Thr Ile Ile Asn Ala Asp Lys Asp
            665                 670                 675 ggg gat gga aga ata tcc ttt gaa gaa ttc tgt gct gtt gta ggc ggc      2235
Gly Asp Gly Arg Ile Ser Phe Glu Glu Phe Cys Ala Val Val Gly Gly
        680                 685                 690 cta gat atc cac aaa aag atg gtg gta gat gtg tga ttaattagaa           2281
Leu Asp Ile His Lys Lys Met Val Val Asp Val
    695                 700                 705 gcttaattag ctgagcttgg actcctgttg atagatccag taatgacctc agaactccat    2341
ctggatttgt tcagaacgct cggttgccgc cgggcgtttt ttattggtga aatccaagc     2401 tagcttggcg agattttcag gagctaagga agctaaaatg gagaaaaaaa tcactggata    2461
```

```
taccaccgtt gatatatccc aatggcatcg taaagaacat tttgaggcat tcagtcagt    2521 tgctcaatgt acctataacc agaccgttca gctggatatt acggccttt taaagaccgt    2581 aaagaaaaat aagcacaagt tttatccggc ctttattcac attcttgccc gcctgatgaa    2641
tgctcatccg gaatttcgta tggcaatgaa agacggtgag ctggtgatat gggatagtgt    2701
tcacccttgt tacaccgttt tccatgagca aactgaaacg ttttcatcgc tctggagtga    2761
ataccacgac gatttccggc agtttctaca catatattcg caagatgtgg cgtgttacgg    2821
tgaaaacctg gcctatttcc ctaaaggggtt tattgagaat atgttttcg tctcagccaa    2881 tccctgggtg agtttcacca gttttgattt aaacgtggcc aatatggaca acttcttcgc    2941
ccccgttttc accatgggca atattatac gcaaggcgac aaggtgctga tgccgctggc    3001
gattcaggtt catcatgccg tctgtgatgg cttccatgtc ggcagaatgc ttaatgaatt    3061
acaacagtac tgcgatgagt ggcagggcgg ggcgtaattt ttttaaggca gttattggtg    3121
cccttaaacg cctgggggtaa tgactctcta gcttgaggca tcaaataaaa cgaaaggctc    3181
agtcgaaaga ctgggccttt cgttttatct gttgtttgtc ggtgaacgct ctcctgagta    3241
ggacaaatcc gccgctctag agctgcctcg cgcgtttcgg tgatgacggt gaaaacctct    3301
gacacatgca gctcccggag acggtcacag cttgtctgta agcggatgcc gggagcagac    3361
aagcccgtca gggcgcgtca gcgggtgttg gcgggtgtcg gggcgcagcc atgacccagt    3421
cacgtagcga tagcggagtg tatactggct taactatgcg gcatcagagc agattgtact    3481
gagagtgcac catatgcggt gtgaaatacc gcacagatgc gtaaggagaa ataccgcat    3541 caggcgctct tccgcttcct cgctcactga ctcgctgcgc tcggtctgtc ggctgcggcg    3601
agcggtatca gctcactcaa aggcggtaat acggttatcc acagaatcag gggataacgc    3661
aggaaagaac atgtgagcaa aaggccagca aaaggccagg aaccgtaaaa aggccgcgtt    3721
gctggcgttt ttccataggc tccgcccccc tgacgagcat cacaaaaatc gacgctcaag    3781
tcagaggtgg cgaaacccga caggactata aagataccag gcgtttcccc ctggaagctc    3841
cctcgtgcgc tctcctgttc cgaccctgcc gcttaccgga tacctgtccg cctttctccc    3901
ttcgggaagc gtggcgcttt ctcaatgctc acgctgtagg tatctcagtt cggtgtaggt    3961
cgttcgctcc aagctgggct gtgtgcacga accccccgtt cagcccgacc gctgcgcctt    4021
atccggtaac tatcgtcttg agtccaaccc ggtaagacac gacttatcgc cactggcagc    4081
agccactggt aacaggatta gcagagcgag gtatgtaggc ggtgctacag agttcttgaa    4141
gtggtggcct aactacggct acactagaag gacagtattt ggtatctgcg ctctgctgaa    4201
gccagttacc ttcggaaaaa gagttggtag ctcttgatcc ggcaaacaaa ccaccgctgg    4261
tagcggtggt ttttttgttt gcaagcagca gattacgcgc agaaaaaaag gatctcaaga    4321
agatcctttg atcttttcta cggggtctga cgctcagtgg aacgaaaact cacgttaagg    4381
gattttggtc atgagattat caaaaaggat cttcacctag atcctttaa attaaaaatg    4441 aagttttaaa tcaatctaaa gtatatatga gtaaacttgg tctgacagtt accaatgctt    4501
aatcagtgag gcacctatct cagcgatctg tctatttcgt tcatccatag ctgcctgact    4561
ccccgtcgtg tagataacta cgatacggga gggcttacca tctggcccca gtgctgcaat    4621
gataccgcga gacccacgct caccggctcc agatttatca gcaataaacc agccagccgg    4681
aagggccgag cgcagaagtg gtcctgcaac tttatccgcc tccatccagt ctattaattg    4741
ttgccgggaa gctagagtaa gtagttcgcc agttaatagt ttgcgcaacg ttgttgccat    4801
tgctacaggc atcgtggtgt cacgctcgtc gtttggtatg gcttcattca gctccggttc    4861
```

-continued

```
ccaacgatca aggcgagtta catgatcccc catgttgtgc aaaaaagcgg ttagctcctt    4921
cggtcctccg atcgttgtca gaagtaagtt ggccgcagtg ttatcactca tggttatggc    4981
agcactgcat aattctctta ctgtcatgcc atccgtaaga tgcttttctg tgactggtga    5041
gtactcaacc aagtcattct gagaatagtg tatgcggcga ccgagttgct cttgcccggc    5101
gtcaatacgg gataataccg cgccacatag cagaacttta aaagtgctca tcattggaaa    5161
acgttcttcg gggcgaaaac tctcaaggat cttaccgctg ttgagatcca gttcgatgta    5221
acccactcgt gcacccaact gatcttcagc atcttttact ttcaccagcg tttctgggtg    5281
agcaaaaaca ggaaggcaaa atgccgcaaa aaagggaata agggcgacac ggaaatgttg    5341
aatactcata ctcttccttt ttcaatatta ttgaagcatt tatcagggtt attgtctcat    5401
gagcggatac atatttgaat gtatttagaa aaataaacaa ataggggttc cgcgcacatt    5461
tccccgaaaa gtgccacctg acgtctaaga aaccattatt atcatgacat taacctataa    5521
aaataggcgt atcacgaggc cctttcgtct tcac                                5555
```

<210> SEQ ID NO 18
<211> LENGTH: 533
<212> TYPE: PRT
<213> ORGANISM: Homo sapiens

<400> SEQUENCE: 18

```
Met Arg Gly Ser His His His His His His Gly Ser Met Ser Glu Pro
 1               5                  10                  15

Lys Ala Ile Asp Pro Lys Leu Ser Thr Thr Asp Arg Val Val Lys Ala
            20                  25                  30

Val Pro Phe Pro Pro Ser His Arg Leu Thr Ala Lys Glu Val Phe Asp
        35                  40                  45

Asn Asp Gly Lys Pro Arg Val Asp Ile Leu Lys Ala His Leu Met Lys
    50                  55                  60

Glu Gly Arg Leu Glu Glu Ser Val Ala Leu Arg Ile Ile Thr Glu Gly
65                  70                  75                  80

Ala Ser Ile Leu Arg Gln Glu Lys Asn Leu Leu Asp Ile Asp Ala Pro
                85                  90                  95

Val Thr Val Cys Gly Asp Ile His Gly Gln Phe Phe Asp Leu Met Lys
           100                 105                 110

Leu Phe Glu Val Gly Gly Ser Pro Ala Asn Thr Arg Tyr Leu Phe Leu
       115                 120                 125

Gly Asp Tyr Val Asp Arg Gly Tyr Phe Ser Ile Glu Cys Val Leu Tyr
   130                 135                 140

Leu Trp Ala Leu Lys Ile Leu Tyr Pro Lys Thr Leu Phe Leu Leu Arg
145                 150                 155                 160

Gly Asn His Glu Cys Arg His Leu Thr Glu Tyr Phe Thr Phe Lys Gln
               165                 170                 175

Glu Cys Lys Ile Lys Tyr Ser Glu Arg Val Tyr Asp Ala Cys Met Asp
           180                 185                 190

Ala Phe Asp Cys Leu Pro Leu Ala Ala Leu Met Asn Gln Gln Phe Leu
       195                 200                 205

Cys Val His Gly Gly Leu Ser Pro Glu Ile Asn Thr Leu Asp Asp Ile
   210                 215                 220

Arg Lys Leu Asp Arg Phe Lys Glu Pro Pro Ala Tyr Gly Pro Met Cys
225                 230                 235                 240

Asp Ile Leu Trp Ser Asp Pro Leu Glu Asp Phe Gly Asn Glu Lys Thr
```

-continued

```
                245                 250                 255
Gln Glu His Phe Thr His Asn Thr Val Arg Gly Cys Ser Tyr Phe Tyr
            260                 265                 270

Ser Tyr Pro Ala Val Cys Glu Phe Leu Gln His Asn Asn Leu Leu Ser
        275                 280                 285

Ile Leu Arg Ala His Glu Ala Gln Asp Ala Gly Tyr Arg Met Tyr Arg
    290                 295                 300

Lys Ser Gln Thr Thr Gly Phe Pro Ser Leu Ile Thr Ile Phe Ser Ala
305                 310                 315                 320

Pro Asn Tyr Leu Asp Val Tyr Asn Asn Lys Ala Ala Val Leu Lys Tyr
                325                 330                 335

Glu Asn Asn Val Met Asn Ile Arg Gln Phe Asn Cys Ser Pro His Pro
            340                 345                 350

Tyr Trp Leu Pro Asn Phe Met Asp Val Phe Thr Trp Ser Leu Pro Phe
        355                 360                 365

Val Gly Glu Lys Val Thr Glu Met Leu Val Asn Val Leu Asn Ile Cys
    370                 375                 380

Ser Asp Asp Glu Leu Gly Ser Glu Glu Asp Gly Phe Asp Gly Ala Thr
385                 390                 395                 400

Ala Ala Ala Arg Lys Glu Val Ile Arg Asn Lys Ile Arg Ala Ile Gly
                405                 410                 415

Lys Met Ala Arg Val Phe Ser Val Leu Arg Glu Ser Glu Ser Val
            420                 425                 430

Leu Thr Leu Lys Gly Leu Thr Pro Thr Gly Met Leu Pro Ser Gly Val
        435                 440                 445

Leu Ser Gly Gly Lys Gln Thr Leu Gln Ser Ala Thr Val Glu Ala Ile
    450                 455                 460

Glu Ala Asp Glu Ala Ile Lys Gly Phe Ser Pro Gln His Lys Ile Thr
465                 470                 475                 480

Ser Phe Glu Glu Ala Lys Gly Leu Asp Arg Ile Asn Glu Arg Met Pro
                485                 490                 495

Pro Arg Arg Asp Ala Met Pro Ser Asp Ala Asn Leu Asn Ser Ile Asn
            500                 505                 510

Lys Ala Leu Thr Ser Glu Thr Asn Gly Thr Asp Ser Asn Gly Ser Asn
        515                 520                 525

Ser Ser Asn Ile Gln
    530

<210> SEQ ID NO 19
<211> LENGTH: 170
<212> TYPE: PRT
<213> ORGANISM: Homo sapiens

<400> SEQUENCE: 19

Met Gly Asn Glu Ala Ser Tyr Pro Leu Glu Met Cys Ser His Phe Asp
  1               5                  10                  15

Ala Asp Glu Ile Lys Arg Leu Gly Lys Arg Phe Lys Lys Leu Asp Leu
                 20                  25                  30

Asp Asn Ser Gly Ser Leu Ser Val Glu Glu Phe Met Ser Leu Pro Glu
             35                  40                  45

Leu Gln Gln Asn Pro Leu Val Gln Arg Val Ile Asp Ile Phe Asp Thr
         50                  55                  60

Asp Gly Asn Gly Glu Val Asp Phe Lys Glu Phe Ile Glu Gly Val Ser
 65                  70                  75                  80
```

```
Gln Phe Ser Val Lys Gly Asp Lys Glu Gln Lys Leu Arg Phe Ala Phe
                85                  90                  95

Arg Ile Tyr Asp Met Asp Lys Asp Gly Tyr Ile Ser Asn Gly Glu Leu
            100                 105                 110

Phe Gln Val Leu Lys Met Met Val Gly Asn Asn Leu Lys Asp Thr Gln
        115                 120                 125

Leu Gln Gln Ile Val Asp Lys Thr Ile Ile Asn Ala Asp Lys Asp Gly
130                 135                 140

Asp Gly Arg Ile Ser Phe Glu Glu Phe Cys Ala Val Gly Gly Leu
145                 150                 155                 160

Asp Ile His Lys Lys Met Val Val Asp Val
                165                 170

<210> SEQ ID NO 20
<211> LENGTH: 5525
<212> TYPE: DNA
<213> ORGANISM: Homo sapiens
<220> FEATURE:
<221> NAME/KEY: CDS
<222> LOCATION: (115)..(1686)
<223> OTHER INFORMATION: histidine tagged calcineurin A alpha2
<221> NAME/KEY: misc_feature
<222> LOCATION: (1687)..(1728)
<223> OTHER INFORMATION: ribosomal binding site, multiple cloning site 2
<221> NAME/KEY: CDS
<222> LOCATION: (1729)..(2241)
<223> OTHER INFORMATION: calcineurin B

<400> SEQUENCE: 20
ctcgagaaat cataaaaaat ttatttgctt tgtgagcgga taacaattat aatagattca    60
attgtgagcg gataacaatt tcacacagaa ttcattaaag aggagaaatt aact atg     117
                                                              Met
                                                                1 aga gga tcg cat cac cat cac cat cac gga tcc atg tcc gag ccc aag    165
Arg Gly Ser His His His His His His Gly Ser Met Ser Glu Pro Lys
          5                   10                  15 gca att gat ccc aag ttg tcg acg acc gac agg gtg gtg aaa gct gtt    213
Ala Ile Asp Pro Lys Leu Ser Thr Thr Asp Arg Val Val Lys Ala Val
         20                  25                  30 cca ttt cct cca agt cac cgg ctt aca gca aaa gaa gtg ttt gat aat    261
Pro Phe Pro Pro Ser His Arg Leu Thr Ala Lys Glu Val Phe Asp Asn
     35                  40                  45 gat gga aaa cct cgt gtg gat atc tta aag gcg cat ctt atg aag gag    309
Asp Gly Lys Pro Arg Val Asp Ile Leu Lys Ala His Leu Met Lys Glu
 50                  55                  60                  65 gga agg ctg gaa gag agt gtt gca ttg aga ata ata aca gag ggt gca    357
Gly Arg Leu Glu Glu Ser Val Ala Leu Arg Ile Ile Thr Glu Gly Ala
                 70                  75                  80 tca att ctt cga cag gaa aaa aat ttg ctg gat att gat gcg cca gtc    405
Ser Ile Leu Arg Gln Glu Lys Asn Leu Leu Asp Ile Asp Ala Pro Val
             85                  90                  95 act gtt tgt ggg gac att cat gga caa ttc ttt gat ttg atg aag ctc    453
Thr Val Cys Gly Asp Ile His Gly Gln Phe Phe Asp Leu Met Lys Leu
        100                 105                 110 ttt gaa gtc ggg gga tct cct gcc aac act cgc tac ctc ttc tta ggg    501
Phe Glu Val Gly Gly Ser Pro Ala Asn Thr Arg Tyr Leu Phe Leu Gly
    115                 120                 125 gac tat gtt gac aga ggg tac ttc agt att gaa tgt gtg ctg tat ttg    549
Asp Tyr Val Asp Arg Gly Tyr Phe Ser Ile Glu Cys Val Leu Tyr Leu
130                 135                 140                 145 tgg gcc ttg aaa att ctc tac ccc aaa aca ctg ttt tta ctt cgt gga    597
```

```
Trp Ala Leu Lys Ile Leu Tyr Pro Lys Thr Leu Phe Leu Leu Arg Gly
            150                 155                 160 aat cat gaa tgt aga cat cta aca gag tat ttc aca ttt aaa caa gaa       645
Asn His Glu Cys Arg His Leu Thr Glu Tyr Phe Thr Phe Lys Gln Glu
            165                 170                 175 tgt aaa ata aag tat tca gaa cga gta tat gat gcc tgt atg gat gcc       693
Cys Lys Ile Lys Tyr Ser Glu Arg Val Tyr Asp Ala Cys Met Asp Ala
            180                 185                 190 ttt gac tgc ctt ccc ctg gct gcc ctg atg aac caa cag ttc ctg tgt       741
Phe Asp Cys Leu Pro Leu Ala Ala Leu Met Asn Gln Gln Phe Leu Cys
        195                 200                 205 gtg cat ggt ggt ttg tct cca gag att aac act tta gat gat atc aga       789
Val His Gly Gly Leu Ser Pro Glu Ile Asn Thr Leu Asp Asp Ile Arg
210                 215                 220                 225 aaa tta gac cga ttc aaa gaa cca cct gca tat gga cct atg tgt gat       837
Lys Leu Asp Arg Phe Lys Glu Pro Pro Ala Tyr Gly Pro Met Cys Asp
                230                 235                 240 atc ctg tgg tca gac ccc ctg gaa gat ttt gga aat gag aag act cag       885
Ile Leu Trp Ser Asp Pro Leu Glu Asp Phe Gly Asn Glu Lys Thr Gln
                245                 250                 255 gaa cat ttc act cac aac aca gtc agg ggg tgt tca tac ttc tac agt       933
Glu His Phe Thr His Asn Thr Val Arg Gly Cys Ser Tyr Phe Tyr Ser
            260                 265                 270 tac ccg gct gta tgt gaa ttc tta cag cac aat aac ttg tta tct ata       981
Tyr Pro Ala Val Cys Glu Phe Leu Gln His Asn Asn Leu Leu Ser Ile
        275                 280                 285 ctc cga gcc cac gaa gcc caa gat gca ggg tac cgc atg tac agg aaa      1029
Leu Arg Ala His Glu Ala Gln Asp Ala Gly Tyr Arg Met Tyr Arg Lys
290                 295                 300                 305 agc caa aca aca ggc ttc cct tct cta att aca att ttt tca gca cca      1077
Ser Gln Thr Thr Gly Phe Pro Ser Leu Ile Thr Ile Phe Ser Ala Pro
                310                 315                 320 aat tac tta gat gta tac aat aac aaa gct gca gta ttg aag tat gag      1125
Asn Tyr Leu Asp Val Tyr Asn Asn Lys Ala Ala Val Leu Lys Tyr Glu
                325                 330                 335 aac aat gtt atg aat atc agg caa ttc aac tgt tct cct cat cca tac      1173
Asn Asn Val Met Asn Ile Arg Gln Phe Asn Cys Ser Pro His Pro Tyr
            340                 345                 350 tgg ctt cca aat ttc atg gat gtt ttt act tgg tcc ctt cca ttt gtt      1221
Trp Leu Pro Asn Phe Met Asp Val Phe Thr Trp Ser Leu Pro Phe Val
        355                 360                 365 ggg gaa aaa gtg act gag atg ctg gta aat gtc ctc aac atc tgc tca      1269
Gly Glu Lys Val Thr Glu Met Leu Val Asn Val Leu Asn Ile Cys Ser
370                 375                 380                 385 gat gat gaa cta ggg tca gaa gaa gat gga ttt gat ggt gca aca gct      1317
Asp Asp Glu Leu Gly Ser Glu Glu Asp Gly Phe Asp Gly Ala Thr Ala
                390                 395                 400 gca gcc cgg aaa gag gtg ata agg aac aag atc cga gca ata ggc aaa      1365
Ala Ala Arg Lys Glu Val Ile Arg Asn Lys Ile Arg Ala Ile Gly Lys
                405                 410                 415 atg gcc aga gtg ttc tca gtg ctc aga gaa gag agt gag agt gtg ctg      1413
Met Ala Arg Val Phe Ser Val Leu Arg Glu Glu Ser Glu Ser Val Leu
            420                 425                 430 acg ctg aaa ggc ttg acc cca act ggc atg ctc ccc agc gga gta ctt      1461
Thr Leu Lys Gly Leu Thr Pro Thr Gly Met Leu Pro Ser Gly Val Leu
        435                 440                 445 tct gga ggg aag caa acc ctg caa agc gct atc aaa gga ttt tca cca      1509
Ser Gly Gly Lys Gln Thr Leu Gln Ser Ala Ile Lys Gly Phe Ser Pro
450                 455                 460                 465
```

```
caa cat aag atc act agc ttc gag gaa gcc aag ggc tta gac cga att      1557
Gln His Lys Ile Thr Ser Phe Glu Glu Ala Lys Gly Leu Asp Arg Ile
            470                 475                 480 aat gag agg atg ccg cct cgc aga gat gcc atg ccc tct gac gcc aac      1605
Asn Glu Arg Met Pro Pro Arg Arg Asp Ala Met Pro Ser Asp Ala Asn
        485                 490                 495 ctt aac tcc atc aac aag gct ctc acc tca gag act aac ggc acg gac      1653
Leu Asn Ser Ile Asn Lys Ala Leu Thr Ser Glu Thr Asn Gly Thr Asp
    500                 505                 510 agc aat ggc agt aat agc agc aat att cag tga ttaactaggg taccccgggg    1706
Ser Asn Gly Ser Asn Ser Ser Asn Ile Gln
515                 520 taccaaagag gagaaattaa ct atg gga aat gag gca agt tat cct ttg gaa     1758
                        Met Gly Asn Glu Ala Ser Tyr Pro Leu Glu
                            525                 530 atg tgc tca cac ttt gat gca gat gaa att aaa agg cta gga aag aga      1806
Met Cys Ser His Phe Asp Ala Asp Glu Ile Lys Arg Leu Gly Lys Arg
535                 540                 545                 550 ttt aag aag ctc gat ttg gac aat tct ggt tct ttg agt gtg gaa gag      1854
Phe Lys Lys Leu Asp Leu Asp Asn Ser Gly Ser Leu Ser Val Glu Glu
            555                 560                 565 ttc atg tct cta cct gag tta caa cag aat ccc tta gta cag cga gta      1902
Phe Met Ser Leu Pro Glu Leu Gln Gln Asn Pro Leu Val Gln Arg Val
        570                 575                 580 ata gat ata ttc gac aca gat ggg aat gga gaa gta gac ttt aaa gag      1950
Ile Asp Ile Phe Asp Thr Asp Gly Asn Gly Glu Val Asp Phe Lys Glu
    585                 590                 595 ttc att gag gga gtc tct cag ttc agt gtc aaa gga gat aag gaa cag      1998
Phe Ile Glu Gly Val Ser Gln Phe Ser Val Lys Gly Asp Lys Glu Gln
600                 605                 610 aag ttg agg ttt gct ttc cgt atc tat gac atg gat aaa gac ggc tat      2046
Lys Leu Arg Phe Ala Phe Arg Ile Tyr Asp Met Asp Lys Asp Gly Tyr
            615                 620                 625                 630 att tcc aat ggg gaa ctc ttc cag gtg cta aag atg atg gtg ggg aac      2094
Ile Ser Asn Gly Glu Leu Phe Gln Val Leu Lys Met Met Val Gly Asn
        635                 640                 645 aat ctg aaa gat aca cag tta cag caa att gta gac aaa acc ata ata      2142
Asn Leu Lys Asp Thr Gln Leu Gln Gln Ile Val Asp Lys Thr Ile Ile
    650                 655                 660 aat gca gat aag gat ggg gat gga aga ata tcc ttt gaa gaa ttc tgt      2190
Asn Ala Asp Lys Asp Gly Asp Gly Arg Ile Ser Phe Glu Glu Phe Cys
665                 670                 675 gct gtt gta ggc ggc cta gat atc cac aaa aag atg gtg gta gat gtg      2238
Ala Val Val Gly Gly Leu Asp Ile His Lys Lys Met Val Val Asp Val
            680                 685                 690 tga ttaattagaa gcttaattag ctgagcttgg actcctgttg atagatccag           2291
taatgacctc agaactccat ctggatttgt tcagaacgct cggttgccgc cgggcgtttt    2351
ttattggtga aatccaagc tagcttggcg agattttcag gagctaagga agctaaaatg     2411
gagaaaaaaa tcactggata taccaccgtt gatatatccc aatggcatcg taagaacat     2471 tttgaggcat ttcagtcagt tgctcaatgt acctataacc agaccgttca gctggatatt    2531
acggcctttt taaagaccgt aaagaaaaat aagcacaagt tttatccggc ctttattcac    2591
attcttgccc gcctgatgaa tgctcatccg gaatttcgta tggcaatgaa agacggtgag    2651
ctggtgatat gggatagtgt tcacccttgt tacaccgttt tccatgagca aactgaaacg    2711
ttttcatcgc tctggagtga ataccacgac gatttccggc agtttctaca catatattcg    2771
caagatgtgg cgtgttacgg tgaaaacctg gcctatttcc ctaaagggtt tattgagaat    2831
```

```
atgtttttcg tctcagccaa tccctgggtg agtttcacca gttttgattt aaacgtggcc      2891
aatatggaca acttcttcgc ccccgttttc accatgggca aatattatac gcaaggcgac      2951
aaggtgctga tgccgctggc gattcaggtt catcatgccg tctgtgatgg cttccatgtc      3011
ggcagaatgc ttaatgaatt acaacagtac tgcgatgagt ggcagggcgg ggcgtaattt      3071
ttttaaggca gttattggtg cccttaaacg cctggggtaa tgactctcta gcttgaggca      3131
tcaaataaaa cgaaaggctc agtcgaaaga ctgggccttt cgttttatct gttgtttgtc      3191
ggtgaacgct ctcctgagta ggacaaatcc gccgctctag agctgcctcg cgcgtttcgg      3251
tgatgacggt gaaaacctct gacacatgca gctcccggag acggtcacag cttgtctgta      3311
agcggatgcc gggagcagac aagcccgtca gggcgcgtca gcgggtgttg gcgggtgtcg      3371 ggcgcagcc atgacccagt cacgtagcga tagcggagtg tatactggct taactatgcg      3431
gcatcagagc agattgtact gagagtgcac catatgcggt gtgaaatacc gcacagatgc      3491
gtaaggagaa ataccgcat caggcgctct tccgcttcct cgctcactga ctcgctgcgc       3551
tcggtctgtc ggctgcggcg agcggtatca gctcactcaa aggcggtaat acggttatcc      3611
acagaatcag gggataacgc aggaaagaac atgtgagcaa aaggccagca aaaggccagg      3671
aaccgtaaaa aggccgcgtt gctggcgttt ttccataggc tccgcccccc tgacgagcat      3731
cacaaaaatc gacgctcaag tcagaggtgg cgaaacccga caggactata aagataccag      3791
gcgtttcccc ctggaagctc cctcgtgcgc tctcctgttc cgaccctgcc gcttaccgga      3851
tacctgtccg cctttctccc ttcgggaagc gtggcgcttt ctcaatgctc acgctgtagg      3911
tatctcagtt cggtgtaggt cgttcgctcc aagctgggct gtgtgcacga acccccccgtt     3971 cagcccgacc gctgcgcctt atccggtaac tatcgtcttg agtccaaccc ggtaagacac      4031
gacttatcgc cactggcagc agccactggt aacaggatta gcagagcgag gtatgtaggc      4091
ggtgctacag agttcttgaa gtggtggcct aactacggct acactagaag gacagtattt      4151
ggtatctgcg ctctgctgaa gccagttacc ttcggaaaaa gagttggtag ctcttgatcc      4211
ggcaaacaaa ccaccgctgg tagcggtggt ttttttgttt gcaagcagca gattacgcgc      4271
agaaaaaaag gatctcaaga agatcctttg atcttttcta cggggtctga cgctcagtgg      4331
aacgaaaact cacgttaagg gattttggtc atgagattat caaaaaggat cttcacctag      4391
atccttttaa attaaaaatg aagttttaaa tcaatctaaa gtatatatga gtaaacttgg      4451
tctgacagtt accaatgctt aatcagtgag gcacctatct cagcgatctg tctatttcgt      4511
tcatccatag ctgcctgact ccccgtcgtg tagataacta cgatacggga gggcttacca      4571
tctggcccca gtgctgcaat gataccgcga gacccacgct caccggctcc agatttatca      4631
gcaataaacc agccagccgg aagggccgag cgcagaagtg gtcctgcaac tttatccgcc      4691
tccatccagt ctattaattg ttgccgggaa gctagagtaa gtagttcgcc agttaatagt      4751
ttgcgcaacg ttgttgccat tgctacaggc atcgtggtgt cacgctcgtc gtttggtatg      4811
gcttcattca gctccggttc ccaacgatca aggcgagtta catgatcccc catgttgtgc      4871
aaaaaagcgg ttagctcctt cggtcctccg atcgttgtca gaagtaagtt ggccgcagtg      4931
ttatcactca tggttatggc agcactgcat aattctctta ctgtcatgcc atccgtaaga      4991
tgcttttctg tgactggtga gtactcaacc aagtcattct gagaatagtg tatgcggcga      5051
ccgagttgct cttgcccggc gtcaatacgg gataataccg cgccacatag cagaacttta      5111
aaagtgctca tcattggaaa acgttcttcg ggcgaaaac tctcaaggat cttaccgctg       5171
```

```
ttgagatcca gttcgatgta acccactcgt gcacccaact gatcttcagc atctttact   5231 ttcaccagcg tttctgggtg agcaaaaaca ggaaggcaaa atgccgcaaa aaagggaata   5291
agggcgacac ggaaatgttg aatactcata ctcttcctt ttcaatatta ttgaagcatt   5351
tatcagggtt attgtctcat gagcggatac atatttgaat gtatttagaa aaataaacaa   5411
ataggggttc cgcgcacatt tccccgaaaa gtgccacctg acgtctaaga aaccattatt   5471
atcatgacat taacctataa aaataggcgt atcacgaggc cctttcgtct tcac           5525
```

<210> SEQ ID NO 21
<211> LENGTH: 523
<212> TYPE: PRT
<213> ORGANISM: Homo sapiens

<400> SEQUENCE: 21

```
Met Arg Gly Ser His His His His His His Gly Ser Met Ser Glu Pro
 1               5                  10                  15

Lys Ala Ile Asp Pro Lys Leu Ser Thr Thr Asp Arg Val Val Lys Ala
             20                  25                  30

Val Pro Phe Pro Pro Ser His Arg Leu Thr Ala Lys Glu Val Phe Asp
         35                  40                  45

Asn Asp Gly Lys Pro Arg Val Asp Ile Leu Lys Ala His Leu Met Lys
     50                  55                  60

Glu Gly Arg Leu Glu Glu Ser Val Ala Leu Arg Ile Ile Thr Glu Gly
 65                  70                  75                  80

Ala Ser Ile Leu Arg Gln Glu Lys Asn Leu Leu Asp Ile Asp Ala Pro
                 85                  90                  95

Val Thr Val Cys Gly Asp Ile His Gly Gln Phe Phe Asp Leu Met Lys
            100                 105                 110

Leu Phe Glu Val Gly Gly Ser Pro Ala Asn Thr Arg Tyr Leu Phe Leu
        115                 120                 125

Gly Asp Tyr Val Asp Arg Gly Tyr Phe Ser Ile Glu Cys Val Leu Tyr
    130                 135                 140

Leu Trp Ala Leu Lys Ile Leu Tyr Pro Lys Thr Leu Phe Leu Leu Arg
145                 150                 155                 160

Gly Asn His Glu Cys Arg His Leu Thr Glu Tyr Phe Thr Phe Lys Gln
                165                 170                 175

Glu Cys Lys Ile Lys Tyr Ser Glu Arg Val Tyr Asp Ala Cys Met Asp
            180                 185                 190

Ala Phe Asp Cys Leu Pro Leu Ala Ala Leu Met Asn Gln Gln Phe Leu
        195                 200                 205

Cys Val His Gly Gly Leu Ser Pro Glu Ile Asn Thr Leu Asp Asp Ile
    210                 215                 220

Arg Lys Leu Asp Arg Phe Lys Glu Pro Pro Ala Tyr Gly Pro Met Cys
225                 230                 235                 240

Asp Ile Leu Trp Ser Asp Pro Leu Glu Asp Phe Gly Asn Glu Lys Thr
                245                 250                 255

Gln Glu His Phe Thr His Asn Thr Val Arg Gly Cys Ser Tyr Phe Tyr
            260                 265                 270

Ser Tyr Pro Ala Val Cys Glu Phe Leu Gln His Asn Asn Leu Leu Ser
        275                 280                 285

Ile Leu Arg Ala His Glu Ala Gln Asp Ala Gly Tyr Arg Met Tyr Arg
    290                 295                 300

Lys Ser Gln Thr Thr Gly Phe Pro Ser Leu Ile Thr Ile Phe Ser Ala
305                 310                 315                 320
```

```
Pro Asn Tyr Leu Asp Val Tyr Asn Asn Lys Ala Ala Val Leu Lys Tyr
            325                 330                 335

Glu Asn Asn Val Met Asn Ile Arg Gln Phe Asn Cys Ser Pro His Pro
            340                 345                 350

Tyr Trp Leu Pro Asn Phe Met Asp Val Phe Thr Trp Ser Leu Pro Phe
            355                 360                 365

Val Gly Glu Lys Val Thr Glu Met Leu Val Asn Val Leu Asn Ile Cys
    370                 375                 380

Ser Asp Asp Glu Leu Gly Ser Glu Asp Gly Phe Asp Gly Ala Thr
385                 390                 395                 400

Ala Ala Ala Arg Lys Glu Val Ile Arg Asn Lys Ile Arg Ala Ile Gly
                405                 410                 415

Lys Met Ala Arg Val Phe Ser Val Leu Arg Glu Glu Ser Glu Ser Val
                420                 425                 430

Leu Thr Leu Lys Gly Leu Thr Pro Thr Gly Met Leu Pro Ser Gly Val
        435                 440                 445

Leu Ser Gly Gly Lys Gln Thr Leu Gln Ser Ala Ile Lys Gly Phe Ser
    450                 455                 460

Pro Gln His Lys Ile Thr Ser Phe Glu Glu Ala Lys Gly Leu Asp Arg
465                 470                 475                 480

Ile Asn Glu Arg Met Pro Pro Arg Arg Asp Ala Met Pro Ser Asp Ala
                485                 490                 495

Asn Leu Asn Ser Ile Asn Lys Ala Leu Thr Ser Glu Thr Asn Gly Thr
                500                 505                 510

Asp Ser Asn Gly Ser Asn Ser Ser Asn Ile Gln
        515                 520

<210> SEQ ID NO 22
<211> LENGTH: 170
<212> TYPE: PRT
<213> ORGANISM: Homo sapiens

<400> SEQUENCE: 22

Met Gly Asn Glu Ala Ser Tyr Pro Leu Glu Met Cys Ser His Phe Asp
  1               5                  10                  15

Ala Asp Glu Ile Lys Arg Leu Gly Lys Arg Phe Lys Lys Leu Asp Leu
                20                  25                  30

Asp Asn Ser Gly Ser Leu Ser Val Glu Glu Phe Met Ser Leu Pro Glu
            35                  40                  45

Leu Gln Gln Asn Pro Leu Val Gln Arg Val Ile Asp Ile Phe Asp Thr
        50                  55                  60

Asp Gly Asn Gly Glu Val Asp Phe Lys Glu Phe Ile Glu Gly Val Ser
 65                  70                  75                  80

Gln Phe Ser Val Lys Gly Asp Lys Glu Gln Lys Leu Arg Phe Ala Phe
                85                  90                  95

Arg Ile Tyr Asp Met Asp Lys Asp Gly Tyr Ile Ser Asn Gly Glu Leu
                100                 105                 110

Phe Gln Val Leu Lys Met Met Val Gly Asn Asn Leu Lys Asp Thr Gln
            115                 120                 125

Leu Gln Gln Ile Val Asp Lys Thr Ile Ile Asn Ala Asp Lys Asp Gly
        130                 135                 140

Asp Gly Arg Ile Ser Phe Glu Glu Phe Cys Ala Val Val Gly Gly Leu
145                 150                 155                 160

Asp Ile His Lys Lys Met Val Val Asp Val
```

-continued

```
                           165                    170

<210> SEQ ID NO 23
<211> LENGTH: 5557
<212> TYPE: DNA
<213> ORGANISM: Homo sapiens
<220> FEATURE:
<221> NAME/KEY: CDS
<222> LOCATION: (115)..(1722)
<223> OTHER INFORMATION: histidine tagged calcineurin A beta1
<221> NAME/KEY: misc_feature
<222> LOCATION: (1723)..(1760)
<223> OTHER INFORMATION: ribosomal binding site, multiple cloning site 2
<221> NAME/KEY: CDS
<222> LOCATION: (1761)..(2273)
<223> OTHER INFORMATION: calcineurin B
<221> NAME/KEY: misc_feature
<222> LOCATION: 553
<223> OTHER INFORMATION: Xaa = any amino acid
<221> NAME/KEY: misc_feature
<222> LOCATION: 566
<223> OTHER INFORMATION: Xaa = any amino acid
<221> NAME/KEY: misc_feature
<222> LOCATION: 582
<223> OTHER INFORMATION: Xaa = any amino acid
<221> NAME/KEY: misc_feature
<222> LOCATION: 589
<223> OTHER INFORMATION: Xaa = any amino acid
<221> NAME/KEY: misc_feature
<222> LOCATION: 614
<223> OTHER INFORMATION: Xaa = any amino acid
<221> NAME/KEY: misc_feature
<222> LOCATION: 651
<223> OTHER INFORMATION: Xaa = any amino acid
<221> NAME/KEY: misc_feature
<222> LOCATION: 652
<223> OTHER INFORMATION: Xaa = any amino acid
<221> NAME/KEY: misc_feature
<222> LOCATION: 680
<223> OTHER INFORMATION: Xaa = any amino acid
<221> NAME/KEY: misc_feature
<222> LOCATION: 694
<223> OTHER INFORMATION: Xaa = any amino acid

<400> SEQUENCE: 23
ctcgagaaat cataaaaaat ttatttgctt tgtgagcgga taacaattat aatagattca        60
attgtgagcg gataacaatt tcacacagaa ttcattaaag aggagaaatt aact atg        117
                                                              Met
                                                                1 aga gga tcg cat cac cat cac cat cac gga tcc gcc gcc ccg gag ccg        165
Arg Gly Ser His His His His His His Gly Ser Ala Ala Pro Glu Pro
            5                  10                  15 gcc cgg gct gca ccg ccc cca ccc ccg ccc ccg ccg ccc cct ccc ggg        213
Ala Arg Ala Ala Pro Pro Pro Pro Pro Pro Pro Pro Pro Pro Pro Gly
         20                  25                  30 gct gac cgc gtc gtc aaa gct gtc cct ttc ccc cca aca cat cgc ttg        261
Ala Asp Arg Val Val Lys Ala Val Pro Phe Pro Pro Thr His Arg Leu
     35                  40                  45 aca tct gaa gaa gta ttt gat ttg gat ggg ata ccc agg gtt gat gtt        309
Thr Ser Glu Glu Val Phe Asp Leu Asp Gly Ile Pro Arg Val Asp Val
 50                  55                  60                  65 ctg aag aac cac ttg gtg aaa gaa ggt cga gta gat gaa gaa att gcg        357
Leu Lys Asn His Leu Val Lys Glu Gly Arg Val Asp Glu Glu Ile Ala
                 70                  75                  80 ctt aga att atc aat gag ggt gct gcc atc ctt cgg aga gag aaa acc        405
Leu Arg Ile Ile Asn Glu Gly Ala Ala Ile Leu Arg Arg Glu Lys Thr
             85                  90                  95 atg ata gaa gta gaa gct cca atc aca gtg tgt ggt gac atc cat ggc        453
Met Ile Glu Val Glu Ala Pro Ile Thr Val Cys Gly Asp Ile His Gly
        100                 105                 110
```

-continued

```
            100                 105                 110
caa ttt ttt gat ctg atg aaa ctt ttt gaa gta gga gga tca cct gct       501
Gln Phe Phe Asp Leu Met Lys Leu Phe Glu Val Gly Gly Ser Pro Ala
    115                 120                 125 aat aca cga tac ctt ttt ctt ggc gat tat gtg gac aga ggt tat ttt       549
Asn Thr Arg Tyr Leu Phe Leu Gly Asp Tyr Val Asp Arg Gly Tyr Phe
130                 135                 140                 145 agt ata gag tgt gtc tta tat tta tgg gtt ctg aag att cta tac cca       597
Ser Ile Glu Cys Val Leu Tyr Leu Trp Val Leu Lys Ile Leu Tyr Pro
                150                 155                 160 agc aca tta ttt ctt ctg aga ggc aac cat gaa tgc aga cac ctt act       645
Ser Thr Leu Phe Leu Leu Arg Gly Asn His Glu Cys Arg His Leu Thr
            165                 170                 175 gaa tat ttt acc ttt aag cag gaa tgt aaa att aag tat tcg gaa aga       693
Glu Tyr Phe Thr Phe Lys Gln Glu Cys Lys Ile Lys Tyr Ser Glu Arg
        180                 185                 190 gtc tat gaa gct tgt atg gaa gct ttt gat agt ttg cct ctt gct gca       741
Val Tyr Glu Ala Cys Met Glu Ala Phe Asp Ser Leu Pro Leu Ala Ala
    195                 200                 205 ctt tta aac caa cag ttt ctt tgt gtt cat ggt gga ctt tca cca gaa       789
Leu Leu Asn Gln Gln Phe Leu Cys Val His Gly Gly Leu Ser Pro Glu
210                 215                 220                 225 ata cac aca ctg gat gat att agg aga tta gat aga ttc aaa gag cca       837
Ile His Thr Leu Asp Asp Ile Arg Arg Leu Asp Arg Phe Lys Glu Pro
                230                 235                 240 cct gca ttt gga cca atg tgt gac ttg tta tgg tcc gat cct tct gaa       885
Pro Ala Phe Gly Pro Met Cys Asp Leu Leu Trp Ser Asp Pro Ser Glu
            245                 250                 255 gat ttt gga aat gaa aaa tca cag gaa cat ttt agt cac aat aca gtt       933
Asp Phe Gly Asn Glu Lys Ser Gln Glu His Phe Ser His Asn Thr Val
        260                 265                 270 cga gga tgt tct tat ttt tat aac tat cca gca gtg tgt gaa ttt ttg       981
Arg Gly Cys Ser Tyr Phe Tyr Asn Tyr Pro Ala Val Cys Glu Phe Leu
    275                 280                 285 caa aac aat aat ttg tta tcg att att aga gct cat gaa gct caa gat      1029
Gln Asn Asn Asn Leu Leu Ser Ile Ile Arg Ala His Glu Ala Gln Asp
290                 295                 300                 305 gca ggc tat aga atg tac aga aaa agt caa act aca ggg ttc cct tca      1077
Ala Gly Tyr Arg Met Tyr Arg Lys Ser Gln Thr Thr Gly Phe Pro Ser
                310                 315                 320 tta ata aca att ttt tcg gca cct aat tac tta gat gtc tac aat aat      1125
Leu Ile Thr Ile Phe Ser Ala Pro Asn Tyr Leu Asp Val Tyr Asn Asn
            325                 330                 335 aaa gct gct gta tta aag tat gaa aat aat gtg atg aat att cga cag      1173
Lys Ala Ala Val Leu Lys Tyr Glu Asn Asn Val Met Asn Ile Arg Gln
        340                 345                 350 ttt aac tgt tct cca cat cct tac tgg ttg cct aat ttt atg gat gtc      1221
Phe Asn Cys Ser Pro His Pro Tyr Trp Leu Pro Asn Phe Met Asp Val
    355                 360                 365 ttc acg tgg tct tta ccg ttt gtt gga gaa aaa gtg aca gaa atg ttg      1269
Phe Thr Trp Ser Leu Pro Phe Val Gly Glu Lys Val Thr Glu Met Leu
370                 375                 380                 385 gta aat gtt ctg agt att tgc tct gat gat gaa cta atg act gaa ggt      1317
Val Asn Val Leu Ser Ile Cys Ser Asp Asp Glu Leu Met Thr Glu Gly
                390                 395                 400 gaa gac cag ttt gat ggt tca gct gca gcc cgg aaa gaa atc ata aga      1365
Glu Asp Gln Phe Asp Gly Ser Ala Ala Ala Arg Lys Glu Ile Ile Arg
            405                 410                 415 aac aaa att cga gca att ggc aag atg gca aga gtc ttc tct gtt ctc      1413
```

```
                Asn Lys Ile Arg Ala Ile Gly Lys Met Ala Arg Val Phe Ser Val Leu
                    420                 425                 430 agg gag gag agt gaa agt gtg ctg aca ctc aag ggc ctg act ccc aca        1461
Arg Glu Glu Ser Glu Ser Val Leu Thr Leu Lys Gly Leu Thr Pro Thr
    435                 440                 445 ggg atg ttg cct agt gga gtg tta gct gga gga cgg cag acc ctg caa        1509
Gly Met Leu Pro Ser Gly Val Leu Ala Gly Gly Arg Gln Thr Leu Gln
450                 455                 460                 465 agt gcc aca gtt gag gct att gag gct gaa aaa gca ata cga gga ttc        1557
Ser Ala Thr Val Glu Ala Ile Glu Ala Glu Lys Ala Ile Arg Gly Phe
                470                 475                 480 tct cca cca cat aga atc tgc agt ttt gaa gag gca aag ggt ttg gat        1605
Ser Pro Pro His Arg Ile Cys Ser Phe Glu Glu Ala Lys Gly Leu Asp
            485                 490                 495 agg atc aat gag aga atg cca cct cgg aaa gat gct gta cag caa gat        1653
Arg Ile Asn Glu Arg Met Pro Pro Arg Lys Asp Ala Val Gln Gln Asp
        500                 505                 510 ggt ttc aat tct ctg aac acc gca cat gcc act gag aac cac ggg acg        1701
Gly Phe Asn Ser Leu Asn Thr Ala His Ala Thr Glu Asn His Gly Thr
    515                 520                 525 ggc aac cat act gcc cag tga ttaactaggg taccccgggg aaagaggaga          1752
Gly Asn His Thr Ala Gln
530             535 aattaact atg gga aat gag gca agt tat cct ttg gaa atg tgc tca cac       1802
         Met Gly Asn Glu Ala Ser Tyr Pro Leu Glu Met Cys Ser His
                         540                 545                 550 ttt gat gcr gat gaa att aaa agg cta gga aag aga ttt aag aag cty        1850
Phe Asp Xaa Asp Glu Ile Lys Arg Leu Gly Lys Arg Phe Lys Lys Xaa
                555                 560                 565 gat ttg gac aat tct ggt tct ttg agt gtg gaa gag ttc atg tct ctr        1898
Asp Leu Asp Asn Ser Gly Ser Leu Ser Val Glu Glu Phe Met Ser Xaa
            570                 575                 580 cct gag tta caa cag aat ccy tta gta cag cga gta ata gat ata ttc        1946
Pro Glu Leu Gln Gln Asn Xaa Leu Val Gln Arg Val Ile Asp Ile Phe
        585                 590                 595 gac aca gat ggg aat gga gaa gta gac ttt aaa gar ttc att gag ggm        1994
Asp Thr Asp Gly Asn Gly Glu Val Asp Phe Lys Glu Phe Ile Glu Xaa
    600                 605                 610 gtc tct cag ttc agt gtc aaa gga gat aag gar cag aar ttg agg ttt        2042
Val Ser Gln Phe Ser Val Lys Gly Asp Lys Glu Gln Lys Leu Arg Phe
615                 620                 625                 630 gct ttc cgt atc tat gac atg gat aaa gay ggc tat att tcc aat ggg        2090
Ala Phe Arg Ile Tyr Asp Met Asp Lys Asp Gly Tyr Ile Ser Asn Gly
                635                 640                 645 gaa ctc ttc cag gtr ytr aag atg atg gtg ggg aac aat ctg aaa gat        2138
Glu Leu Phe Gln Xaa Xaa Lys Met Met Val Gly Asn Asn Leu Lys Asp
            650                 655                 660 aca cag tta cag caa att gta gac aaa acc ata ata aat gca gat aag        2186
Thr Gln Leu Gln Gln Ile Val Asp Lys Thr Ile Ile Asn Ala Asp Lys
        665                 670                 675 gat ggr gat gga aga ata tcc ttt gaa gaa ttc tgt gct gtt gta ggy        2234
Asp Xaa Asp Gly Arg Ile Ser Phe Glu Glu Phe Cys Ala Val Val Xaa
    680                 685                 690 ggc cta gat atc cac aaa aag atg gtg gta gat gtg tga ttaattagaa        2283
Gly Leu Asp Ile His Lys Lys Met Val Val Asp Val
695                 700                 705 gcttaattag ctgagcttgg actcctgttg atagatccag taatgacctc agaactccat     2343
ctggatttgt tcagaacgct cggttgccgc cgggcgtttt ttattggtga gaatccaagc     2403
```

```
tagcttggcg agattttcag gagctaagga agctaaaatg gagaaaaaaa tcactggata    2463
taccaccgtt gatatatccc aatggcatcg taaagaacat tttgaggcat ttcagtcagt    2523
tgctcaatgt acctataacc agaccgttca gctggatatt acggccttt  taaagaccgt    2583
aaagaaaaat aagcacaagt tttatccggc ctttattcac attcttgccc gcctgatgaa    2643
tgctcatccg gaatttcgta tggcaatgaa agacggtgag ctggtgatat gggatagtgt    2703
tcacccttgt tacaccgttt tccatgagca aactgaaacg ttttcatcgc tctggagtga    2763
ataccacgac gatttccggc agtttctaca catatattcg caagatgtgg cgtgttacgg    2823
tgaaaacctg gcctatttcc ctaaagggtt tattgagaat atgttttcg  tctcagccaa    2883
tccctgggtg agtttcacca gttttgattt aaacgtggcc aatatggaca acttcttcgc    2943
ccccgttttc accatgggca aatattatac gcaaggcgac aaggtgctga tgccgctggc    3003
gattcaggtt catcatgccg tctgtgatgg cttccatgtc ggcagaatgc ttaatgaatt    3063
acaacagtac tgcgatgagt ggcagggcgg ggcgtaattt ttttaaggca gttattggtg    3123
cccttaaacg cctggggtaa tgactctcta gcttgaggca tcaaataaaa cgaaaggctc    3183
agtcgaaaga ctgggccttt cgttttatct gttgtttgtc ggtgaacgct ctcctgagta    3243
ggacaaatcc gccgctctag agctgcctcg cgcgtttcgg tgatgacggt gaaaacctct    3303
gacacatgca gctcccggag acggtcacag cttgtctgta gcggatgcc  gggagcagac    3363
aagcccgtca gggcgcgtca gcgggtgttg gcgggtgtcg gggcgcagcc atgacccagt    3423
cacgtagcga tagcggagtg tatactggct taactatgcg gcatcagagc agattgtact    3483
gagagtgcac catatgcggt gtgaaatacc gcacagatgc gtaaggagaa ataccgcat   3543
caggcgctct tccgcttcct cgctcactga ctcgctgcgc tcggtctgtc ggctgcggcg    3603
agcggtatca gctcactcaa aggcggtaat acggttatcc acagaatcag gggataacgc    3663
aggaaagaac atgtgagcaa aaggccagca aaaggccagg aaccgtaaaa aggccgcgtt    3723
gctggcgttt ttccataggc tccgccccc  tgacgagcat cacaaaaatc gacgctcaag    3783
tcagaggtgg cgaaacccga caggactata aagataccag gcgtttcccc ctggaagctc    3843
cctcgtgcgc tctcctgttc cgaccctgcc gcttaccgga tacctgtccg cctttctccc    3903
ttcgggaagc gtggcgcttt ctcaatgctc acgctgtagg tatctcagtt cggtgtaggt    3963
cgttcgctcc aagctgggct gtgtgcacga accccccgtt cagcccgacc gctgcgcctt    4023
atccggtaac tatcgtcttg agtccaaccc ggtaagacac gacttatcgc cactggcagc    4083
agccactggt aacaggatta gcagagcgag gtatgtaggc ggtgctacag agttcttgaa    4143
gtggtggcct aactacggct acactagaag gacagtattt ggtatctgcg ctctgctgaa    4203
gccagttacc ttcggaaaaa gagttggtag ctcttgatcc ggcaaacaaa ccaccgctgg    4263
tagcggtggt ttttttgttt gcaagcagca gattacgcgc agaaaaaaag gatctcaaga    4323
agatcctttg atcttttcta cggggtctga cgctcagtgg aacgaaaact cacgttaagg    4383
gattttggtc atgagattat caaaaaggat cttcacctag atccttttaa attaaaaatg    4443
aagttttaaa tcaatctaaa gtatatatga gtaaacttgg tctgacagtt accaatgctt    4503
aatcagtgag gcacctatct cagcgatctg tctatttcgt tcatccatag ctgcctgact    4563
ccccgtcgtg tagataacta cgatacggga gggcttacca tctggcccca gtgctgcaat    4623
gataccgcga gacccacgct caccggctcc agatttatca gcaataaacc agccagccgg    4683
aagggccgag cgcagaagtg gtcctgcaac tttatccgcc tccatccagt ctattaattg    4743
ttgccgggaa gctagagtaa gtagttcgcc agttaatagt ttgcgcaacg ttgttgccat    4803
```

-continued

```
tgctacaggc atcgtggtgt cacgctcgtc gtttggtatg gcttcattca gctccggttc    4863
ccaacgatca aggcgagtta catgatcccc catgttgtgc aaaaaagcgg ttagctcctt    4923
cggtcctccg atcgttgtca gaagtaagtt ggccgcagtg ttatcactca tggttatggc    4983
agcactgcat aattctctta ctgtcatgcc atccgtaaga tgcttttctg tgactggtga    5043
gtactcaacc aagtcattct gagaatagtg tatgcggcga ccgagttgct cttgcccggc    5103
gtcaatacgg gataataccg cgccacatag cagaacttta aaagtgctca tcattggaaa    5163
acgttcttcg gggcgaaaac tctcaaggat cttaccgctg ttgagatcca gttcgatgta    5223
acccactcgt gcacccaact gatcttcagc atctttact ttcaccagcg tttctgggtg    5283
agcaaaaaca ggaaggcaaa atgccgcaaa aaagggaata agggcgacac ggaaatgttg    5343
aatactcata ctcttccttt ttcaatatta ttgaagcatt tatcagggtt attgtctcat    5403
gagcggatac atatttgaat gtatttagaa aaataaacaa ataggggttc cgcgcacatt    5463
tccccgaaaa gtgccacctg acgtctaaga aaccattatt atcatgacat taacctataa    5523
aaataggcgt atcacgaggc cctttcgtct tcac                                5557
```

<210> SEQ ID NO 24
<211> LENGTH: 535
<212> TYPE: PRT
<213> ORGANISM: Homo sapiens

<400> SEQUENCE: 24

```
Met Arg Gly Ser His His His His His Gly Ser Ala Ala Pro Glu
  1               5                  10                  15

Pro Ala Arg Ala Ala Pro Pro Pro Pro Pro Pro Pro Pro Pro Pro
                 20                  25                  30

Gly Ala Asp Arg Val Val Lys Ala Val Pro Phe Pro Pro Thr His Arg
                 35                  40                  45

Leu Thr Ser Glu Glu Val Phe Asp Leu Asp Gly Ile Pro Arg Val Asp
 50                  55                  60

Val Leu Lys Asn His Leu Val Lys Glu Gly Arg Val Asp Glu Glu Ile
 65                  70                  75                  80

Ala Leu Arg Ile Ile Asn Glu Gly Ala Ala Ile Leu Arg Arg Glu Lys
                 85                  90                  95

Thr Met Ile Glu Val Glu Ala Pro Ile Thr Val Cys Gly Asp Ile His
                100                 105                 110

Gly Gln Phe Phe Asp Leu Met Lys Leu Phe Glu Val Gly Gly Ser Pro
                115                 120                 125

Ala Asn Thr Arg Tyr Leu Phe Leu Gly Asp Tyr Val Asp Arg Gly Tyr
                130                 135                 140

Phe Ser Ile Glu Cys Val Leu Tyr Leu Trp Val Leu Lys Ile Leu Tyr
145                 150                 155                 160

Pro Ser Thr Leu Phe Leu Leu Arg Gly Asn His Glu Cys Arg His Leu
                165                 170                 175

Thr Glu Tyr Phe Thr Phe Lys Gln Glu Cys Lys Ile Lys Tyr Ser Glu
                180                 185                 190

Arg Val Tyr Glu Ala Cys Met Glu Ala Phe Asp Ser Leu Pro Leu Ala
                195                 200                 205

Ala Leu Leu Asn Gln Gln Phe Leu Cys Val His Gly Gly Leu Ser Pro
                210                 215                 220

Glu Ile His Thr Leu Asp Asp Ile Arg Arg Leu Asp Arg Phe Lys Glu
225                 230                 235                 240
```

```
Pro Pro Ala Phe Gly Pro Met Cys Asp Leu Leu Trp Ser Asp Pro Ser
                245                 250                 255

Glu Asp Phe Gly Asn Glu Lys Ser Gln Glu His Phe Ser His Asn Thr
            260                 265                 270

Val Arg Gly Cys Ser Tyr Phe Tyr Asn Tyr Pro Ala Val Cys Glu Phe
            275                 280                 285

Leu Gln Asn Asn Asn Leu Leu Ser Ile Ile Arg Ala His Glu Ala Gln
            290                 295                 300

Asp Ala Gly Tyr Arg Met Tyr Arg Lys Ser Gln Thr Thr Gly Phe Pro
305                 310                 315                 320

Ser Leu Ile Thr Ile Phe Ser Ala Pro Asn Tyr Leu Asp Val Tyr Asn
                325                 330                 335

Asn Lys Ala Ala Val Leu Lys Tyr Glu Asn Asn Val Met Asn Ile Arg
            340                 345                 350

Gln Phe Asn Cys Ser Pro His Pro Tyr Trp Leu Pro Asn Phe Met Asp
            355                 360                 365

Val Phe Thr Trp Ser Leu Pro Phe Val Gly Glu Lys Val Thr Glu Met
370                 375                 380

Leu Val Asn Val Leu Ser Ile Cys Ser Asp Asp Glu Leu Met Thr Glu
385                 390                 395                 400

Gly Glu Asp Gln Phe Asp Gly Ser Ala Ala Arg Lys Glu Ile Ile
            405                 410                 415

Arg Asn Lys Ile Arg Ala Ile Gly Lys Met Ala Arg Val Phe Ser Val
            420                 425                 430

Leu Arg Glu Glu Ser Glu Ser Val Leu Thr Leu Lys Gly Leu Thr Pro
            435                 440                 445

Thr Gly Met Leu Pro Ser Gly Val Leu Ala Gly Gly Arg Gln Thr Leu
            450                 455                 460

Gln Ser Ala Thr Val Glu Ala Ile Glu Ala Glu Lys Ala Ile Arg Gly
465                 470                 475                 480

Phe Ser Pro Pro His Arg Ile Cys Ser Phe Glu Glu Ala Lys Gly Leu
                485                 490                 495

Asp Arg Ile Asn Glu Arg Met Pro Pro Arg Lys Asp Ala Val Gln Gln
            500                 505                 510

Asp Gly Phe Asn Ser Leu Asn Thr Ala His Ala Thr Glu Asn His Gly
            515                 520                 525

Thr Gly Asn His Thr Ala Gln
            530                 535

<210> SEQ ID NO 25
<211> LENGTH: 170
<212> TYPE: PRT
<213> ORGANISM: Homo sapiens
<220> FEATURE:
<221> NAME/KEY: misc_feature
<222> LOCATION: 17
<223> OTHER INFORMATION: Xaa = any amino acid
<221> NAME/KEY: misc_feature
<222> LOCATION: 30
<223> OTHER INFORMATION: Xaa = any amino acid
<221> NAME/KEY: misc_feature
<222> LOCATION: 46
<223> OTHER INFORMATION: Xaa = any amino acid
<221> NAME/KEY: misc_feature
<222> LOCATION: 53
<223> OTHER INFORMATION: Xaa = any amino acid
<221> NAME/KEY: misc_feature
<222> LOCATION: 78
<223> OTHER INFORMATION: Xaa = any amino acid
```

-continued

```
<221> NAME/KEY: misc_feature
<222> LOCATION: 115
<223> OTHER INFORMATION: Xaa = any amino acid
<221> NAME/KEY: misc_feature
<222> LOCATION: 116
<223> OTHER INFORMATION: Xaa = any amino acid
<221> NAME/KEY: misc_feature
<222> LOCATION: 144
<223> OTHER INFORMATION: Xaa = any amino acid
<221> NAME/KEY: misc_feature
<222> LOCATION: 158
<223> OTHER INFORMATION: Xaa = any amino acid

<400> SEQUENCE: 25

Met Gly Asn Glu Ala Ser Tyr Pro Leu Glu Met Cys Ser His Phe Asp
 1               5                  10                  15

Xaa Asp Glu Ile Lys Arg Leu Gly Lys Arg Phe Lys Lys Xaa Asp Leu
            20                  25                  30

Asp Asn Ser Gly Ser Leu Ser Val Glu Glu Phe Met Ser Xaa Pro Glu
        35                  40                  45

Leu Gln Gln Asn Xaa Leu Val Gln Arg Val Ile Asp Ile Phe Asp Thr
    50                  55                  60

Asp Gly Asn Gly Glu Val Asp Phe Lys Glu Phe Ile Glu Xaa Val Ser
65                  70                  75                  80

Gln Phe Ser Val Lys Gly Asp Lys Glu Gln Lys Leu Arg Phe Ala Phe
                85                  90                  95

Arg Ile Tyr Asp Met Asp Lys Asp Gly Tyr Ile Ser Asn Gly Glu Leu
            100                 105                 110

Phe Gln Xaa Xaa Lys Met Met Val Gly Asn Asn Leu Lys Asp Thr Gln
        115                 120                 125

Leu Gln Gln Ile Val Asp Lys Thr Ile Ile Asn Ala Asp Lys Asp Xaa
    130                 135                 140

Asp Gly Arg Ile Ser Phe Glu Glu Phe Cys Ala Val Val Xaa Gly Leu
145                 150                 155                 160

Asp Ile His Lys Lys Met Val Val Asp Val
                165                 170

<210> SEQ ID NO 26
<211> LENGTH: 5611
<212> TYPE: DNA
<213> ORGANISM: Homo sapiens
<220> FEATURE:
<221> NAME/KEY: CDS
<222> LOCATION: (115)..(1776)
<223> OTHER INFORMATION: histidine tagged calcineurin A beta2
<221> NAME/KEY: misc_feature
<222> LOCATION: (1777)..(1814)
<223> OTHER INFORMATION: ribosomal binding site, multiple cloning site 2
<221> NAME/KEY: CDS
<222> LOCATION: (1815)..(2327)
<223> OTHER INFORMATION: calcineurin B
<221> NAME/KEY: misc_feature
<222> LOCATION: 571
<223> OTHER INFORMATION: Xaa = any amino acid
<221> NAME/KEY: misc_feature
<222> LOCATION: 584
<223> OTHER INFORMATION: Xaa = any amino acid
<221> NAME/KEY: misc_feature
<222> LOCATION: 600
<223> OTHER INFORMATION: Xaa = any amino acid
<221> NAME/KEY: misc_feature
<222> LOCATION: 607
<223> OTHER INFORMATION: Xaa = any amino acid
<221> NAME/KEY: misc_feature
<222> LOCATION: 632
<223> OTHER INFORMATION: Xaa = any amino acid
<221> NAME/KEY: misc_feature
```

-continued

```
<222> LOCATION: 669
<223> OTHER INFORMATION: Xaa = any amino acid
<221> NAME/KEY: misc_feature
<222> LOCATION: 670
<223> OTHER INFORMATION: Xaa = any amino acid
<221> NAME/KEY: misc_feature
<222> LOCATION: 698
<223> OTHER INFORMATION: Xaa = any amino acid
<221> NAME/KEY: misc_feature
<222> LOCATION: 712
<223> OTHER INFORMATION: Xaa = any amino acid

<400> SEQUENCE: 26
ctcgagaaat cataaaaaat ttatttgctt tgtgagcgga taacaattat aatagattca     60
attgtgagcg gataacaatt tcacacagaa ttcattaaag aggagaaatt aact atg      117
                                                              Met
                                                                1 aga gga tcg cat cac cat cac cat cac gga tcc gcc gcc ccg gag ccg      165
Arg Gly Ser His His His His His His Gly Ser Ala Ala Pro Glu Pro
            5                  10                  15 gcc cgg gct gca ccc cca ccc ccg ccc ccg ccg ccc cct ccc ggg          213
Ala Arg Ala Ala Pro Pro Pro Pro Pro Pro Pro Pro Pro Pro Gly
         20                  25                  30 gct gac cgc gtc gtc aaa gct gtc cct ttc ccc cca aca cat cgc ttg      261
Ala Asp Arg Val Val Lys Ala Val Pro Phe Pro Pro Thr His Arg Leu
     35                  40                  45 aca tct gaa gaa gta ttt gat ttg gat ggg ata ccc agg gtt gat gtt      309
Thr Ser Glu Glu Val Phe Asp Leu Asp Gly Ile Pro Arg Val Asp Val
 50                  55                  60                  65 ctg aag aac cac ttg gtg aaa gaa ggt cga gta gat gaa gaa att gcg      357
Leu Lys Asn His Leu Val Lys Glu Gly Arg Val Asp Glu Glu Ile Ala
                 70                  75                  80 ctt aga att atc aat gag ggt gct gcc atc ctt cgg aga gag aaa acc      405
Leu Arg Ile Ile Asn Glu Gly Ala Ala Ile Leu Arg Arg Glu Lys Thr
             85                  90                  95 atg ata gaa gta gaa gct cca atc aca gtg tgt ggt gac atc cat ggc      453
Met Ile Glu Val Glu Ala Pro Ile Thr Val Cys Gly Asp Ile His Gly
        100                 105                 110 caa ttt ttt gat ctg atg aaa ctt ttt gaa gta gga gga tca cct gct      501
Gln Phe Phe Asp Leu Met Lys Leu Phe Glu Val Gly Gly Ser Pro Ala
    115                 120                 125 aat aca cga tac ctt ttt ctt ggc gat tat gtg gac aga ggt tat ttt      549
Asn Thr Arg Tyr Leu Phe Leu Gly Asp Tyr Val Asp Arg Gly Tyr Phe
130                 135                 140                 145 agt ata gag cat gtt cta ggc act gaa gac ata tcg att aat cct cac      597
Ser Ile Glu His Val Leu Gly Thr Glu Asp Ile Ser Ile Asn Pro His
                150                 155                 160 aat aat att aat gag tgt gtc tta tat tta tgg gtt ctg aag att cta      645
Asn Asn Ile Asn Glu Cys Val Leu Tyr Leu Trp Val Leu Lys Ile Leu
            165                 170                 175 tac cca agc aca tta ttt ctt ctg aga ggc aac cat gaa tgc aga cac      693
Tyr Pro Ser Thr Leu Phe Leu Leu Arg Gly Asn His Glu Cys Arg His
        180                 185                 190 ctt act gaa tat ttt acc ttt aag cag gaa tgt aaa att aag tat tcg      741
Leu Thr Glu Tyr Phe Thr Phe Lys Gln Glu Cys Lys Ile Lys Tyr Ser
    195                 200                 205 gaa aga gtc tat gaa gct tgt atg gaa gct ttt gat agt ttg cct ctt      789
Glu Arg Val Tyr Glu Ala Cys Met Glu Ala Phe Asp Ser Leu Pro Leu
210                 215                 220                 225 gct gca ctt tta aac caa cag ttt ctt tgt gtt cat ggt gga ctt tca      837
Ala Ala Leu Leu Asn Gln Gln Phe Leu Cys Val His Gly Gly Leu Ser
                230                 235                 240
```

```
cca gaa ata cac aca ctg gat gat att agg aga tta gat aga ttc aaa      885
Pro Glu Ile His Thr Leu Asp Asp Ile Arg Arg Leu Asp Arg Phe Lys
            245                 250                 255 gag cca cct gca ttt gga cca atg tgt gac ttg tta tgg tcc gat cct      933
Glu Pro Pro Ala Phe Gly Pro Met Cys Asp Leu Leu Trp Ser Asp Pro
    260                 265                 270 tct gaa gat ttt gga aat gaa aaa tca cag gaa cat ttt agt cac aat      981
Ser Glu Asp Phe Gly Asn Glu Lys Ser Gln Glu His Phe Ser His Asn
275                 280                 285 aca gtt cga gga tgt tct tat ttt tat aac tat cca gca gtg tgt gaa     1029
Thr Val Arg Gly Cys Ser Tyr Phe Tyr Asn Tyr Pro Ala Val Cys Glu
290                 295                 300                 305 ttt ttg caa aac aat aat ttg tta tcg att att aga gct cat gaa gct     1077
Phe Leu Gln Asn Asn Asn Leu Leu Ser Ile Ile Arg Ala His Glu Ala
                310                 315                 320 caa gat gca ggc tat aga atg tac aga aaa agt caa act aca ggg ttc     1125
Gln Asp Ala Gly Tyr Arg Met Tyr Arg Lys Ser Gln Thr Thr Gly Phe
            325                 330                 335 cct tca tta ata aca att ttt tcg gca cct aat tac tta gat gtc tac     1173
Pro Ser Leu Ile Thr Ile Phe Ser Ala Pro Asn Tyr Leu Asp Val Tyr
        340                 345                 350 aat aat aaa gct gct gta tta aag tat gaa aat aat gtg atg aat att     1221
Asn Asn Lys Ala Ala Val Leu Lys Tyr Glu Asn Asn Val Met Asn Ile
    355                 360                 365 cga cag ttt aac tgt tct cca cat cct tac tgg ttg cct aat ttt atg     1269
Arg Gln Phe Asn Cys Ser Pro His Pro Tyr Trp Leu Pro Asn Phe Met
370                 375                 380                 385 gat gtc ttc acg tgg tct tta ccg ttt gtt gga gaa aaa gtg aca gaa     1317
Asp Val Phe Thr Trp Ser Leu Pro Phe Val Gly Glu Lys Val Thr Glu
                390                 395                 400 atg ttg gta aat gtt ctg agt att tgc tct gat gat gaa cta atg act     1365
Met Leu Val Asn Val Leu Ser Ile Cys Ser Asp Asp Glu Leu Met Thr
            405                 410                 415 gaa ggt gaa gac cag ttt gat ggt tca gct gca gcc cgg aaa gaa atc     1413
Glu Gly Glu Asp Gln Phe Asp Gly Ser Ala Ala Ala Arg Lys Glu Ile
        420                 425                 430 ata aga aac aaa att cga gca att ggc aag atg gca aga gtc ttc tct     1461
Ile Arg Asn Lys Ile Arg Ala Ile Gly Lys Met Ala Arg Val Phe Ser
    435                 440                 445 gtt ctc agg gag gag agt gaa agt gtg ctg aca ctc aag ggc ctg act     1509
Val Leu Arg Glu Glu Ser Glu Ser Val Leu Thr Leu Lys Gly Leu Thr
450                 455                 460                 465 ccc aca ggg atg ttg cct agt gga gtg tta gct gga gga cgg cag acc     1557
Pro Thr Gly Met Leu Pro Ser Gly Val Leu Ala Gly Gly Arg Gln Thr
                470                 475                 480 ctg caa agt gcc aca gtt gag gct att gag gct gaa aaa gca ata cga     1605
Leu Gln Ser Ala Thr Val Glu Ala Ile Glu Ala Glu Lys Ala Ile Arg
            485                 490                 495 gga ttc tct cca cca cat aga atc tgc agt ttt gaa gag gca aag ggt     1653
Gly Phe Ser Pro Pro His Arg Ile Cys Ser Phe Glu Glu Ala Lys Gly
        500                 505                 510 ttg gat agg atc aat gag aga atg cca cct cgg aaa gat gct gta cag     1701
Leu Asp Arg Ile Asn Glu Arg Met Pro Pro Arg Lys Asp Ala Val Gln
    515                 520                 525 caa gat ggt ttc aat tct ctg aac acc gca cat gcc act gag aac cac     1749
Gln Asp Gly Phe Asn Ser Leu Asn Thr Ala His Ala Thr Glu Asn His
530                 535                 540                 545 ggg acg ggc aac cat act gcc cag tga ttaactaggg taccccgggg           1796
Gly Thr Gly Asn His Thr Ala Gln
```

```
                550
aaagaggaga aattaact atg gga aat gag gca agt tat cct ttg gaa atg    1847
                    Met Gly Asn Glu Ala Ser Tyr Pro Leu Glu Met
                    555             560             565 tgc tca cac ttt gat gcr gat gaa att aaa agg cta gga aag aga ttt    1895
Cys Ser His Phe Asp Xaa Asp Glu Ile Lys Arg Leu Gly Lys Arg Phe
            570             575             580 aag aag cty gat ttg gac aat tct ggt tct ttg agt gtg gaa gag ttc    1943
Lys Lys Xaa Asp Leu Asp Asn Ser Gly Ser Leu Ser Val Glu Glu Phe
        585             590             595 atg tct ctr cct gag tta caa cag aat ccy tta gta cag cga gta ata    1991
Met Ser Xaa Pro Glu Leu Gln Gln Asn Xaa Leu Val Gln Arg Val Ile
        600             605             610 gat ata ttc gac aca gat ggg aat gga gaa gta gac ttt aaa gar ttc    2039
Asp Ile Phe Asp Thr Asp Gly Asn Gly Glu Val Asp Phe Lys Glu Phe
        615             620             625 att gag ggm gtc tct cag ttc agt gtc aaa gga gat aag gar cag aar    2087
Ile Glu Xaa Val Ser Gln Phe Ser Val Lys Gly Asp Lys Glu Gln Lys
630             635             640             645 ttg agg ttt gct ttc cgt atc tat gac atg gat aaa gay ggc tat att    2135
Leu Arg Phe Ala Phe Arg Ile Tyr Asp Met Asp Lys Asp Gly Tyr Ile
            650             655             660 tcc aat ggg gaa ctc ttc cag gtr ytr aag atg atg gtg ggg aac aat    2183
Ser Asn Gly Glu Leu Phe Gln Xaa Xaa Lys Met Met Val Gly Asn Asn
            665             670             675 ctg aaa gat aca cag tta cag caa att gta gac aaa acc ata ata aat    2231
Leu Lys Asp Thr Gln Leu Gln Gln Ile Val Asp Lys Thr Ile Ile Asn
        680             685             690 gca gat aag gat ggr gat gga aga ata tcc ttt gaa gaa ttc tgt gct    2279
Ala Asp Lys Asp Xaa Asp Gly Arg Ile Ser Phe Glu Glu Phe Cys Ala
        695             700             705 gtt gta ggy ggc cta gat atc cac aaa aag atg gtg gta gat gtg tga    2327
Val Val Xaa Gly Leu Asp Ile His Lys Lys Met Val Val Asp Val
710             715             720             725 ttaattagaa gcttaattag ctgagcttgg actcctgttg atagatccag taatgacctc    2387
agaactccat ctggatttgt tcagaacgct cggttgccgc cgggcgtttt ttattggtga    2447
gaatccaagc tagcttggcg agattttcag gagctaagga agctaaaatg gagaaaaaaa    2507
tcactggata taccaccgtt gatatatccc aatggcatcg taaagaacat tttgaggcat    2567
ttcagtcagt tgctcaatgt acctataacc agaccgttca gctggatatt acggccttttt    2627
taaagaccgt aaagaaaaat aagcacaagt tttatccggc ctttattcac attcttgccc    2687
gcctgatgaa tgctcatccg gaatttcgta tggcaatgaa agacggtgag ctggtgatat    2747
gggatagtgt tcacccttgt tacaccgttt tccatgagca aactgaaacg ttttcatcgc    2807
tctggagtga ataccacgac gatttccggc agtttctaca catatattcg caagatgtgg    2867
cgtgttacgg tgaaaacctg gcctatttcc ctaaagggtt tattgagaat atgttttttcg    2927
tctcagccaa tccctgggtg agtttcacca gttttgattt aaacgtggcc aatatggaca    2987
acttcttcgc cccgtttttc accatgggca aatattatac gcaaggcgac aaggtgctga    3047
tgccgctggc gattcaggtt catcatgccg tctgtgatgg cttccatgtc ggcagaatgc    3107
ttaatgaatt acaacagtac tgcgatgagt ggcagggcgg ggcgtaattt ttttaaggca    3167
gttattggtg cccttaaacg cctggggtaa tgactctcta gcttgaggca tcaaataaaa    3227
cgaaaggctc agtcgaaaga ctgggccttt cgttttatct gttgtttgtc ggtgaacgct    3287
ctcctgagta ggacaaatcc gccgctctag agctgcctcg cgcgtttcgg tgatgacggt    3347
```

-continued

```
gaaaacctct gacacatgca gctcccggag acggtcacag cttgtctgta agcggatgcc    3407
gggagcagac aagcccgtca gggcgcgtca gcgggtgttg gcgggtgtcg gggcgcagcc    3467
atgacccagt cacgtagcga tagcggagtg tatactggct taactatgcg gcatcagagc    3527
agattgtact gagagtgcac catatgcggt gtgaaatacc gcacagatgc gtaaggagaa    3587
aataccgcat caggcgctct tccgcttcct cgctcactga ctcgctgcgc tcggtctgtc    3647
ggctgcggcg agcggtatca gctcactcaa aggcggtaat acggttatcc acagaatcag    3707
gggataacgc aggaaagaac atgtgagcaa aaggccagca aaaggccagg aaccgtaaaa    3767
aggccgcgtt gctggcgttt ttccataggc tccgcccccc tgacgagcat cacaaaaatc    3827
gacgctcaag tcagaggtgg cgaaacccga caggactata agataccagg cgtttcccc    3887 ctggaagctc cctcgtgcgc tctcctgttc cgaccctgcc gcttaccgga tacctgtccg    3947
cctttctccc ttcgggaagc gtggcgcttt ctcaatgctc acgctgtagg tatctcagtt    4007
cggtgtaggt cgttcgctcc aagctgggct gtgtgcacga acccccgtt cagcccgacc    4067 gctgcgcctt atccggtaac tatcgtcttg agtccaaccc ggtaagacac gacttatcgc    4127
cactggcagc agccactggt aacaggatta gcagagcgag gtatgtaggc ggtgctacag    4187
agttcttgaa gtggtggcct aactacggct acactagaag gacagtattt ggtatctgcg    4247
ctctgctgaa gccagttacc ttcggaaaaa gagttggtag ctcttgatcc ggcaaacaaa    4307
ccaccgctgg tagcggtggt ttttttgttt gcaagcagca gattacgcgc agaaaaaaag    4367
gatctcaaga agatcctttg atcttttcta cggggtctga cgctcagtgg aacgaaaact    4427
cacgttaagg gattttggtc atgagattat caaaaaggat cttcacctag atcctttaa    4487 attaaaaatg aagttttaaa tcaatctaaa gtatatatga gtaaacttgg tctgacagtt    4547
accaatgctt aatcagtgag gcacctatct cagcgatctg tctatttcgt tcatccatag    4607
ctgcctgact ccccgtcgtg tagataacta cgatacggga gggcttacca tctggcccca    4667
gtgctgcaat gataccgcga gacccacgct caccggctcc agatttatca gcaataaacc    4727
agccagccgg aagggccgag cgcagaagtg gtcctgcaac tttatccgcc tccatccagt    4787
ctattaattg ttgccgggaa gctagagtaa gtagttcgcc agttaatagt ttgcgcaacg    4847
ttgttgccat tgctacaggc atcgtggtgt cacgctcgtc gtttggtatg gcttcattca    4907
gctccggttc ccaacgatca aggcgagtta catgatcccc catgttgtgc aaaaaagcgg    4967
ttagctcctt cggtcctccg atcgttgtca gaagtaagtt ggccgcagtg ttatcactca    5027
tggttatggc agcactgcat aattctctta ctgtcatgcc atccgtaaga tgcttttctg    5087
tgactggtga gtactcaacc aagtcattct gagaatagtg tatgcggcga ccgagttgct    5147
cttgcccggc gtcaatacgg gataataccg cgccacatag cagaacttta aaagtgctca    5207
tcattggaaa acgttcttcg gggcgaaaac tctcaaggat cttaccgctg ttgagatcca    5267
gttcgatgta acccactcgt gcacccaact gatcttcagc atcttttact ttcaccagcg    5327
tttctgggtg agcaaaaaca ggaaggcaaa atgccgcaaa aaagggaata agggcgacac    5387
ggaaatgttg aatactcata ctcttccttt ttcaatatta ttgaagcatt tatcagggtt    5447
attgtctcat gagcggatac atatttgaat gtatttagaa aaataaacaa ataggggttc    5507
cgcgcacatt tccccgaaaa gtgccacctg acgtctaaga aaccattatt atcatgacat    5567
taacctataa aaataggcgt atcacgaggc cctttcgtct tcac    5611
```

<210> SEQ ID NO 27

-continued

<211> LENGTH: 553
<212> TYPE: PRT
<213> ORGANISM: Homo sapiens

<400> SEQUENCE: 27

```
Met Arg Gly Ser His His His His His His Gly Ser Ala Ala Pro Glu
 1               5                  10                  15

Pro Ala Arg Ala Ala Pro Pro Pro Pro Pro Pro Pro Pro Pro Pro Pro
            20                  25                  30

Gly Ala Asp Arg Val Val Lys Ala Val Pro Phe Pro Pro Thr His Arg
        35                  40                  45

Leu Thr Ser Glu Glu Val Phe Asp Leu Asp Gly Ile Pro Arg Val Asp
    50                  55                  60

Val Leu Lys Asn His Leu Val Lys Gly Arg Val Asp Glu Glu Ile
65                  70                  75                  80

Ala Leu Arg Ile Ile Asn Glu Gly Ala Ala Ile Leu Arg Arg Glu Lys
                85                  90                  95

Thr Met Ile Glu Val Glu Ala Pro Ile Thr Val Cys Gly Asp Ile His
            100                 105                 110

Gly Gln Phe Phe Asp Leu Met Lys Leu Phe Glu Val Gly Gly Ser Pro
        115                 120                 125

Ala Asn Thr Arg Tyr Leu Phe Leu Gly Asp Tyr Val Asp Arg Gly Tyr
    130                 135                 140

Phe Ser Ile Glu His Val Leu Gly Thr Glu Asp Ile Ser Ile Asn Pro
145                 150                 155                 160

His Asn Asn Ile Asn Glu Cys Val Leu Tyr Leu Trp Val Leu Lys Ile
                165                 170                 175

Leu Tyr Pro Ser Thr Leu Phe Leu Leu Arg Gly Asn His Glu Cys Arg
            180                 185                 190

His Leu Thr Glu Tyr Phe Thr Phe Lys Gln Glu Cys Lys Ile Lys Tyr
        195                 200                 205

Ser Glu Arg Val Tyr Glu Ala Cys Met Glu Ala Phe Asp Ser Leu Pro
    210                 215                 220

Leu Ala Ala Leu Leu Asn Gln Gln Phe Leu Cys Val His Gly Gly Leu
225                 230                 235                 240

Ser Pro Glu Ile His Thr Leu Asp Asp Ile Arg Arg Leu Asp Arg Phe
                245                 250                 255

Lys Glu Pro Pro Ala Phe Gly Pro Met Cys Asp Leu Leu Trp Ser Asp
            260                 265                 270

Pro Ser Glu Asp Phe Gly Asn Glu Lys Ser Gln Glu His Phe Ser His
        275                 280                 285

Asn Thr Val Arg Gly Cys Ser Tyr Phe Tyr Asn Tyr Pro Ala Val Cys
    290                 295                 300

Glu Phe Leu Gln Asn Asn Asn Leu Leu Ser Ile Ile Arg Ala His Glu
305                 310                 315                 320

Ala Gln Asp Ala Gly Tyr Arg Met Tyr Arg Lys Ser Gln Thr Thr Gly
                325                 330                 335

Phe Pro Ser Leu Ile Thr Ile Phe Ser Ala Pro Asn Tyr Leu Asp Val
            340                 345                 350

Tyr Asn Asn Lys Ala Ala Val Leu Lys Tyr Glu Asn Asn Val Met Asn
        355                 360                 365

Ile Arg Gln Phe Asn Cys Ser Pro His Pro Tyr Trp Leu Pro Asn Phe
    370                 375                 380

Met Asp Val Phe Thr Trp Ser Leu Pro Phe Val Gly Glu Lys Val Thr
```

-continued

```
                385                 390                 395                 400
Glu Met Leu Val Asn Val Leu Ser Ile Cys Ser Asp Asp Glu Leu Met
                    405                 410                 415
Thr Glu Gly Glu Asp Gln Phe Asp Gly Ser Ala Ala Ala Arg Lys Glu
                420                 425                 430
Ile Ile Arg Asn Lys Ile Arg Ala Ile Gly Lys Met Ala Arg Val Phe
            435                 440                 445
Ser Val Leu Arg Glu Glu Ser Glu Ser Val Leu Thr Leu Lys Gly Leu
        450                 455                 460
Thr Pro Thr Gly Met Leu Pro Ser Gly Val Leu Ala Gly Gly Arg Gln
465                 470                 475                 480
Thr Leu Gln Ser Ala Thr Val Glu Ala Ile Glu Ala Glu Lys Ala Ile
                485                 490                 495
Arg Gly Phe Ser Pro Pro His Arg Ile Cys Ser Phe Glu Glu Ala Lys
                    500                 505                 510
Gly Leu Asp Arg Ile Asn Glu Arg Met Pro Pro Arg Lys Asp Ala Val
                515                 520                 525
Gln Gln Asp Gly Phe Asn Ser Leu Asn Thr Ala His Ala Thr Glu Asn
            530                 535                 540
His Gly Thr Gly Asn His Thr Ala Gln
545                 550

<210> SEQ ID NO 28
<211> LENGTH: 170
<212> TYPE: PRT
<213> ORGANISM: Homo sapiens
<220> FEATURE:
<221> NAME/KEY: misc_feature
<222> LOCATION: 17
<223> OTHER INFORMATION: Xaa = any amino acid
<221> NAME/KEY: misc_feature
<222> LOCATION: 30
<223> OTHER INFORMATION: Xaa = any amino acid
<221> NAME/KEY: misc_feature
<222> LOCATION: 46
<223> OTHER INFORMATION: Xaa = any amino acid
<221> NAME/KEY: misc_feature
<222> LOCATION: 53
<223> OTHER INFORMATION: Xaa = any amino acid
<221> NAME/KEY: misc_feature
<222> LOCATION: 78
<223> OTHER INFORMATION: Xaa = any amino acid
<221> NAME/KEY: misc_feature
<222> LOCATION: 115
<223> OTHER INFORMATION: Xaa = any amino acid
<221> NAME/KEY: misc_feature
<222> LOCATION: 116
<223> OTHER INFORMATION: Xaa = any amino acid
<221> NAME/KEY: misc_feature
<222> LOCATION: 144
<223> OTHER INFORMATION: Xaa = any amino acid
<221> NAME/KEY: misc_feature
<222> LOCATION: 158
<223> OTHER INFORMATION: Xaa = any amino acid

<400> SEQUENCE: 28

Met Gly Asn Glu Ala Ser Tyr Pro Leu Glu Met Cys Ser His Phe Asp
 1               5                  10                  15
Xaa Asp Glu Ile Lys Arg Leu Gly Lys Arg Phe Lys Lys Xaa Asp Leu
                20                  25                  30
Asp Asn Ser Gly Ser Leu Ser Val Glu Glu Phe Met Ser Xaa Pro Glu
            35                  40                  45
Leu Gln Gln Asn Xaa Leu Val Gln Arg Val Ile Asp Ile Phe Asp Thr
        50                  55                  60
```

```
Asp Gly Asn Gly Glu Val Asp Phe Lys Glu Phe Ile Glu Xaa Val Ser
 65                  70                  75                  80

Gln Phe Ser Val Lys Gly Asp Lys Glu Gln Lys Leu Arg Phe Ala Phe
                 85                  90                  95

Arg Ile Tyr Asp Met Asp Lys Asp Gly Tyr Ile Ser Asn Gly Glu Leu
            100                 105                 110

Phe Gln Xaa Xaa Lys Met Met Val Gly Asn Asn Leu Lys Asp Thr Gln
        115                 120                 125

Leu Gln Gln Ile Val Asp Lys Thr Ile Ile Asn Ala Asp Lys Asp Xaa
130                 135                 140

Asp Gly Arg Ile Ser Phe Glu Glu Phe Cys Ala Val Val Xaa Gly Leu
145                 150                 155                 160

Asp Ile His Lys Lys Met Val Val Asp Val
                165                 170

<210> SEQ ID NO 29
<211> LENGTH: 5498
<212> TYPE: DNA
<213> ORGANISM: Homo sapiens
<220> FEATURE:
<221> NAME/KEY: CDS
<222> LOCATION: (115)..(1659)
<223> OTHER INFORMATION: histidine tagged calcineurin A gamma1
<221> NAME/KEY: misc_feature
<222> LOCATION: (1660)..(1701)
<223> OTHER INFORMATION: ribosomal binding site, multiple cloning site 2
<221> NAME/KEY: CDS
<222> LOCATION: (1702)..(2214)
<223> OTHER INFORMATION: calcineurin B

<400> SEQUENCE: 29
ctcgagaaat cataaaaaat ttatttgctt tgtgagcgga taacaattat aatagattca      60
attgtgagcg gataacaatt tcacacagaa ttcattaaag aggagaaatt aact atg      117
                                                             Met
                                                              1 aga gga tcg cat cac cat cac cat cac gga tcc atg tcc ggg agg cgc      165
Arg Gly Ser His His His His His His Gly Ser Met Ser Gly Arg Arg
          5                  10                  15 ttc cac ctc tcc acc acc gac cgc gtc atc aaa gct gtc ccc ttt cct      213
Phe His Leu Ser Thr Thr Asp Arg Val Ile Lys Ala Val Pro Phe Pro
     20                  25                  30 cca acc caa cgg ctt act ttc aag gaa gta ttt gag aat ggg aaa cct      261
Pro Thr Gln Arg Leu Thr Phe Lys Glu Val Phe Glu Asn Gly Lys Pro
 35                  40                  45 aaa gtt gat gtt tta aaa aac cat ttg gta aag gaa gga cga ctg gaa      309
Lys Val Asp Val Leu Lys Asn His Leu Val Lys Glu Gly Arg Leu Glu
 50                  55                  60                  65 gag gaa gta gcc tta aag ata atc aat gat ggg gct gcc atc ctg agg      357
Glu Glu Val Ala Leu Lys Ile Ile Asn Asp Gly Ala Ala Ile Leu Arg
             70                  75                  80 caa gag aag act atg ata gaa gta gat gct cca atc aca gta tgt ggt      405
Gln Glu Lys Thr Met Ile Glu Val Asp Ala Pro Ile Thr Val Cys Gly
         85                  90                  95 gat att cat gga caa ttc ttt gac cta atg aag tta ttt gaa gtt gga      453
Asp Ile His Gly Gln Phe Phe Asp Leu Met Lys Leu Phe Glu Val Gly
        100                 105                 110 gga tca cct agt aac aca cgc tac ctc ttt ctg ggt gac tat gtg gac      501
Gly Ser Pro Ser Asn Thr Arg Tyr Leu Phe Leu Gly Asp Tyr Val Asp
    115                 120                 125 aga ggc tat ttc agt ata gag tgt gtg ctg tat tta tgg agt tta aag      549
```

```
                                                                         -continued Arg Gly Tyr Phe Ser Ile Glu Cys Val Leu Tyr Leu Trp Ser Leu Lys
130                 135                 140                 145 att aat cat ccc aaa aca ttg ttt ctg ctt cgg gga aat cat gaa tgc          597
Ile Asn His Pro Lys Thr Leu Phe Leu Leu Arg Gly Asn His Glu Cys
                150                 155                 160 agg cat ctt aca gac tat ttc acc ttc aaa cag gaa tgt cga atc aaa          645
Arg His Leu Thr Asp Tyr Phe Thr Phe Lys Gln Glu Cys Arg Ile Lys
            165                 170                 175 tat tcg gaa cag gtg tat gat gcc tgt atg gag aca ttt gac tgt ctt          693
Tyr Ser Glu Gln Val Tyr Asp Ala Cys Met Glu Thr Phe Asp Cys Leu
        180                 185                 190 cct ctt gct gcc ctc tta aac cag cag ttt ctc tgt gta cat gga gga          741
Pro Leu Ala Ala Leu Leu Asn Gln Gln Phe Leu Cys Val His Gly Gly
    195                 200                 205 atg tca cct gaa att act tct tta gat gac att agg aaa tta gac agg          789
Met Ser Pro Glu Ile Thr Ser Leu Asp Asp Ile Arg Lys Leu Asp Arg
210                 215                 220                 225 ttt acg gaa cct ccc gcc ttt gga cct gtg tgt gac ctg ctt tgg tct          837
Phe Thr Glu Pro Pro Ala Phe Gly Pro Val Cys Asp Leu Leu Trp Ser
                230                 235                 240 gat ccc tca gag gat tat ggc aat gag aag acc ttg gag cac tat acc          885
Asp Pro Ser Glu Asp Tyr Gly Asn Glu Lys Thr Leu Glu His Tyr Thr
            245                 250                 255 cac aac act gtc cga ggg tgc tct tat ttc tac agt tac cct gca gtt          933
His Asn Thr Val Arg Gly Cys Ser Tyr Phe Tyr Ser Tyr Pro Ala Val
        260                 265                 270 tgt gaa ttt ttg cag aac aat aat tta cta tca att atc aga gcc cat          981
Cys Glu Phe Leu Gln Asn Asn Asn Leu Leu Ser Ile Ile Arg Ala His
    275                 280                 285 gaa gcc caa gat gct ggg tat cga atg tac agg aag agc caa gcc aca         1029
Glu Ala Gln Asp Ala Gly Tyr Arg Met Tyr Arg Lys Ser Gln Ala Thr
290                 295                 300                 305 ggc ttt cca tca ctt att aca att ttc tct gcc ccc aat tac cta gat         1077
Gly Phe Pro Ser Leu Ile Thr Ile Phe Ser Ala Pro Asn Tyr Leu Asp
                310                 315                 320 gtc tat aac aat aaa gct gct gtg ttg aaa tat gaa aac aat gtc atg         1125
Val Tyr Asn Asn Lys Ala Ala Val Leu Lys Tyr Glu Asn Asn Val Met
            325                 330                 335 aat atc agg cag ttt aac tgt tct cca cac ccc tac tgg ctt cca aac         1173
Asn Ile Arg Gln Phe Asn Cys Ser Pro His Pro Tyr Trp Leu Pro Asn
        340                 345                 350 ttt atg gat gtt ttc aca tgg tct ttg cct ttt gtt ggg gaa aaa gtc         1221
Phe Met Asp Val Phe Thr Trp Ser Leu Pro Phe Val Gly Glu Lys Val
    355                 360                 365 aca gag atg ctg gta aat gtg ctc aac ata tgc tct gat gac gaa ctg         1269
Thr Glu Met Leu Val Asn Val Leu Asn Ile Cys Ser Asp Asp Glu Leu
370                 375                 380                 385 att tct gat gat gaa gca gaa gga agc act aca gtt cgt aag gag atc         1317
Ile Ser Asp Asp Glu Ala Glu Gly Ser Thr Thr Val Arg Lys Glu Ile
                390                 395                 400 atc agg aat aag atc aga gcc att ggg aag atg gca cgg gtc ttt tca         1365
Ile Arg Asn Lys Ile Arg Ala Ile Gly Lys Met Ala Arg Val Phe Ser
            405                 410                 415 att ctt cgg caa gaa agt gag agt gtg ctg act ctc aag ggc ctg act         1413
Ile Leu Arg Gln Glu Ser Glu Ser Val Leu Thr Leu Lys Gly Leu Thr
        420                 425                 430 ccc aca ggc aca ctc cct ctg ggc gtc ctc tca gga ggc aag cag act         1461
Pro Thr Gly Thr Leu Pro Leu Gly Val Leu Ser Gly Gly Lys Gln Thr
    435                 440                 445
```

```
atc gag aca gcc atc aga ggg ttc tcg ctt cag cac aag atc cgg agt    1509
Ile Glu Thr Ala Ile Arg Gly Phe Ser Leu Gln His Lys Ile Arg Ser
450                 455                 460                 465 ttt gaa gaa gcg cga ggt ctg gac cga att aat gag cga atg cca ccc    1557
Phe Glu Glu Ala Arg Gly Leu Asp Arg Ile Asn Glu Arg Met Pro Pro
                470                 475                 480 cga aag gat agc ata tac cct ggt ggg cca atg aaa tct gta acc tca    1605
Arg Lys Asp Ser Ile Tyr Pro Gly Gly Pro Met Lys Ser Val Thr Ser
            485                 490                 495 gca cac tca cat gct gcg cac agg agc gac caa ggg aag aaa gcc cat    1653
Ala His Ser His Ala Ala His Arg Ser Asp Gln Gly Lys Lys Ala His
        500                 505                 510 tca tga ttaactaggg taccccgggg taccaaagag gagaaattaa ct atg gga     1707
Ser                                                     Met Gly
    515 aat gag gca agt tat cct ttg gaa atg tgc tca cac ttt gat gca gat    1755
Asn Glu Ala Ser Tyr Pro Leu Glu Met Cys Ser His Phe Asp Ala Asp
                520                 525                 530 gaa att aaa agg cta gga aag aga ttt aag aag ctc gat ttg gac aat    1803
Glu Ile Lys Arg Leu Gly Lys Arg Phe Lys Lys Leu Asp Leu Asp Asn
535                 540                 545 tct ggt tct ttg agt gtg gaa gag ttc atg tct cta cct gag tta caa    1851
Ser Gly Ser Leu Ser Val Glu Glu Phe Met Ser Leu Pro Glu Leu Gln
550                 555                 560                 565 cag aat ccc tta gta cag cga gta ata gat ata ttc gac aca gat ggg    1899
Gln Asn Pro Leu Val Gln Arg Val Ile Asp Ile Phe Asp Thr Asp Gly
                570                 575                 580 aat gga gaa gta gac ttt aaa gag ttc att gag gga gtc tct cag ttc    1947
Asn Gly Glu Val Asp Phe Lys Glu Phe Ile Glu Gly Val Ser Gln Phe
            585                 590                 595 agt gtc aaa gga gat aag gaa cag aag ttg agg ttt gct ttc cgt atc    1995
Ser Val Lys Gly Asp Lys Glu Gln Lys Leu Arg Phe Ala Phe Arg Ile
        600                 605                 610 tat gac atg gat aaa gac ggc tat att tcc aat ggg gaa ctc ttc cag    2043
Tyr Asp Met Asp Lys Asp Gly Tyr Ile Ser Asn Gly Glu Leu Phe Gln
615                 620                 625 gtg cta aag atg atg gtg ggg aac aat ctg aaa gat aca cag tta cag    2091
Val Leu Lys Met Met Val Gly Asn Asn Leu Lys Asp Thr Gln Leu Gln
630                 635                 640                 645 caa att gta gac aaa acc ata ata aat gca gat aag gat ggg gat gga    2139
Gln Ile Val Asp Lys Thr Ile Ile Asn Ala Asp Lys Asp Gly Asp Gly
                650                 655                 660 aga ata tcc ttt gaa gaa ttc tgt gct gtt gta ggc ggc cta gat atc    2187
Arg Ile Ser Phe Glu Glu Phe Cys Ala Val Val Gly Gly Leu Asp Ile
            665                 670                 675 cac aaa aag atg gtg gta gat gtg tga ttaattagaa gcttaattag          2234
His Lys Lys Met Val Val Asp Val
        680                 685 ctgagcttgg actcctgttg atagatccag taatgacctc agaactccat ctggatttgt  2294
tcagaacgct cggttgccgc cgggcgtttt ttattggtga aatccaagc tagcttggcg   2354 agattttcag gagctaagga agctaaaatg gagaaaaaaa tcactggata taccaccgtt  2414
gatatatccc aatggcatcg taaagaacat tttgaggcat ttcagtcagt tgctcaatgt  2474
acctataacc agaccgttca gctggatatt acggcctttt taaagaccgt aaagaaaaat  2534
aagcacaagt tttatccggc ctttattcac attcttgccc gcctgatgaa tgctcatccg  2594
gaatttcgta tggcaatgaa agacggtgag ctggtgatat gggatagtgt tcacccttgt  2654
tacaccgttt tccatgagca aactgaaacg ttttcatcgc tctggagtga ataccacgac  2714
```

```
gatttccggc agtttctaca catatattcg caagatgtgg cgtgttacgg tgaaaacctg    2774
gcctatttcc ctaaagggtt tattgagaat atgttttttcg tctcagccaa tccctgggtg   2834
agtttcacca gttttgattt aaacgtggcc aatatggaca acttcttcgc cccgttttc    2894
accatgggca aatattatac gcaaggcgac aaggtgctga tgccgctggc gattcaggtt   2954
catcatgccg tctgtgatgg cttccatgtc ggcagaatgc ttaatgaatt acaacagtac   3014
tgcgatgagt ggcagggcgg ggcgtaattt ttttaaggca gttattggtg cccttaaacg   3074
cctgggtaa tgactctcta gcttgaggca tcaaataaaa cgaaaggctc agtcgaaaga    3134
ctggcctttt cgttttatct gttgtttgtc ggtgaacgct ctcctgagta ggacaaatcc   3194
gccgctctag agctgcctcg cgcgtttcgg tgatgacggt gaaaacctct gacacatgca   3254
gctcccggag acggtcacag cttgtctgta agcggatgcc gggagcagac aagcccgtca   3314
gggcgcgtca gcgggtgttg gcgggtgtcg ggcgcagcc atgacccagt cacgtagcga   3374
tagcggagtg tatactggct taactatgcg gcatcagagc agattgtact gagagtgcac   3434
catatgcggt gtgaaatacc gcacagatgc gtaaggagaa ataccgcat caggcgctct    3494
tccgcttcct cgctcactga ctcgctgcgc tcggtctgtc ggctgcggcg agcggtatca   3554
gctcactcaa aggcggtaat acggttatcc acagaatcag gggataacgc aggaaagaac   3614
atgtgagcaa aaggccagca aaaggccagg aaccgtaaaa aggccgcgtt gctggcgttt   3674
ttccataggc tccgcccccc tgacgagcat cacaaaaatc gacgctcaag tcagaggtgg   3734
cgaaacccga caggactata aagataccag gcgtttcccc ctggaagctc cctcgtgcgc   3794
tctcctgttc cgaccctgcc gcttaccgga tacctgtccg cctttctccc ttcgggaagc   3854
gtggcgcttt ctcaatgctc acgctgtagg tatctcagtt cggtgtaggt cgttcgctcc   3914
aagctgggct gtgtgcacga acccccgtt cagcccgacc gctgcgcctt atccggtaac    3974
tatcgtcttg agtccaaccc ggtaagacac gacttatcgc cactggcagc agccactggt   4034
aacaggatta gcagagcgag gtatgtaggc ggtgctacag agttcttgaa gtggtggcct   4094
aactacggct acactagaag gacagtattt ggtatctgcg ctctgctgaa gccagttacc   4154
ttcggaaaaa gagttggtag ctcttgatcc ggcaaacaaa ccaccgctgg tagcggtggt   4214
ttttttgttt gcaagcagca gattacgcgc agaaaaaaag gatctcaaga agatcctttg   4274
atcttttcta cggggtctga cgctcagtgg aacgaaaact cacgttaagg gattttggtc   4334
atgagattat caaaaaggat cttcacctag atccttttaa attaaaaatg aagttttaaa   4394
tcaatctaaa gtatatatga gtaaacttgg tctgacagtt accaatgctt aatcagtgag   4454
gcacctatct cagcgatctg tctatttcgt tcatccatag ctgcctgact ccccgtcgtg   4514
tagataacta cgatacggga gggcttacca tctggcccca gtgctgcaat gataccgcga   4574
gacccacgct caccggctcc agatttatca gcaataaacc agccagccgg aagggccgag   4634
cgcagaagtg gtcctgcaac tttatccgcc tccatccagt ctattaattg ttgccgggaa   4694
gctagagtaa gtagttcgcc agttaatagt ttgcgcaacg ttgttgccat tgctacaggc   4754
atcgtggtgt cacgctcgtc gtttggtatg gcttcattca gctccggttc ccaacgatca   4814
aggcgagtta catgatcccc catgttgtgc aaaaaagcgg ttagctcctt cggtcctccg   4874
atcgttgtca gaagtaagtt ggccgcagtg ttatcactca tggttatggc agcactgcat   4934
aattctctta ctgtcatgcc atccgtaaga tgcttttctg tgactggtga gtactcaacc   4994
aagtcattct gagaatagtg tatgcggcga ccgagttgct cttgcccggc gtcaatacgg   5054
```

-continued

```
gataataccg cgccacatag cagaacttta aaagtgctca tcattggaaa acgttcttcg    5114
gggcgaaaac tctcaaggat cttaccgctg ttgagatcca gttcgatgta acccactcgt    5174
gcacccaact gatcttcagc atctttact ttcaccagcg tttctgggtg agcaaaaaca     5234
ggaaggcaaa atgccgcaaa aaagggaata agggcgacac ggaaatgttg aatactcata    5294
ctcttccttt ttcaatatta ttgaagcatt tatcagggtt attgtctcat gagcggatac    5354
atatttgaat gtatttagaa aaataaacaa ataggggttc cgcgcacatt tccccgaaaa    5414
gtgccacctg acgtctaaga aaccattatt atcatgacat taacctataa aaataggcgt    5474
atcacgaggc cctttcgtct tcac                                           5498
```

<210> SEQ ID NO 30
<211> LENGTH: 514
<212> TYPE: PRT
<213> ORGANISM: Homo sapiens

<400> SEQUENCE: 30

```
Met Arg Gly Ser His His His His His His Gly Ser Met Ser Gly Arg
  1               5                  10                  15

Arg Phe His Leu Ser Thr Thr Asp Arg Val Ile Lys Ala Val Pro Phe
                 20                  25                  30

Pro Pro Thr Gln Arg Leu Thr Phe Lys Glu Val Phe Glu Asn Gly Lys
             35                  40                  45

Pro Lys Val Asp Val Leu Lys Asn His Leu Val Lys Glu Gly Arg Leu
         50                  55                  60

Glu Glu Glu Val Ala Leu Lys Ile Ile Asn Asp Gly Ala Ala Ile Leu
 65                  70                  75                  80

Arg Gln Glu Lys Thr Met Ile Glu Val Asp Ala Pro Ile Thr Val Cys
                 85                  90                  95

Gly Asp Ile His Gly Gln Phe Phe Asp Leu Met Lys Leu Phe Glu Val
                100                 105                 110

Gly Gly Ser Pro Ser Asn Thr Arg Tyr Leu Phe Leu Gly Asp Tyr Val
            115                 120                 125

Asp Arg Gly Tyr Phe Ser Ile Glu Cys Val Leu Tyr Leu Trp Ser Leu
        130                 135                 140

Lys Ile Asn His Pro Lys Thr Leu Phe Leu Arg Gly Asn His Glu
145                 150                 155                 160

Cys Arg His Leu Thr Asp Tyr Phe Thr Phe Lys Gln Glu Cys Arg Ile
                165                 170                 175

Lys Tyr Ser Glu Gln Val Tyr Asp Ala Cys Met Glu Thr Phe Asp Cys
            180                 185                 190

Leu Pro Leu Ala Ala Leu Leu Asn Gln Gln Phe Leu Cys Val His Gly
        195                 200                 205

Gly Met Ser Pro Glu Ile Thr Ser Leu Asp Asp Ile Arg Lys Leu Asp
    210                 215                 220

Arg Phe Thr Glu Pro Pro Ala Phe Gly Pro Val Cys Asp Leu Leu Trp
225                 230                 235                 240

Ser Asp Pro Ser Glu Asp Tyr Gly Asn Glu Lys Thr Leu Glu His Tyr
                245                 250                 255

Thr His Asn Thr Val Arg Gly Cys Ser Tyr Phe Tyr Ser Tyr Pro Ala
            260                 265                 270

Val Cys Glu Phe Leu Gln Asn Asn Asn Leu Leu Ser Ile Ile Arg Ala
        275                 280                 285

His Glu Ala Gln Asp Ala Gly Tyr Arg Met Tyr Arg Lys Ser Gln Ala
```

```
                  290                 295                 300
Thr Gly Phe Pro Ser Leu Ile Thr Ile Phe Ser Ala Pro Asn Tyr Leu
305                 310                 315                 320

Asp Val Tyr Asn Asn Lys Ala Ala Val Leu Lys Tyr Glu Asn Asn Val
                325                 330                 335

Met Asn Ile Arg Gln Phe Asn Cys Ser Pro His Pro Tyr Trp Leu Pro
                340                 345                 350

Asn Phe Met Asp Val Phe Thr Trp Ser Leu Pro Phe Val Gly Glu Lys
                355                 360                 365

Val Thr Glu Met Leu Val Asn Val Leu Asn Ile Cys Ser Asp Asp Glu
370                 375                 380

Leu Ile Ser Asp Asp Glu Ala Glu Gly Ser Thr Thr Val Arg Lys Glu
385                 390                 395                 400

Ile Ile Arg Asn Lys Ile Arg Ala Ile Gly Lys Met Ala Arg Val Phe
                405                 410                 415

Ser Ile Leu Arg Gln Glu Ser Glu Ser Val Leu Thr Leu Lys Gly Leu
                420                 425                 430

Thr Pro Thr Gly Thr Leu Pro Leu Gly Val Leu Ser Gly Lys Gln
                435                 440                 445

Thr Ile Glu Thr Ala Ile Arg Gly Phe Ser Leu Gln His Lys Ile Arg
                450                 455                 460

Ser Phe Glu Glu Ala Arg Gly Leu Asp Arg Ile Asn Glu Arg Met Pro
465                 470                 475                 480

Pro Arg Lys Asp Ser Ile Tyr Pro Gly Gly Pro Met Lys Ser Val Thr
                485                 490                 495

Ser Ala His Ser His Ala Ala His Arg Ser Asp Gln Gly Lys Lys Ala
                500                 505                 510

His Ser

<210> SEQ ID NO 31
<211> LENGTH: 170
<212> TYPE: PRT
<213> ORGANISM: Homo sapiens

<400> SEQUENCE: 31

Met Gly Asn Glu Ala Ser Tyr Pro Leu Glu Met Cys Ser His Phe Asp
1               5                   10                  15

Ala Asp Glu Ile Lys Arg Leu Gly Lys Arg Phe Lys Lys Leu Asp Leu
                20                  25                  30

Asp Asn Ser Gly Ser Leu Ser Val Glu Glu Phe Met Ser Leu Pro Glu
                35                  40                  45

Leu Gln Gln Asn Pro Leu Val Gln Arg Val Ile Asp Ile Phe Asp Thr
            50                  55                  60

Asp Gly Asn Gly Glu Val Asp Phe Lys Glu Phe Ile Glu Gly Val Ser
65              70                  75                  80

Gln Phe Ser Val Lys Gly Asp Lys Glu Gln Lys Leu Arg Phe Ala Phe
                85                  90                  95

Arg Ile Tyr Asp Met Asp Lys Asp Gly Tyr Ile Ser Asn Gly Glu Leu
                100                 105                 110

Phe Gln Val Leu Lys Met Met Val Gly Asn Asn Leu Lys Asp Thr Gln
            115                 120                 125

Leu Gln Gln Ile Val Asp Lys Thr Ile Ile Asn Ala Asp Lys Asp Gly
            130                 135                 140

Asp Gly Arg Ile Ser Phe Glu Glu Phe Cys Ala Val Val Gly Gly Leu
```

-continued

```
                    145                 150                 155                 160
Asp Ile His Lys Lys Met Val Val Asp Val
                165                 170

<210> SEQ ID NO 32
<211> LENGTH: 5528
<212> TYPE: DNA
<213> ORGANISM: Homo sapiens
<220> FEATURE:
<221> NAME/KEY: CDS
<222> LOCATION: (115)..(1689)
<223> OTHER INFORMATION: histidine tagged calcineurin A gamma2
<221> NAME/KEY: misc_feature
<222> LOCATION: (1690)..(1731)
<223> OTHER INFORMATION: ribosomal binding site, multiple cloning site 2
<221> NAME/KEY: CDS
<222> LOCATION: (1732)..(2244)
<223> OTHER INFORMATION: calcineurin B
<221> NAME/KEY: variation
<222> LOCATION: (1474)..(1503)
<223> OTHER INFORMATION: splicevariant: substution with ACAGTAGAAG
      CGGTAGAGGC CCGGGAAGCC, interaction domain with cytoskeleton,
      death-domain homolog, stomatin homolog

<400> SEQUENCE: 32
ctcgagaaat cataaaaaat ttatttgctt tgtgagcgga taacaattat aatagattca     60
attgtgagcg gataacaatt tcacacagaa ttcattaaag aggagaaatt aact atg     117
                                                              Met
                                                               1 aga gga tcg cat cac cat cac cat cac gga tcc atg tcc ggg agg cgc     165
Arg Gly Ser His His His His His His Gly Ser Met Ser Gly Arg Arg
             5                  10                  15 ttc cac ctc tcc acc acc gac cgc gtc atc aaa gct gtc ccc ttt cct     213
Phe His Leu Ser Thr Thr Asp Arg Val Ile Lys Ala Val Pro Phe Pro
         20                  25                  30 cca acc caa cgg ctt act ttc aag gaa gta ttt gag aat ggg aaa cct     261
Pro Thr Gln Arg Leu Thr Phe Lys Glu Val Phe Glu Asn Gly Lys Pro
     35                  40                  45 aaa gtt gat gtt tta aaa aac cat ttg gta aag gaa gga cga ctg gaa     309
Lys Val Asp Val Leu Lys Asn His Leu Val Lys Glu Gly Arg Leu Glu
 50                  55                  60                  65 gag gaa gta gcc tta aag ata atc aat gat ggg gct gcc atc ctg agg     357
Glu Glu Val Ala Leu Lys Ile Ile Asn Asp Gly Ala Ala Ile Leu Arg
                 70                  75                  80 caa gag aag act atg ata gaa gta gat gct cca atc aca gta tgt ggt     405
Gln Glu Lys Thr Met Ile Glu Val Asp Ala Pro Ile Thr Val Cys Gly
             85                  90                  95 gat att cat gga caa ttc ttt gac cta atg aag tta ttt gaa gtt gga     453
Asp Ile His Gly Gln Phe Phe Asp Leu Met Lys Leu Phe Glu Val Gly
        100                 105                 110 gga tca cct agt aac aca cgc tac ctc ttt ctg ggt gac tat gtg gac     501
Gly Ser Pro Ser Asn Thr Arg Tyr Leu Phe Leu Gly Asp Tyr Val Asp
    115                 120                 125 aga ggc tat ttc agt ata gag tgt gtg ctg tat tta tgg agt tta aag     549
Arg Gly Tyr Phe Ser Ile Glu Cys Val Leu Tyr Leu Trp Ser Leu Lys
130                 135                 140                 145 att aat cat ccc aaa aca ttg ttt ctg ctt cgg gga aat cat gaa tgc     597
Ile Asn His Pro Lys Thr Leu Phe Leu Leu Arg Gly Asn His Glu Cys
                150                 155                 160 agg cat ctt aca gac tat ttc acc ttc aaa cag gaa tgt cga atc aaa     645
Arg His Leu Thr Asp Tyr Phe Thr Phe Lys Gln Glu Cys Arg Ile Lys
            165                 170                 175 tat tcg gaa cag gtg tat gat gcc tgt atg gag aca ttt gac tgt ctt     693
```

```
                Tyr Ser Glu Gln Val Tyr Asp Ala Cys Met Glu Thr Phe Asp Cys Leu
                    180                 185                 190 cct ctt gct gcc ctc tta aac cag cag ttt ctc tgt gta cat gga gga                741
Pro Leu Ala Ala Leu Leu Asn Gln Gln Phe Leu Cys Val His Gly Gly
            195                 200                 205 atg tca cct gaa att act tct tta gat gac att agg aaa tta gac agg                789
Met Ser Pro Glu Ile Thr Ser Leu Asp Asp Ile Arg Lys Leu Asp Arg
210                 215                 220                 225 ttt acg gaa cct ccc gcc ttt gga cct gtg tgt gac ctg ctt tgg tct                837
Phe Thr Glu Pro Pro Ala Phe Gly Pro Val Cys Asp Leu Leu Trp Ser
                        230                 235                 240 gat ccc tca gag gat tat ggc aat gag aag acc ttg gag cac tat acc                885
Asp Pro Ser Glu Asp Tyr Gly Asn Glu Lys Thr Leu Glu His Tyr Thr
            245                 250                 255 cac aac act gtc cga ggg tgc tct tat ttc tac agt tac cct gca gtt                933
His Asn Thr Val Arg Gly Cys Ser Tyr Phe Tyr Ser Tyr Pro Ala Val
        260                 265                 270 tgt gaa ttt ttg cag aac aat aat tta cta tca att atc aga gcc cat                981
Cys Glu Phe Leu Gln Asn Asn Asn Leu Leu Ser Ile Ile Arg Ala His
    275                 280                 285 gaa gcc caa gat gct ggg tat cga atg tac agg aag agc caa gcc aca               1029
Glu Ala Gln Asp Ala Gly Tyr Arg Met Tyr Arg Lys Ser Gln Ala Thr
290                 295                 300                 305 ggc ttt cca tca ctt att aca att ttc tct gcc ccc aat tac cta gat               1077
Gly Phe Pro Ser Leu Ile Thr Ile Phe Ser Ala Pro Asn Tyr Leu Asp
                        310                 315                 320 gtc tat aac aat aaa gct gct gtg ttg aaa tat gaa aac aat gtc atg               1125
Val Tyr Asn Asn Lys Ala Ala Val Leu Lys Tyr Glu Asn Asn Val Met
            325                 330                 335 aat atc agg cag ttt aac tgt tct cca cac ccc tac tgg ctt cca aac               1173
Asn Ile Arg Gln Phe Asn Cys Ser Pro His Pro Tyr Trp Leu Pro Asn
        340                 345                 350 ttt atg gat gtt ttc aca tgg tct ttg cct ttt gtt ggg gaa aaa gtc               1221
Phe Met Asp Val Phe Thr Trp Ser Leu Pro Phe Val Gly Glu Lys Val
    355                 360                 365 aca gag atg ctg gta aat gtg ctc aac ata tgc tct gat gac gaa ctg               1269
Thr Glu Met Leu Val Asn Val Leu Asn Ile Cys Ser Asp Asp Glu Leu
370                 375                 380                 385 att tct gat gat gaa gca gaa gga agc act aca gtt cgt aag gag atc               1317
Ile Ser Asp Asp Glu Ala Glu Gly Ser Thr Thr Val Arg Lys Glu Ile
                        390                 395                 400 atc agg aat aag atc aga gcc att ggg aag atg gca cgg gtc ttt tca               1365
Ile Arg Asn Lys Ile Arg Ala Ile Gly Lys Met Ala Arg Val Phe Ser
            405                 410                 415 att ctt cgg caa gaa agt gag agt gtg ctg act ctc aag ggc ctg act               1413
Ile Leu Arg Gln Glu Ser Glu Ser Val Leu Thr Leu Lys Gly Leu Thr
        420                 425                 430 ccc aca ggc aca ctc cct ctg ggc gtc ctc tca gga ggc aag cag act               1461
Pro Thr Gly Thr Leu Pro Leu Gly Val Leu Ser Gly Gly Lys Gln Thr
    435                 440                 445 atc gag aca gcc aaa caa gaa gcc gca gag gag cgg gaa gcc atc aga               1509
Ile Glu Thr Ala Lys Gln Glu Ala Ala Glu Glu Arg Glu Ala Ile Arg
450                 455                 460                 465 ggg ttc tcg ctt cag cac aag atc cgg agt ttt gaa gaa gcg cga ggt               1557
Gly Phe Ser Leu Gln His Lys Ile Arg Ser Phe Glu Glu Ala Arg Gly
                        470                 475                 480 ctg gac cga att aat gag cga atg cca ccc cga aag gat agc ata tac               1605
Leu Asp Arg Ile Asn Glu Arg Met Pro Pro Arg Lys Asp Ser Ile Tyr
            485                 490                 495
```

```
cct ggt ggg cca atg aaa tct gta acc tca gca cac tca cat gct gcg        1653
Pro Gly Gly Pro Met Lys Ser Val Thr Ser Ala His Ser His Ala Ala
            500                 505                 510 cac agg agc gac caa ggg aag aaa gcc cat tca tga ttaactaggg             1699
His Arg Ser Asp Gln Gly Lys Lys Ala His Ser
515                 520                 525 taccccgggg taccaaagag gagaaattaa ct atg gga aat gag gca agt tat        1752
                                   Met Gly Asn Glu Ala Ser Tyr
                                                           530 cct ttg gaa atg tgc tca cac ttt gat gca gat gaa att aaa agg cta        1800
Pro Leu Glu Met Cys Ser His Phe Asp Ala Asp Glu Ile Lys Arg Leu
            535                 540                 545 gga aag aga ttt aag aag ctc gat ttg gac aat tct ggt tct ttg agt        1848
Gly Lys Arg Phe Lys Lys Leu Asp Leu Asp Asn Ser Gly Ser Leu Ser
550                 555                 560 gtg gaa gag ttc atg tct cta cct gag tta caa cag aat ccc tta gta        1896
Val Glu Glu Phe Met Ser Leu Pro Glu Leu Gln Gln Asn Pro Leu Val
565                 570                 575                 580 cag cga gta ata gat ata ttc gac aca gat ggg aat gga gaa gta gac        1944
Gln Arg Val Ile Asp Ile Phe Asp Thr Asp Gly Asn Gly Glu Val Asp
                585                 590                 595 ttt aaa gag ttc att gag gga gtc tct cag ttc agt gtc aaa gga gat        1992
Phe Lys Glu Phe Ile Glu Gly Val Ser Gln Phe Ser Val Lys Gly Asp
            600                 605                 610 aag gaa cag aag ttg agg ttt gct ttc cgt atc tat gac atg gat aaa        2040
Lys Glu Gln Lys Leu Arg Phe Ala Phe Arg Ile Tyr Asp Met Asp Lys
            615                 620                 625 gac ggc tat att tcc aat ggg gaa ctc ttc cag gtg cta aag atg atg        2088
Asp Gly Tyr Ile Ser Asn Gly Glu Leu Phe Gln Val Leu Lys Met Met
630                 635                 640 gtg ggg aac aat ctg aaa gat aca cag tta cag caa att gta gac aaa        2136
Val Gly Asn Asn Leu Lys Asp Thr Gln Leu Gln Gln Ile Val Asp Lys
645                 650                 655                 660 acc ata ata aat gca gat aag gat ggg gat gga aga ata tcc ttt gaa        2184
Thr Ile Ile Asn Ala Asp Lys Asp Gly Asp Gly Arg Ile Ser Phe Glu
                665                 670                 675 gaa ttc tgt gct gtt gta ggc ggc cta gat atc cac aaa aag atg gtg        2232
Glu Phe Cys Ala Val Val Gly Gly Leu Asp Ile His Lys Lys Met Val
            680                 685                 690 gta gat gtg tga ttaattagaa gcttaattag ctgagcttgg actcctgttg            2284
Val Asp Val
695 atagatccag taatgacctc agaactccat ctggatttgt tcagaacgct cggttgccgc      2344 cgggcgtttt ttattggtga gaatccaagc tagcttggcg agattttcag gagctaagga      2404 agctaaaatg gagaaaaaaa tcactggata taccaccgtt gatatatccc aatggcatcg      2464 taaagaacat tttgaggcat ttcagtcagt tgctcaatgt acctataacc agaccgttca      2524 gctggatatt acggcctttt taagaccgt aaagaaaaat aagcacaagt tttatccggc       2584 ctttattcac attcttgccc gcctgatgaa tgctcatccg gaatttcgta tggcaatgaa      2644 agacggtgag ctggtgatat gggatagtgt tcacccttgt tacaccgttt tccatgagca      2704 aactgaaacg ttttcatcgc tctggagtga ataccacgac gatttccggc agtttctaca      2764 catatattcg caagatgtgg cgtgttacgg tgaaaacctg gcctatttcc ctaaagggtt      2824 tattgagaat atgttttcg tctcagccaa tccctgggtg agtttcacca gttttgattt      2884 aaacgtggcc aatatggaca acttcttcgc cccgttttc accatgggca atatattac       2944 gcaaggcgac aaggtgctga tgccgctggc gattcaggtt catcatgccg tctgtgatgg      3004
```

-continued

```
cttccatgtc ggcagaatgc ttaatgaatt acaacagtac tgcgatgagt ggcagggcgg   3064
ggcgtaattt ttttaaggca gttattggtg cccttaaacg cctggggtaa tgactctcta   3124
gcttgaggca tcaaataaaa cgaaaggctc agtcgaaaga ctgggccttt cgttttatct   3184
gttgtttgtc ggtgaacgct ctcctgagta ggacaaatcc gccgctctag agctgcctcg   3244
cgcgtttcgg tgatgacggt gaaaacctct gacacatgca gctcccggag acggtcacag   3304
cttgtctgta agcggatgcc gggagcagac aagcccgtca gggcgcgtca gcgggtgttg   3364
gcgggtgtcg gggcgcagcc atgacccagt cacgtagcga tagcggagtg tatactggct   3424
taactatgcg gcatcagagc agattgtact gagagtgcac catatgcggt gtgaaatacc   3484
gcacagatgc gtaaggagaa ataccgcat caggcgctct ccgcttcct cgctcactga    3544
ctcgctgcgc tcggtctgtc ggctgcggcg agcggtatca gctcactcaa aggcggtaat   3604
acggttatcc acagaatcag gggataacgc aggaaagaac atgtgagcaa aaggccagca   3664
aaaggccagg aaccgtaaaa aggccgcgtt gctggcgttt ttccataggc tccgccccc   3724
tgacgagcat cacaaaaatc gacgctcaag tcagaggtgg cgaaacccga caggactata   3784
aagataccag gcgtttcccc ctggaagctc cctcgtgcgc tctcctgttc cgaccctgcc   3844
gcttaccgga tacctgtccg cctttctccc ttcgggaagc gtggcgcttt ctcaatgctc   3904
acgctgtagg tatctcagtt cggtgtaggt cgttcgctcc aagctgggct gtgtgcacga   3964
accccccgtt cagcccgacc gctgcgcctt atccggtaac tatcgtcttg agtccaaccc   4024
ggtaagacac gacttatcgc cactggcagc agccactggt aacaggatta gcagagcgag   4084
gtatgtaggc ggtgctacag agttcttgaa gtggtggcct aactacggct acactagaag   4144
gacagtattt ggtatctgcg ctctgctgaa gccagttacc ttcggaaaaa gagttggtag   4204
ctcttgatcc ggcaaacaaa ccaccgctgg tagcggtggt ttttttgttt gcaagcagca   4264
gattacgcgc agaaaaaaag gatctcaaga agatcctttg atcttttcta cggggtctga   4324
cgctcagtgg aacgaaaact cacgttaagg gattttggtc atgagattat caaaaaggat   4384
cttcacctag atccttttaa attaaaaatg aagttttaaa tcaatctaaa gtatatatga   4444
gtaaacttgg tctgacagtt accaatgctt aatcagtgag gcacctatct cagcgatctg   4504
tctatttcgt tcatccatag ctgcctgact ccccgtcgtg tagataacta cgatacggga   4564
gggcttacca tctggcccca gtgctgcaat gataccgcga gacccacgct caccggctcc   4624
agatttatca gcaataaacc agccagccgg aagggccgag cgcagaagtg gtcctgcaac   4684
tttatccgcc tccatccagt ctattaattg ttgccgggaa gctagagtaa gtagttcgcc   4744
agttaatagt ttgcgcaacg ttgttgccat tgctacaggc atcgtggtgt cacgctcgtc   4804
gtttggtatg gcttcattca gctccggttc ccaacgatca aggcgagtta catgatcccc   4864
catgttgtgc aaaaaagcgg ttagctcctt cggtcctccg atcgttgtca gaagtaagtt   4924
ggccgcagtg ttatcactca tggttatggc agcactgcat aattctctta ctgtcatgcc   4984
atccgtaaga tgcttttctg tgactggtga gtactcaacc aagtcattct gagaatagtg   5044
tatgcggcga ccgagttgct cttgcccggc gtcaatacgg gataataccg cgccacatag   5104
cagaacttta aaagtgctca tcattggaaa acgttcttcg gggcgaaaac tctcaaggat   5164
cttaccgctg ttgagatcca gttcgatgta acccactcgt gcacccaact gatcttcagc   5224
atcttttact ttcaccagcg tttctgggtg agcaaaaaca ggaaggcaaa atgccgcaaa   5284
aaagggaata agggcgacac ggaaatgttg aatactcata ctcttccttt ttcaatatta   5344
```

```
ttgaagcatt tatcagggtt attgtctcat gagcggatac atatttgaat gtatttagaa    5404
aaataaacaa atagggttc cgcgcacatt tccccgaaaa gtgccacctg acgtctaaga     5464
aaccattatt atcatgacat taacctataa aaataggcgt atcacgaggc cctttcgtct    5524
tcac                                                                5528
```

<210> SEQ ID NO 33
<211> LENGTH: 524
<212> TYPE: PRT
<213> ORGANISM: Homo sapiens

<400> SEQUENCE: 33

```
Met Arg Gly Ser His His His His His Gly Ser Met Ser Gly Arg
 1               5                  10                  15

Arg Phe His Leu Ser Thr Thr Asp Arg Val Ile Lys Ala Val Pro Phe
                20                  25                  30

Pro Pro Thr Gln Arg Leu Thr Phe Lys Glu Val Phe Glu Asn Gly Lys
            35                  40                  45

Pro Lys Val Asp Val Leu Lys Asn His Leu Val Lys Glu Gly Arg Leu
        50                  55                  60

Glu Glu Glu Val Ala Leu Lys Ile Ile Asn Asp Gly Ala Ala Ile Leu
65                  70                  75                  80

Arg Gln Glu Lys Thr Met Ile Glu Val Asp Ala Pro Ile Thr Val Cys
                85                  90                  95

Gly Asp Ile His Gly Gln Phe Phe Asp Leu Met Lys Leu Phe Glu Val
            100                 105                 110

Gly Gly Ser Pro Ser Asn Thr Arg Tyr Leu Phe Leu Gly Asp Tyr Val
        115                 120                 125

Asp Arg Gly Tyr Phe Ser Ile Glu Cys Val Leu Tyr Leu Trp Ser Leu
    130                 135                 140

Lys Ile Asn His Pro Lys Thr Leu Phe Leu Arg Gly Asn His Glu
145                 150                 155                 160

Cys Arg His Leu Thr Asp Tyr Phe Thr Phe Lys Gln Glu Cys Arg Ile
                165                 170                 175

Lys Tyr Ser Glu Gln Val Tyr Asp Ala Cys Met Glu Thr Phe Asp Cys
            180                 185                 190

Leu Pro Leu Ala Ala Leu Leu Asn Gln Gln Phe Leu Cys Val His Gly
        195                 200                 205

Gly Met Ser Pro Glu Ile Thr Ser Leu Asp Asp Ile Arg Lys Leu Asp
    210                 215                 220

Arg Phe Thr Glu Pro Pro Ala Phe Gly Pro Val Cys Asp Leu Leu Trp
225                 230                 235                 240

Ser Asp Pro Ser Glu Asp Tyr Gly Asn Glu Lys Thr Leu Glu His Tyr
                245                 250                 255

Thr His Asn Thr Val Arg Gly Cys Ser Tyr Phe Tyr Ser Tyr Pro Ala
            260                 265                 270

Val Cys Glu Phe Leu Gln Asn Asn Leu Leu Ser Ile Ile Arg Ala
        275                 280                 285

His Glu Ala Gln Asp Ala Gly Tyr Arg Met Tyr Arg Lys Ser Gln Ala
    290                 295                 300

Thr Gly Phe Pro Ser Leu Ile Thr Ile Phe Ser Ala Pro Asn Tyr Leu
305                 310                 315                 320

Asp Val Tyr Asn Asn Lys Ala Ala Val Leu Lys Tyr Glu Asn Asn Val
                325                 330                 335
```

```
Met Asn Ile Arg Gln Phe Asn Cys Ser Pro His Pro Tyr Trp Leu Pro
            340                 345                 350

Asn Phe Met Asp Val Phe Thr Trp Ser Leu Pro Phe Val Gly Glu Lys
        355                 360                 365

Val Thr Glu Met Leu Val Asn Val Leu Asn Ile Cys Ser Asp Asp Glu
370                 375                 380

Leu Ile Ser Asp Asp Glu Ala Glu Gly Ser Thr Thr Val Arg Lys Glu
385                 390                 395                 400

Ile Ile Arg Asn Lys Ile Arg Ala Ile Gly Lys Met Ala Arg Val Phe
                405                 410                 415

Ser Ile Leu Arg Gln Glu Ser Glu Ser Val Leu Thr Leu Lys Gly Leu
                420                 425                 430

Thr Pro Thr Gly Thr Leu Pro Leu Gly Val Leu Ser Gly Gly Lys Gln
                435                 440                 445

Thr Ile Glu Thr Ala Lys Gln Glu Ala Ala Glu Glu Arg Glu Ala Ile
            450                 455                 460

Arg Gly Phe Ser Leu Gln His Lys Ile Arg Ser Phe Glu Glu Ala Arg
465                 470                 475                 480

Gly Leu Asp Arg Ile Asn Glu Arg Met Pro Pro Arg Lys Asp Ser Ile
                485                 490                 495

Tyr Pro Gly Gly Pro Met Lys Ser Val Thr Ser Ala His Ser His Ala
                500                 505                 510

Ala His Arg Ser Asp Gln Gly Lys Lys Ala His Ser
            515                 520

<210> SEQ ID NO 34
<211> LENGTH: 170
<212> TYPE: PRT
<213> ORGANISM: Homo sapiens

<400> SEQUENCE: 34

Met Gly Asn Glu Ala Ser Tyr Pro Leu Glu Met Cys Ser His Phe Asp
 1               5                  10                  15

Ala Asp Glu Ile Lys Arg Leu Gly Lys Arg Phe Lys Lys Leu Asp Leu
                20                  25                  30

Asp Asn Ser Gly Ser Leu Ser Val Glu Glu Phe Met Ser Leu Pro Glu
            35                  40                  45

Leu Gln Gln Asn Pro Leu Val Gln Arg Val Ile Asp Ile Phe Asp Thr
        50                  55                  60

Asp Gly Asn Gly Glu Val Asp Phe Lys Glu Phe Ile Glu Gly Val Ser
65                  70                  75                  80

Gln Phe Ser Val Lys Gly Asp Lys Glu Gln Lys Leu Arg Phe Ala Phe
                85                  90                  95

Arg Ile Tyr Asp Met Asp Lys Asp Gly Tyr Ile Ser Asn Gly Glu Leu
                100                 105                 110

Phe Gln Val Leu Lys Met Met Val Gly Asn Asn Leu Lys Asp Thr Gln
            115                 120                 125

Leu Gln Gln Ile Val Asp Lys Thr Ile Ile Asn Ala Asp Lys Asp Gly
        130                 135                 140

Asp Gly Arg Ile Ser Phe Glu Glu Phe Cys Ala Val Val Gly Gly Leu
145                 150                 155                 160

Asp Ile His Lys Lys Met Val Val Asp Val
                165                 170

<210> SEQ ID NO 35
```

-continued

```
<211> LENGTH: 19
<212> TYPE: PRT
<213> ORGANISM: Bos taurus
<220> FEATURE:
<221> NAME/KEY: PEPTIDE
<222> LOCATION: (1)..(19)
<223> OTHER INFORMATION: peptide of cAMP regulated protein kinase A, RII
<221> NAME/KEY: MOD_RES
<222> LOCATION: (15)
<223> OTHER INFORMATION: PHOSPHORYLATION
<221> NAME/KEY: SITE
<222> LOCATION: (15)
<223> OTHER INFORMATION: artificial chemical modification by
      fluoroscein-phosphoramidite

<400> SEQUENCE: 35

Asp Leu Asp Val Pro Ile Pro Gly Arg Phe Asp Arg Arg Val Ser Val
 1               5                  10                  15

Ala Ala Glu
```